(12) United States Patent
Mathis

(10) Patent No.: US 7,205,388 B1
(45) Date of Patent: Apr. 17, 2007

(54) *BT* TOXIN RECEPTORS AND METHODS OF USE

(75) Inventor: John P. Mathis, Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 11/489,644

(22) Filed: Jul. 19, 2006

Related U.S. Application Data

(62) Division of application No. 10/798,058, filed on Mar. 11, 2004.

(60) Provisional application No. 60/455,085, filed on Mar. 14, 2003.

(51) Int. Cl.
*C07K 14/00* (2006.01)
*C12P 21/06* (2006.01)
*C07H 21/04* (2006.01)

(52) U.S. Cl. .................. 530/350; 435/69.1; 536/23.1

(58) Field of Classification Search ................... None
See application file for complete search history.

(56) References Cited

U.S. PATENT DOCUMENTS

| | | | |
|---|---|---|---|
| 5,693,491 | A | 12/1997 | Bulla et al. |
| 5,804,393 | A | 9/1998 | Geiser et al. |
| 6,007,981 | A | 12/1999 | Bulla |

FOREIGN PATENT DOCUMENTS

| | | |
|---|---|---|
| EP | 1 124 426 B1 | 1/2003 |
| WO | WO 96/12964 A1 | 2/1996 |
| WO | WO 98/59048 A1 | 12/1998 |
| WO | WO 01/34807 A2 | 5/2001 |
| WO | WO 01/36639 A2 | 5/2001 |
| WO | WO 02/074079 A2 | 9/2002 |

OTHER PUBLICATIONS

Dorsch, J.A., "Isolation and Characterization of the Insecticidal Toxin Binding Site From the Receptor BT-r₁ of *Manduca sexta*," May 1998, A dissertation submitted to the Department of Molecular Biology and the Graduate School of the University of Wyoming, Laramie, Wyoming.
Dorsch, J.A., et al., "CRYlA Toxins of *Bacillus thuringiensis* bind specifically to a region adjacent to the membrane-proximal extracellular domain of BT-R₁ in *Manduca sexta*: involvement of a cadherin in the entomopathogenicity of *Bacillus thuringiensis*," *Insect Biochemistry and Molecular Biology*, 2002, pp. 1025-1036, vol. 32.
Estruch, J.J., et al., "Transgenic plants: An emerging approach to pest control," *Nature Biotechnology*, Feb. 1997, pp. 137-141, vol. 15.
Francis, B.R., and Bulla, L.A., Jr., "Further Characterization of BT-R₁, the Cadherin-like Receptor for CrylAb Toxin in Tobacco Hornworm (*Manduca Sexta*) Midguts," *Insect Biochem. Molec. Biol.*, 1997, pp. 541-550, vol. 27, No. 6.

Franklin, S.W., et al., "Southern analysis of BT-R₁, the *Manduca sexta* gene encoding the receptor for the CrylAb toxin of *Bacillus thuringiensis*," *Mol Gen Genet*, 1997, pp. 517-524, vol. 256.
Gahan, J.L., et al., "Identification of a Gene Associated with Bt Resistance in *Heliothis virescens*," *Science*, Aug. 3, 2001, pp. 857-860, vol. 293.
Garczynski, S.F., et al., "Identification of Putative Insect Brush Border Membrane-Binding Molecules Specific to *Bacillus thuringiensis* δ-Endotoxin by Protein Blot Analysis," *Applied and Environmental Microbiology*, Oct. 1991, pp. 2816-2820, vol. 57, No. 10.
Gill, S.S., et al., "Identification, Isolation, and Cloning of a *Bacillus thuringiensis* CrylAc Toxin-binding Protein from the Midgut of the Lepidopteran Insect *Heliothis virescens*," *The Journal of Biological Chemistry*, Nov. 10, 1995, pp. 27277-27282, vol. 270, No. 45.
Hofte, H. and Whiteley, H.R., "Insecticidal Crystal Proteins of *Bacillus thuringiensis*," *Microbiological Reviews*, Jun. 1989, pp. 242-255, vol. 53, No. 3.
Hua, G., et al., "Binding Analyses of *Bacillus thuringiensis* Cry δ-Endotoxins Using Brush Border Membrane Vesicles of *Ostrinia nubilalis*," *Applied and Environmental Microbiology*, Feb. 2001, pp. 872-879, vol. 67, No. 2.
Ihara, H., et al., "Purification and partial amino acid sequences of the binding protein from *bombys mori* for CrylAa δ-endotoxin of *Bacillus thuringiensis*," *Comparative Biochemistry and Physiology*, Part B, 1998, pp. 197-204, vol. 120.
Jurat-Fuentes, J.L., et al., "Altered Glycosylation of 63-68-Kilodalton Microvillar Proteins in *Heliothis virescens* Correlates with Reduced Cryl Toxin Binding, Decreased Pore Formulation, and Increased Resistance to *Bacillus thuringiensis* Cryl Toxins," *Applied and Environmental Microbiology*, Nov. 2002, pp. 5711-5717, vol. 68, No. 11.
Keeton, T.P., and Bulla, L.A., Jr., "Ligand Specificity and Affinity of BT-R₁, the *Bacillus thuringiensis* CrylA Toxin Receptor from *Manduca sexta*, Expressed in Mammalian and Insect Cell Cultures," *Applied and Environmental Microbiology*, Sep. 1997, pp. 3419-3425, vol. 63, No. 9.
Keeton, T.P., et al., "Effects of Midgut-Protein-Preparative and Ligand Binding Procedures on the Toxin Binding Characteristics of BT-R₁, a Common High-Affinity Receptor in *Manduca sexta* for CrylA *Bacillus thuringiensis* Toxins," *Applied and Environmental Microbiology*, Jun. 1998, pp. 2158-2165, vol. 64, No. 6.
Knight, P.J.K., et al., "The receptor of *Bacillus thuringiensis* CrlA(c) delta-endotoxin in the brush border membrane of the lepidopteran *Manduca sexta* is aminopeptidase N," *Molecular Microbiology*, 1994, pp. 429-436, vol. 11, No. 3.
Nakanishi, K., et al., "Aminopeptidase N Isoforms from the Midgut of *Bombyx mori* and *Plutella xylostella* —Their Classification and the Factors that Determine Their Binding Specificity to *Bacillus thuringiensis* CrylA Toxin," *FEBS Letters*, May 22, 2002, pp. 215-220, vol. 519, No. 1-3.

(Continued)

*Primary Examiner*—Robert B. Mondesi
(74) *Attorney, Agent, or Firm*—Alston & Bird LLP

(57) ABSTRACT

The invention relates to Bt toxin resistance management. The invention particularly relates to the isolation and characterization of nucleic acid and polypeptides for a novel Bt toxin receptor. The nucleic acid and polypeptides are useful in identifying and designing novel Bt toxin receptor ligands including novel insecticidal toxins.

3 Claims, 7 Drawing Sheets

OTHER PUBLICATIONS

Lee, M.K. et al., "Aminopeptidase N Purified from Gypsy Moth Brush Border Membrane Vesicles is a Specific Receptor for *Bacillus thuringiensis* CrylAc Toxin," *Applied and Environmental Microbiology*, Aug. 1996, pp. 2845-2849, vol. 62, No. 8.

Maaty, W.S.A., "Identification, Purification and Cloning of a High-Affinity Invertebrate Protocadherin Receptor BT-R$_2$ from the Pink Bollworm (*Pectinophora Gosspiella*) for *Bacillus Thuringiensis* CRY1A Toxins," Dissertation submitted to the Dept. of Molecular Biology and The Graduate School of the University of Wyoming, Jul. 1999, pp. 1-146.

McGaughey, W.H., et al., "Bt resistance management—A plan for reconciling the needs of the many stakeholders in Bt-based products," *Nature Biotechnology*, Feb. 1998, pp. 144-146, vol. 16.

Midboe, E.G., "Characterization of the BT-R$_1$ Gene and Its Expression in *Manduca sexta*," Dissertation submitted to the Dept. of Molecular Biology and The Graduate School of the University of Wyoming, Jul. 1999, pp. 1-135.

Nagamatsu, Y., et al., "Cloning, Sequencing, and Expression of the *Bombyx mori* Receptor for *Bacillus thuringiensis* Insecticidal CrylA(a) Toxin," *Biosci. Biotechnol. Biochem.*, 1998, pp. 727-734, vol. 62, No. 4.

Nagamatsu, Y., et al., "The cadherin-like protein is essential to specificity determination and cytotoxin action of the *Bacillus thuringiensis* insecticidal CrylAa toxin," *FEBS Letters*, 1999, pp. 385-390, vol. 460.

Oddou, P., et al., "Immunologically unrelated *heliothis* sp. And *Spodoptera* sp. Midgut membrane-proteins bind *Bacillus thuringiensis* CrylA(b) δ-endotoxin," *Eur. J. Biochem.*, 1993, pp. 145-150, vol. 212.

Roush, R.T., and Shelton, A.M., "Assessing the odds: The emergency of resistance to Bt transgenic plants," *Nature Biotechnology*, Sep. 1997, pp. 816-817, vol. 15.

Rudinger, J., "Characteristics of the amino acids as components of a peptide hormone sequence," *Peptide Hormones*, Jun. 1976, pp. 1-7, J. A. Parsons, Editor; University Park Press, Baltimore.

Skolnick, J. and Fetrow, J.S., "From genes to protein structure and function: novel applications of computational approaches in the genomic era," *Trends in Biotechnology*, 2000, pp. 34-39, vol. 18, No. 1.

Vadlamudi, R.K., et al., "A Specific Binding Protein from *manduca sexta* for the Insecticidal Toxin of *Bacillus thuringiensis* subsp. berliner," *J. Biol. Chem.*, Jun. 15, 1993, pp. 12334-12340, vol. 268, No. 17.

Vadlamudi, R.K. et al., "Cloning and Expression of a Receptor for an Insecticidal Toxin of *Bacillus thuringiensis*," *J. Biol. Chem.*, Mar. 10, 1995, pp. 5499-5494, vol. 270, No. 10.

```
              1                                                  50
AiBtR    (1)  MGVDVRILTAALVLLAASSTTSAQGMPFESRCAYMTDIPRPDERPELPPI
SfBtR    (1)  MAVDVRILTATLLVLTTATAQRDR-------CGYMVEIPRPDRP-DFPPQ
HzBtR    (1)  MAVDVRILTAAVFIIAAHLTFAQD-------CSYMVAIPRPERP-DFPSL
OnBtR    (1)  MGVERFFPAVLLVSLASAALANQR-------CSYIIAIPRPETP-ELPPI
BmBtR    (1)  MGVDVRILATLLLIYAETVLAQER-------CGFMVAIPRPPRP-DLPEL
MsBTR    (1)  MAVDVRIAAFLLVFIAPAVLAQER-------CGYMTAIPRLPRPDNLPVL
                    Signal Peptide 51                                                 100
AiBtR   (51)  IYDGLSWNERPLVPANEDRLDVCMDEFF-------RGMQYIFMEEEIHGD
SfBtR   (43)  NFDGLTWAQQPLLPAED-REEVCLNDYEPDPWSNNHGDQRIYMEEEIEGP
HzBtR   (43)  NFDGIPWSRYPLIPVEG-REDVCMNEFQ---PDALNPVTVIFMEEEIEGD
OnBtR   (43)  DYEGKSWSEQPLIPGPT-REEVCMEN-----FLPDQMIQVIYMEEEIEGD
BmBtR   (43)  DFEGQTWSQRPLIPAAD-REDVCMDGYH--AMTPTYGTQIIYMEEEIEGE
MsBTR   (44)  NFEGQTWSQRPLLPAPE-RDDLCMDAYH--VITANLGTQVIYMDEEIEDE 101                                                150
AiBtR   (94)  VPIAKLNYIGDKIPYVHSTFTVGSFRLLGPEIRKISG---DWHLVITNRQ
SfBtR   (92)  VVIAKINYQGNTPPQIRLPFRVGAAHMLGAEIREYPDATGDWYLVITQRQ
HzBtR   (89)  VAIARLNYRGTNTPTIVSPFSFGTFNMLGPVIRRIPENGGDWHLVITQRQ
OnBtR   (87)  VIIAKLNYQG--SNTPVLSIMSGQPRAQLGPEFRQNEADGQWSLVITQRQ
BmBtR   (90)  VPIAKLNYRGPNVPYIEPAFLSGSFNLLVPVIRRIPDSNGEWHLIITQRQ
MsBTR   (91)  ITIAILNYNGPSTPFIELPFLSGSYNLLMPVIRRVDN--GEWHLIITQRQ 151                                                200
AiBtR  (141)  DYEAG-TWFHAFTIRIDN-EVDAEVMLAIVNIDDNDPLIDLSEPCQIAEQ
SfBtR  (142)  DYETPDMQRYTFDVSVEGQSLVVTVRLDIVNIDDNAPIIEMLEPCNLPEL
HzBtR  (139)  DYETPGMQQYIFDVRVDDEPLVATVMLLIVNIDDNDPIIQMFEPCDIPER
OnBtR  (135)  DYETATMQSYVFSIQVEGESQAVLVALEIVNIDDNPPILQVVSACVIPEH
BmBtR  (140)  DYETPGMQQYVFNIRIDGETLVAGVSLLIVNIDDNAPIIQALEPCQVDEL
MsBTR  (139)  HYELPGMQQYMFNVRVDGQSLVAGVSLAIVNIDDNAPIIQNFEPCRVPEL 201                                                250
AiBtR  (189)  RDARSVKTCRYIVHDVDGEISTRFMRYEIESGRG-DEEVFSLVREQAPNN
SfBtR  (192)  VEPH-VTECKYIVSDADGLISTSVMSYHIDSERG-DEKVFELIRKDYPG-
HzBtR  (189)  GETG-ITSCKYTVSDADGEISTRFMRFEISSDRD-DDEYFELVRENIQG-
OnBtR  (185)  GEAR-LTDCVYQVSDRDGEISTRFMTFRVDSSRAADESIFYMVGEYDPS-
BmBtR  (190)  GEAR-LTECVYVVTDADGRISTQFMQFRIDSDRG-DDKIFYIQGANIPG-
MsBTR  (189)  GEPG-LTECTYQVSDADGRISTEFMTFRIDSVRG-DEETFYIERTNIPN- 251                                                300
AiBtR  (238)  EWMWCYMVVEVKGSLDFAQNPLHIFRAHAFDSKDNTHSVLMTVEVKNVEQ
SfBtR  (239)  DWTKVYMVLELKKSLDYEENPLHIFRVTASDSLPNNRTVVMMVEVENVEH
HzBtR  (236)  QWMYVHMRVHVKKPLDYEENPLHLFRVTAYDSLPNTHTVTMMVQVENVEN
OnBtR  (233)  DWFNMKMTVGINSPLNFETTQLHIFSVTASDSLPNNHTVTMMVQVENVES
BmBtR  (237)  EWIRMTMTVGINEPLNFETNPLHIFSVTALDSLPNTHTVTLMVQVENVEH
MsBTR  (236)  QWMWLNMTIGVNTSLNFVTSPLHIFSVTALDSLPNTHTVTMMVQVANVNS
```

FIG. 2A

```
              301                                                  350
AiBtR  (288)  RPPQWIEIFAVQQFDEKIKKSFRVRAIDADTGINKTISYRLRTAVGEENL
SfBtR  (289)  RNPRWMEIFAVQQFDEKQAKSFTVRAIDGDTGINKPIFYRIETEDEDKEF
HzBtR  (286)  RPPRWMEIFAVQQFDEKTEQSFRVRAIDGDTGIDKPIFYRIETEKGEEDL
OnBtR  (283)  RPPRWVEIFSVQQFDEKTNQSFSLRAIDGDTGINRAINYTLIR-DDADDF
BmBtR  (287)  RPPRWVEIFAVQQFDEKTAQSFPVRAIDGDTGINKPIHYRLET-AEEDTF
MsBTR  (286)  RPPRWLEIFAVQQFEEKSYQNFTVRAIDGDTEINMPINYRLIT-NEEDTF 351                                                  400
AiBtR  (338)  FELETKEGSQ-GVWLHVGPIDRDELEKEVFLLSIIAYKYGDDG----TLY
SfBtR  (339)  FSIENIGEGRDGARFHVAPIDRDYLKRDMFHIRIIAYKQGDNDKEGESSF
HzBtR  (336)  FSIQTIEGGREGAWFNVAPIDRDTLEKEVFHVSIIAYKYGDNDVEGSSSF
OnBtR  (332)  FSLEVIEDG---AILHVTEIDRDKLERELFNLTIVAYKSTD------ASF
BmBtR  (336)  FHIRTIEGGRSGAILYVDPIDRDTLQREVFQLSIIAYKYDN------ESS
MsBTR  (335)  FSIEALPGGKSGAVFLVSPIDRDTLQREVFPLTIVAYKYDE------EAF 401                                                  450
AiBtR  (383)  ETPANITIIINDVNDQLPSPLKEGGVYTIDIMEETPMTLN-LENFGFHDR
SfBtR  (389)  ETSANVTIIINDINDQRPEPFHK--EYTISIMEETAMTLD-LQEFGFHDR
HzBtR  (386)  QSKTDVVIIVNDVNDQAPLPFRE--EYSIEIMEETAMTLN-LEDFGFHDR
OnBtR  (373)  ATEAHIFIIVNDVNDQRPEPLHK--EYSIDIMEETPMTLNFNEEFGFHDR
BmBtR  (380)  ATAANVVIIVNDINDQRPEPLFK--EYRLNIMEETALTLNFDQEFGFHDR
MsBTR  (379)  STSTNVVIIVTDINDQRPEPIHK--EYRLAIMEETPLTLNFDKEFGFHDK 451                                                  500
AiBtR  (432)  DLGPNAQYNVRLESVYPDGVHEAFYIAPERGYQRQSFFLSTQNHHMLDYD
SfBtR  (436)  DIGPHAQYDVHLESIQPEGAHTAFYIAPEEGYQAQSFTIGTRIHNMLDYE
HzBtR  (433)  DLGPHAQYTVHLESIHPPRAHEAFYIAPEVGYQRQSFIMGTQNHHMLDFE
OnBtR  (421)  DLGENAQYTVELEDVFPPGAASAFYIAPGSGYQRQTFIMGTINHTMLDYE
BmBtR  (428)  DLGQNAQYTVRLESDYPADAAKAFYIAPEVGYQRQTFIMGTANHKMLDYE
MsBTR  (427)  DLGQNAQYTVRLESVDPPGAAEAFYIAPEVGYQRQTFIMGTLNHSMLDYE 501                                                  550
AiBtR  (482)  NETVDFTKIQIKAVAIDSLNNTMKGFATININLINWNDELPIFKNSVQNV
SfBtR  (486)  DDD-YRPGIKLKAVAIDRHDNNHIGEAIININLINWNDELPIFDEDAYNV
HzBtR  (483)  VP--EFQNIQLRAVAIDMDDPKWVGIAIINIKLINWNDELPMFESDVQTV
OnBtR  (471)  DV--IFQNIIIKVKAVDMNNASHVGEALVYVNLINWNDELPIFEESSYSA
BmBtR  (478)  VP--EFQRIRLRVIATDMDNEEHVGVAYVYINLINWNDEEPIFEHSVQNV
MsBTR  (477)  VP--EFQSITIRVVATDNNDTRHVGVALVHIDLINWNDEQPIFEHAVQTV 551                                                  600
AiBtR  (532)  SFPETVAAGFHVATIKAEDRDVGDRVEHSLMGNAVDFLTIDKYSGEIFVA
SfBtR  (535)  TFEETVGDGFHIGKYRAKDRDIGDIVEHSILGNAANFLRIDIDTGDVYVS
HzBtR  (531)  SFDETEGAGFYVATVVAKDRDVGDKVEHSLMGNAVSYLRIDKETGEIFVT
OnBtR  (519)  SFKETVGAGFPVATVLALDRDIDDVVHSLMGNAVDYLFIDESTGEIFVS
BmBtR  (526)  SFKETEGKGFFVANVRAHDRDIDDRVEHTLMGNANNYLSIDKDTGDIHVT
MsBTR  (525)  TFDETEGEGFFVAKAVAHDRDIGDVVEHTLLGNAVNFLTIDKLTGDIRVS
```

FIG. 2B

```
              601                                              650
AiBtR  (582)  VNNSFNYHRQNELFIQIRADDTLGEGPYHTTTSQLVIYLEDVNNTPPVLR
SfBtR  (585)  RDDYFDYQRQNEIIVQILAVDTLG-LPQNRATTQLTIFLEDINNTPPILR
HzBtR  (581)  ENEAFNYHRQNELFVQIPADDTLG-EPYNTNTTQLVIKLRDINNTPPTLR
OnBtR  (569)  MDDAFDYHRQNTLFVQVRADDTLGDGPHNTVTTQLVIELEDVNNTPPTLR
BmBtR  (576)  QDDFFDYHRQSELFVQVRADDTLG-EPFHTATSQLLIHLEDINNTPPTLR
MsBTR  (575)  ANDSFNYHRESELFVQVRATDTLG-EPFHTATSQLVIRLNDINNTPPTLR 651                                              700
AiBtR  (632)  LPRRGPHVEENVPHGHPITNDDGIQLIASDPDTTAELWFEIDWEESYATK
SfBtR  (634)  LPRSSPSVEENVEVGHPITEG--LTATDPDT--TADLHFEIDWDNSYATK
HzBtR  (630)  LPRATPSVEENVPDGFVIP----TQLHATDPDTTAELRFEIDWQNSYATK
OnBtR  (619)  LPRSTPSVEENVPEGYEIS----REITATDPDTSAYLWFEIDWDSTWATK
BmBtR  (625)  LPRGSPNVEENVPEGYIIT----SEIRATDPDTTAELRFEIDWTTSYATK
MsBTR  (624)  LPRGSPQVEENVPDGHVIT----QELRATDPDTTADLRFEINWDTSFATK 701                                              750
AiBtR  (682)  QGNE-TLKDEYRNCIEILTRYQDENRKGEAYGVLEVRQIRDDPVVTIDYE
SfBtR  (680)  QGTNGPNTADYHGCVEILTVYPDPDNHGRAEGHLVAREVSDG--VTIDYE
HzBtR  (676)  QGRN-TDSKEYIGCIEIETIYPNINQRGNAIGRVVVREIRDG--VTIDYE
OnBtR  (665)  QGRE-TNPTEYVGCIVIETIYPTEGNRGSAIGRLVVQEIRDN--VTIDFE
BmBtR  (671)  QGRE-ANPIEFHNCVEIETIYPAINNRGSAIGRLVVKKIREN--VTIDYE
MsBTR  (670)  QGRQ-ANPDEFRNCVEIETIFPEINNRGLAIGRVVAREIRHN--VTIDYE 751                                              800
AiBtR  (731)  EFEVLYLVVRVRDRNTTLGDDYDEGTLTITIIDMNDNWPTWEEGQLTQQF
SfBtR  (728)  KFEVLYLVVRVIDRNTVIGPDYDEAMLTVTIIDMNDNWPIWADNTLQQTL
HzBtR  (723)  MFEVLYLTVIVRDLNTVIGEDHDISTFTITIIDMNDNPPLWVEGTLTQEF
OnBtR  (712)  EFEMLYLTVRVRDLNTVIGDDYDEATFTITIIDMNDNAPIFANGTLTQTM
BmBtR  (718)  EFEMLYLTVRVRDLNTVIGDDYDESTFTITIIDMNDNPPIWVPGTLEQSL
MsBTR  (717)  EFEVLSLTVRVRDLNTVYGDDYDESMLTITIIDMNDNAPVWVEGTLEQNF 801                                              850
AiBtR  (781)  RVREMSLSGVVIGSLRATDRDGPLYNQVRYTIQPVDGTPADLVAIDFRTG
SfBtR  (778)  RVREMADEGVIVGTLLATDLDGPLYNRVRYTMVPIKDTPDDLIAINYVTG
HzBtR  (773)  RVREVAASGVVIGSVLATDIDGPLYNQVRYTITPRLDTPEDLVDIDFNTG
OnBtR  (762)  RVRELAASGTLIGSVLATDIDGPLYNQVRYTIQPRNNTPEGLVKIDFTTG
BmBtR  (768)  RVREMSDAGVVIGTLTATDIDGPLYNQVRYTMKANEGTPENLLMIDFYTG
MsBTR  (767)  RVREMSAGGLVVGSVRADDIDGPLYNQVRYTIFPREDTDKDLIMIDFLTG 851                                              900
AiBtR  (831)  QMTVQKNQAIDADVPPRFNLYYTVTASDKCSMEDQS-NCPDDKTYWNTTA
SfBtR  (828)  QLTVNKGQAIDADDPPRFLYYKVTASDKCSLDEFFPVCPPDPTYWNTEG
HzBtR  (823)  QISVKLHQAIDADEPPRQNLYYTVIASDKCDLLTVT-ECPPDPTYFETPG
OnBtR  (812)  QIEVDANEAIDADEPWRFLYYTVIASDECSLENRT-ECPPDSNYFEVPG
BmBtR  (818)  QITVKTSGAIDADVPRRYNLYYTVVATDRCYAEDPD-DCPDDPTYWETPG
MsBTR  (817)  QISVNTSGAIDADTPPRFHLYYTVVASDRCSTEDPA-DCPPDPTYWETEG
```

FIG. 2C

```
             901                                                      950
AiBtR   (880) KIAIQVIDTNNKVPFVEPEKFKNEVTIVEDPVTGDVTFLTSESIYEDAVS
SfBtR   (878) EIAIAITDTNNKIPRAET---------------DMFPSEKRIYENTPN
HzBtR   (872) EITIHITDTNNKVPQVE----------------DDKFEATVYIYEGADD
OnBtR   (861) DIEIEIIDTNNKVPEPL----------------TEKFNTTVYVWENATS
BmBtR   (867) QVVIQIIDTNNKIPQPE----------------TDQFKAVVYIYEDAVS
MsBTR   (866) NITIHITDTNNKVPQAE----------------TTKFDTVVYIYENATH 951                                                     1000
AiBtR   (930) GDHVFQLFVGDLDRDLPNNNVSYTINFGVNPRIRDFFEVDLVTGWVRVHY
SfBtR   (911) GTKITTIIASDQDRDRPNNALTYRINYAFNHRLENFFAVDPDTGELFVHF
HzBtR   (905) GQHVVQIYASDLDRDEIYHKVSYQINYAINSRLRDFFEMDLESGLVYVNN
OnBtR   (894) GDEVVQLYSHDRDRDELYHTVRYTMNFAVNPRLRDFFEVDLDTGRLEVHY
BmBtR   (900) GDEVVKVIGSDLDRDDIYHTIRYQINYAVNPRLRDFFAVDPDTGRVYVYY
MsBTR   (899) LDEVVTLIASDLDRDEIYHTVSYVINYAVNPRLMNFFSVNRETGLVYVDY 1001                                                    1050
AiBtR   (980) PG---PDKLDRDGDEPTHRIHFSIFDNFMSEGEPNRNQISGEALIILLDV
SfBtR   (961) TTS---EVLDRDGEEPEHRIIFTIVDNLEGAGDGNQNTISTEVRVILLDI
HzBtR   (955) TAG---ELLDRDGDEPTHRIFFNVIDNFYGEGDGNRNQNETQVLVVLLDI
OnBtR   (944) PG---DEKLDRDGDEPTHTIFVNFIDNFFSDGDGRRNQDEVEIFVVLLDV
BmBtR   (950) TT---DEVLDRDGDEPQHRIFFNLIDNFFQQGDGNRNQNDAEVLVVLLDV
MsBTR   (949) ETQGSGEVLDRDGDEPTHRIFFNLIDNFMGEGEGNRNQNDTEVLVILLDV 1051                                                    1100
AiBtR  (1027) NDNKPELPSPDSFPPWTVSESVVEGVRIPPEILAPDRDEPGTDNSRVAYD
SfBtR  (1008) NDNKPELP-IPDGEFWTVSEGEVEGKRIPPEIHAHDRDEPFNDNSRVGYE
HzBtR  (1002) NDNYPELP---ETIPWAISESLELGERVQPEIFARDRDEPGTDNSRVAYA
OnBtR   (991) NDNAPEMPL-PDELRFDVSEGAVAGVRVLPEIYAPDRDEPDTDNSRVGYG
BmBtR   (997) NDNAPELPE-PDELSWSVSESLTKGTRLQPHIYAPDRDEPDTDNSRVGYA
MsBTR   (999) NDNAPELPP-PSELSWTISENLKQGVRLEPHIFAPDRDEPDTDNSRVGYE 1101                                                    1150
AiBtR  (1077) LLGVTPER-DIEVPQLFKIETIEKDLG-INQTGILETVTPLQGYWGTYEI
SfBtR  (1057) IRSIKLINRDIELPQDPFKIITIDDLDTWKFVGELETTMDLRGYWGTYDV
HzBtR  (1049) ITGLASTDRDIQVPNLFNMITIERDRG-IDQTGILEAAMDLRGYWGTYQI
OnBtR  (1040) ILDLTITDRDIEVPDLFTMISIEN------KTGELETAMDLRGYWGTYEI
BmBtR  (1046) IISLTIANREIEVPELFTMIQIQN------VTGELETAMDLRGYWGTYAI
MsBTR  (1048) ILNLSTER-DIEVPELFVMIQIAN------VTGELETAMDLKGYWGTYAI 1151                                                    1200
AiBtR  (1125) HIKAFDHGDPRQESDEKYQLVVRPYNFHEPTFVFPLDGSAIRLSRDRAIV
SfBtR  (1107) EIRAFDHGFPMLDSFETYQLTVRPYNFHSPVFVFPTPGSTIRLSRERAIV
HzBtR  (1098) DIQAYDHGIPQRISNQKYPLVIRPYNFHDPVFVFPQPGSTIRLAKERAVV
OnBtR  (1084) FIEAFDHGYPQQRSNETYTLVIRPYNFHHPVFVFPQPDSVIRLSRERATE
BmBtR  (1090) HIKAYDHGIPQQMSNETYELVIRPYNFHAPVFVFPKHGATLRLARERAVV
MsBTR  (1091) HIRAFDHGIPQMSMNETYELIIHPFNYYAPEFVFPTNDAVIRLARERAVI
```

FIG. 2D

```
              1201                                          1250
AiBtR (1175)  SGELTVVGAAQ-APLQRISATDEDGLHAGTVSFSVVGDDEAMNYFDVWND
SfBtR (1157)  NGMLALANIASGEFLDRLSATDEDGLHAGRVTFSIAGNDEAAEYFNVLND
HzBtR (1148)  NGILATVDG---EFLDRIVATDEDGLEAGLVTFSIAGDDEDAQFFDVLND
OnBtR (1134)  GGVLATAAN---EFLEPIYATDEDGLHAGSVTFHVQGNEEAVQYFDITEV
BmBtR (1140)  NGLLATVDG---EFLNRIVATDEDGLHAGQVAFEVVGDTEAVDYFHIVND
MsBTR (1141)  NGVLATVNG---EFLERISATDPDGLHAGVVTFQVVGDEESQRYFQVVND 1251                                          1300
AiBtR (1224)  GE--NSGMLALKQALPDGFQEFKLTIRATDAGDEPGPKSTDSTVTVVFIP
SfBtR (1207)  GDN--SAMLTLKQALPAGVQQFELVIRATDGGTEPGPRSTDCSVTVVFVM
HzBtR (1195)  GVN--SGALTLTRLFPEEFREFQVTIRATDGGTEPGPRSTDCLVTVVFVP
OnBtR (1181)  GAGENSGQLILRQLFPEQIRQFRITIRATDGGTEPGPLWTDVTFSVVFVP
BmBtR (1187)  GE--NSGTLMLKQLFPEDIREFEVTIRATDGGTEPRPLSTDCTFSVVFVP
MsBTR (1188)  GE--NLGSLRLLQAVPEEIREFRITIRATDQGTDPGPLSTDMTFRVVFVP 1301                                          1350
AiBtR (1272)  Q-VEPQFPTNTQEVAFIEFEAGRSERHELTAAVDQKNILCDIDCYTVYT
SfBtR (1255)  TQGDPVFDDNAASVRFVEKEAGMSEKFQLPQADDPKNYRCMDDCHTIYYS
HzBtR (1243)  TQGEPVFEDRTYTVAFVEKDEGMLEEAELPRASDPRNIMCEDDCHDTYYS
OnBtR (1231)  TQGDPVFSENAATVAFFEGEEGLRESFELPQAEDLKNHLCEDDCQDIYYR
BmBtR (1235)  IQGEPIFPTSTHTVAFIEKEAGLLERHELPRAEDRKNHLCSDDCHNIYYR
MsBTR (1236)  TQGEPRFASSEHAVAFIEKSAGMEESHQLPLAQDIKNHLCEDDCHSIYYR 1351                                          1400
AiBtR (1321)  IIGGNAAGHFALDG--NVLYLVSELDRAQAERHTLQVAASNV-PGVTTAA
SfBtR (1305)  IVDGNDGDHFAVEPETNVIYLLKPLDRSQQEQYRVVVAASNT-PGGTSTL
HzBtR (1293)  IVGGNSGEHFTVDPRTNVLSLVKPLDRSEQETHTLIIGASDT-PNPAAVL
OnBtR (1281)  FIDGNNEGLFVLDQSSNVISLAQELDREVATSYTLHIAASNSPDATGIPL
BmBtR (1285)  IIDGNNDGHFGLDETTNVLFLVKELDRSVSETYTLTIAASNS-PTGGIAL
MsBTR (1286)  IIDGNSEGHFGLDPVRNRLFLKKELIREQSASHTLQVAASNS-PDGGIPL
                                            Cry1A Binding domain
              1401                                          1450
AiBtR (1368)  PASTLTVIVTVREANPRPHFERNLYTTGMSATDTDSERPLLTVSATHSEG
SfBtR (1354)  SSSLLTVTIGVREANPRPIFESEFYTAGVLHTDSIH-KELVYLAAKHSEG
HzBtR (1342)  QASTLTVTVNVREANPRPVFQRALYTAGISAGDFIE-RNLLTLVATHSED
OnBtR (1331)  QTSILVVTVNVREANPRPIFEQDLYTAGISTLDSIG-RELLTVRASHTED
BmBtR (1334)  TS-TITITVNVREADPQPYFVRDLYTAGISTSDSIN-RELLILQATHSEN
MsBTR (1335)  PASILTVTVTVREADPRPVFVRELYTAGISTADSIG-RELLRLHATQSEG
                             Cry1A Binding domain
              1451                                          1500
AiBtR (1418)  LPITYAIDQDSMVLDPTLEQVRESAFSMNPETGELMRMIQPNANMHGMFE
SfBtR (1403)  LPIVYSIDQETMKIDESLQTVVEDAFDINSATGVISLNFQPTSVMHGSFD
HzBtR (1391)  LPITYTLIQESMEADPTLEAVQESAFILNPETGVLSLNFQPTASMHGMFE
OnBtR (1380)  DTITYTIDRASMQLDSSLEAVRDSAFALHATTGVLSLNMQPTASMHGMFE
BmBtR (1382)  APIIYTIDWSTMVTDPTLASVRETAFILNPHTGVLTLNIQPTASMHGMFE
MsBTR (1384)  SAITYAIDYDTMVVDPSLEAVRQSAFVLNAQTGVLTLNIQPTATMHGLFK
                             Cry1A Binding domain
```

FIG. 2E

```
                    1501                                          1550
AiBtR  (1468)  FDILATDTAGATGQSHVKVYLISSRNRVYFTFYNSQESVQEHRTFIAQTF
SfBtR  (1453)  FEVVASDTRGASDRAKVSIYMISTRVRVAFLFYNTEAEVNERRNFIAQTF
HzBtR  (1441)  FEVKATDSRTETARTEVKVYLISDRNRVFFTFNNPLPEVTPQEDFIAETF
OnBtR  (1430)  FDVIATDTASAIDTARVKVYLISSQNRVTFIFDNQLETVEQNRNFIAATF
BmBtR  (1432)  FQVVATDPAGYSDRANVKIYLISTRNRVFFLFVNTLEQVEQNTDFIAQTF
MsBTR  (1434)  FEVTATDTAGAQDRTDVTVYVVSSQNRVYFVFVNTLQQVEDNRDFIADTF
               CryIA Binding domain
                    1551                                          1600
AiBtR  (1518)  TRVYSMTCNIEDIVPATD-SNGQYLTTETHVTAHFIRDDLPVDADDVQEL
SfBtR  (1503)  ANAFGMTCNIDSVLPATD-ANGVIREGYTELQAHFIRDDQPVPADYIEGL
HzBtR  (1491)  TAFFGMTCNIDQSWWASDPVTGATKDDQTEVRAHFIRDDLPVPAEEIEQL
OnBtR  (1480)  STGFNMTCNIDQVVPFSD-SSGVAQDDTTEVRAHFIRDNVPVQAQEVEAV
BmBtR  (1482)  SAGFEMTCNIDQVVPATD-ASGVIMNGITEVRGHFIRDNVPVPADEIETL
MsBTR  (1484)  SAGFNMTCNIDQVVPANDPVTGVALEHSTQMRGHFIRDNVPVLADEIEQI 1601                                          1650
AiBtR  (1567)  IEDTELFRELRTTMLGLGLQLTNVQSGLPPSVAGEDQMLAVYILAGLAGV
SfBtR  (1552)  FTELNTLRDIREVLSTQQLTLLDFAAGGSAVLPGGEYALAVYILAGIAAL
HzBtR  (1541)  RGNPTLVNSIQRALEEQNLQLADLFTGETPILGGDAQARALYALAAVAAA
OnBtR  (1529)  RSDTVLLRTIQLMLSTNSLVLQDLVTGDTPTLGEESMQIAVYALAALSAV
BmBtR  (1531)  RGDMVLLTAIQSTLATRLLVLRDLFTDTSPAP-DAGSAAVLYALAVLSAL
MsBTR  (1534)  RSDLVLLSSIQTTLAARSLVLQDLLTNSSPDS-APDSSLTVYVLASLSAV
                                                              Trans-
                    1651                                          1700
AiBtR  (1617)  LALLCIVLLITFIIRNRSLNRRIAALSATKYNSVDSNLNRIGLAAPGTNK
SfBtR  (1602)  LAVICLALLIAFFIRNRTLNRRIEALTIKDVP-TDIEPNHASVAVLNINK
HzBtR  (1591)  LALIVVVLLIVFFVRTRTLNRRLQALSMTKYSSQDSGLNRVGLAAPGTNK
OnBtR  (1579)  LGFLCLVLLLALFCRTRALNRQLQALSMTKYGSVDSGLNRAGLAP-GTNK
BmBtR  (1580)  LAALCLLLLVIFIIRTKKLNRRLEALTVKKYGSVDSGLNRVGIAAPGTNK
MsBTR  (1583)  LGFMCLVLLLTFIIRTRALNRRLEALSMTKYGSLDSGLNRAGIAAPGTNK
               membrane
                    1701                                          1750
AiBtR  (1667)  HAFE-PNPIWNETIKAPDFDAISEQSNDSDLIGIEDLPQFRNDYFPPEQE
SfBtR  (1651)  HTEPGSNPFYNPDVKTPNFDTISEVS--DDLLDVEDLEQFGKDYFPPENE
HzBtR  (1641)  HAVEGSNPIWNETLKAPDFDALSEQSYDSDLIGIEDLPQFRNDYFPPEEG
OnBtR  (1628)  HAVEGSNPMWNEAIRAPDFDAISDASGDSDLIGIEDMPQFRDDYFPPGDT
BmBtR  (1630)  HAVEGSNPIWNETIKAPDFDSMSDASNDSDLIGIEDLPHFGENNYFPRDV
MsBTR  (1633)  HTVEGSNPIFNEAIKTPDLDAISEGSNDSDLIGIEDLPHFGN---VFMDP 1751                          1795
AiBtR  (1716)  IDMNSNDIGYPEMDARNPLPNHENNFGYSNAPFNPDFTNSQSRR-
SfBtR  (1699)  IESLN--------FARNPIATHGNNFGVNSSPSNPEFSNSQFRS-
HzBtR  (1691)  SSMRG----VVNEHVPESIANHNNNFGNSTPFSSPEFANTQFRR-
OnBtR  (1678)  DSSSGIVLHMGEATDNKPVTTHGNNFGFKSTPYLPQPHPK-----
BmBtR  (1680)  DEFK-------TDKPEDIVATHNNNFGFKSTPFSSPEFANQFQK--
MsBTR  (1680)  EVNE-------KANGYPEVANHNNNFAFNPTPFSPEFVNGQFRKI
```

FIG. 2F

SEQUENCE LISTING

```
<160> NUMBER OF SEQ ID NOS: 10

<210> SEQ ID NO 1
<211> LENGTH: 5765
<212> TYPE: DNA
<213> ORGANISM: Agrotis ipsilon
<220> FEATURE:
<221> NAME/KEY: CDS
<222> LOCATION: (219)...(5498)

<400> SEQUENCE: 1
gcacgaggaa ccgatcggct tgtgctgttt taatatcaaa aaagaattca aagttttttgg        60 cttttcaagt gaaattggtg ataagtgttc atatctagtg ataccttgtt tatataagca       120
cagctaattt ccaaaaaaca gtgaagagaa cgcttaaacg aggcacaata attcatacga       180
aggtgtgccc ttgctatcgg aactcataag aacatgag atg ggt gtc gac gtc cga       236
                                         Met Gly Val Asp Val Arg
                                          1               5 atc ctg acc gca gcg ctg gtg ctg ctt gct gct tcg agt act aca tcg       284
Ile Leu Thr Ala Ala Leu Val Leu Leu Ala Ala Ser Ser Thr Thr Ser
             10                  15                  20 gca caa ggt atg ccc ttt gaa tcc cga tgt gct tac atg acg gat att       332
Ala Gln Gly Met Pro Phe Glu Ser Arg Cys Ala Tyr Met Thr Asp Ile
         25                  30                  35 cca agg cca gac gaa aga cct gaa tta cca cct ata att tat gat gga       380
Pro Arg Pro Asp Glu Arg Pro Glu Leu Pro Pro Ile Ile Tyr Asp Gly
     40                  45                  50 ctg tca tgg aac gaa cga cca ctg gtg cct gcc aac gag gat agg ctt       428
Leu Ser Trp Asn Glu Arg Pro Leu Val Pro Ala Asn Glu Asp Arg Leu
 55                  60                  65                  70 gac gta tgc atg gat gag ttt ttc cgt ggt atg cag tat atc ttc atg       476
Asp Val Cys Met Asp Glu Phe Phe Arg Gly Met Gln Tyr Ile Phe Met
                 75                  80                  85 gag gaa gag atc cat ggc gac gta ccc atc gcc aag tta aac tac ata       524
Glu Glu Glu Ile His Gly Asp Val Pro Ile Ala Lys Leu Asn Tyr Ile
             90                  95                 100 ggt gac aaa att cct tac gta cat tct acc ttt acc gtt ggg tca ttc       572
Gly Asp Lys Ile Pro Tyr Val His Ser Thr Phe Thr Val Gly Ser Phe
        105                 110                 115 aga ttg ctt ggt cca gaa ata cgt aaa ata agt gga gac tgg cac ctc       620
Arg Leu Leu Gly Pro Glu Ile Arg Lys Ile Ser Gly Asp Trp His Leu
    120                 125                 130 gtt ata acg aac agg cag gat tac gag gcc ggg acg tgg ttt cat gcg       668
Val Ile Thr Asn Arg Gln Asp Tyr Glu Ala Gly Thr Trp Phe His Ala
135                 140                 145                 150 ttc aca ata aga ata gat aac gag gtc gac gct gag gtg atg ctc gcg       716
Phe Thr Ile Arg Ile Asp Asn Glu Val Asp Ala Glu Val Met Leu Ala
                155                 160                 165
```

-continued

| | | |
|---|---|---|
| atc gtc aac atc gac gac aac gat ccc ctt atc gat ttg tca gaa cct<br>Ile Val Asn Ile Asp Asp Asn Asp Pro Leu Ile Asp Leu Ser Glu Pro<br>170 175 180 | | 764 |
| tgt cag ata gct gaa caa aga gat gct aga agt gtg aag act tgt agg<br>Cys Gln Ile Ala Glu Gln Arg Asp Ala Arg Ser Val Lys Thr Cys Arg<br>185 190 195 | | 812 |
| tac ata gtg cat gac gtt gac gga gag atc agt acg aga ttt atg cgc<br>Tyr Ile Val His Asp Val Asp Gly Glu Ile Ser Thr Arg Phe Met Arg<br>200 205 210 | | 860 |
| tac gaa att gaa agt ggt cga gga gac gaa gaa gtc ttc agt ttg gtc<br>Tyr Glu Ile Glu Ser Gly Arg Gly Asp Glu Glu Val Phe Ser Leu Val<br>215 220 225 230 | | 908 |
| aga gag caa gcc ccg aat aac gaa tgg atg tgg tgt tac atg gtg gtg<br>Arg Glu Gln Ala Pro Asn Asn Glu Trp Met Trp Cys Tyr Met Val Val<br>235 240 245 | | 956 |
| gaa gtt aaa gga tcc ctc gac ttt gcg cag aac cca ctt cat ata ttc<br>Glu Val Lys Gly Ser Leu Asp Phe Ala Gln Asn Pro Leu His Ile Phe<br>250 255 260 | | 1004 |
| cga gcc cat gct ttt gat tcg aaa gat aat acg cac agc gta tta atg<br>Arg Ala His Ala Phe Asp Ser Lys Asp Asn Thr His Ser Val Leu Met<br>265 270 275 | | 1052 |
| acg gtc gaa gta aag aac gtg gaa cag aga ccg ccg caa tgg att gag<br>Thr Val Glu Val Lys Asn Val Glu Gln Arg Pro Pro Gln Trp Ile Glu<br>280 285 290 | | 1100 |
| atc ttc gcc gtg cag caa ttc gac gag aag atc aag aaa tcg ttc aga<br>Ile Phe Ala Val Gln Gln Phe Asp Glu Lys Ile Lys Lys Ser Phe Arg<br>295 300 305 310 | | 1148 |
| gta agg gct ata gat gct gac acg gga att aat aag aca ata agc tat<br>Val Arg Ala Ile Asp Ala Asp Thr Gly Ile Asn Lys Thr Ile Ser Tyr<br>315 320 325 | | 1196 |
| cgg cta cga act gct gtg gga gaa gaa aat tta ttt gaa ctt gaa acg<br>Arg Leu Arg Thr Ala Val Gly Glu Glu Asn Leu Phe Glu Leu Glu Thr<br>330 335 340 | | 1244 |
| aaa gaa ggg agt caa ggt gta tgg ctt cat gtt ggg cct ata gac aga<br>Lys Glu Gly Ser Gln Gly Val Trp Leu His Val Gly Pro Ile Asp Arg<br>345 350 355 | | 1292 |
| gat gaa ctc gaa aaa gaa gtg ttc ttg ttg tct ata ata gca tac aag<br>Asp Glu Leu Glu Lys Glu Val Phe Leu Leu Ser Ile Ile Ala Tyr Lys<br>360 365 370 | | 1340 |
| tac ggt gac gat ggt aca ttg tac gag acg cct gcc aac atc act att<br>Tyr Gly Asp Asp Gly Thr Leu Tyr Glu Thr Pro Ala Asn Ile Thr Ile<br>375 380 385 390 | | 1388 |
| ata atc aac gat gtc aat gac cag cta cca agt cct ctc aaa gaa ggc<br>Ile Ile Asn Asp Val Asn Asp Gln Leu Pro Ser Pro Leu Lys Glu Gly<br>395 400 405 | | 1436 |
| ggt gta tac act att gac atc atg gag gag act ccc atg act ctc aat<br>Gly Val Tyr Thr Ile Asp Ile Met Glu Glu Thr Pro Met Thr Leu Asn<br>410 415 420 | | 1484 |
| tta gaa aac ttc ggt ttt cat gat cgt gat cta gga cca aac gca caa<br>Leu Glu Asn Phe Gly Phe His Asp Arg Asp Leu Gly Pro Asn Ala Gln<br>425 430 435 | | 1532 |
| tat aat gtg cgc ttg gaa agt gtt tat cca gac gga gtt cat gag gca<br>Tyr Asn Val Arg Leu Glu Ser Val Tyr Pro Asp Gly Val His Glu Ala<br>440 445 450 | | 1580 |
| ttc tat atc gcc cca gaa cgt ggc tac cag cgg cag tcc ttc ttt ttg<br>Phe Tyr Ile Ala Pro Glu Arg Gly Tyr Gln Arg Gln Ser Phe Phe Leu<br>455 460 465 470 | | 1628 |
| agc aca cag aac cat cac atg ctt gat tat gac aac gaa aca gtt gat<br>Ser Thr Gln Asn His His Met Leu Asp Tyr Asp Asn Glu Thr Val Asp<br>475 480 485 | | 1676 |

-continued

| | |
|---|---|
| ttt acg aaa att caa ata aag gcg gtg gca ata gac tcg ctt aac aat<br>Phe Thr Lys Ile Gln Ile Lys Ala Val Ala Ile Asp Ser Leu Asn Asn<br>490                          495                       500 | 1724 |
| acc atg aaa gga ttc gca acg atc aac att aac ctg att aac tgg aac<br>Thr Met Lys Gly Phe Ala Thr Ile Asn Ile Asn Leu Ile Asn Trp Asn<br>505                          510                       515 | 1772 |
| gac gag ctg ccg atc ttc aag aat tct gtg cag aac gtc tcg ttc ccc<br>Asp Glu Leu Pro Ile Phe Lys Asn Ser Val Gln Asn Val Ser Phe Pro<br>520                          525                       530 | 1820 |
| gag acg gtg gcg gcc ggc ttt cac gta gcg acc ata aag gct gaa gac<br>Glu Thr Val Ala Ala Gly Phe His Val Ala Thr Ile Lys Ala Glu Asp<br>535                       540                     545                550 | 1868 |
| agg gat gta ggc gat aga gtt gag cat tcg ctg atg ggc aac gct gtc<br>Arg Asp Val Gly Asp Arg Val Glu His Ser Leu Met Gly Asn Ala Val<br>555                       560                     565 | 1916 |
| gat ttt ctg act att gat aaa tac agc ggc gaa atc ttc gtg gca gtc<br>Asp Phe Leu Thr Ile Asp Lys Tyr Ser Gly Glu Ile Phe Val Ala Val<br>570                       575                     580 | 1964 |
| aat aat tct ttc aac tat cac agg cag aac gag ctg ttt ata cag att<br>Asn Asn Ser Phe Asn Tyr His Arg Gln Asn Glu Leu Phe Ile Gln Ile<br>585                       590                     595 | 2012 |
| aga gcc gat gac acg cta ggc gaa ggc cct tac cac acc acc acc tcc<br>Arg Ala Asp Asp Thr Leu Gly Glu Gly Pro Tyr His Thr Thr Thr Ser<br>600                       605                     610 | 2060 |
| cag ctg gtt ata tat cta gag gac gtc aac aat aca cct ccc gtc ctc<br>Gln Leu Val Ile Tyr Leu Glu Asp Val Asn Asn Thr Pro Pro Val Leu<br>615                       620                     625                630 | 2108 |
| aga ctt cct cgc agg ggt ccg cat gtg gaa gag aac gtt ccg cat ggg<br>Arg Leu Pro Arg Arg Gly Pro His Val Glu Glu Asn Val Pro His Gly<br>635                       640                     645 | 2156 |
| cac ccg atc acc aat gat gac ggg atc caa ttg atc gcc tct gac ccc<br>His Pro Ile Thr Asn Asp Asp Gly Ile Gln Leu Ile Ala Ser Asp Pro<br>650                         655                     660 | 2204 |
| gac acc acg gct gaa ctc tgg ttc gag atc gac tgg gag gaa tcc tat<br>Asp Thr Thr Ala Glu Leu Trp Phe Glu Ile Asp Trp Glu Glu Ser Tyr<br>665                       670                     675 | 2252 |
| gcc acc aag cag ggc aac gag aca ctc aaa gac gag tac cga aat tgc<br>Ala Thr Lys Gln Gly Asn Glu Thr Leu Lys Asp Glu Tyr Arg Asn Cys<br>680                       685                     690 | 2300 |
| ata gaa att ttg aca cga tac cag gac gaa aac agg aaa ggc gaa gca<br>Ile Glu Ile Leu Thr Arg Tyr Gln Asp Glu Asn Arg Lys Gly Glu Ala<br>695                       700                     705                710 | 2348 |
| tac ggg gtc ttg gag gtg cga cag atc agg gac gac cca gtt gtg acc<br>Tyr Gly Val Leu Glu Val Arg Gln Ile Arg Asp Asp Pro Val Val Thr<br>715                       720                     725 | 2396 |
| att gac tac gag gag ttc gag gtg ctg tat ctc gtc gtc agg gtc agg<br>Ile Asp Tyr Glu Glu Phe Glu Val Leu Tyr Leu Val Val Arg Val Arg<br>730                       735                     740 | 2444 |
| gat agg aac acc aca ctc gga gac gac tat gac gaa ggc aca ttg acg<br>Asp Arg Asn Thr Thr Leu Gly Asp Asp Tyr Asp Glu Gly Thr Leu Thr<br>745                       750                     755 | 2492 |
| atc acg atc ata gat atg aat gac aac tgg cca acc tgg gag gag ggg<br>Ile Thr Ile Ile Asp Met Asn Asp Asn Trp Pro Thr Trp Glu Glu Gly<br>760                       765                     770 | 2540 |
| cag ctg acg caa cag ttc cgc gtt cga gag atg tca ctc agc ggc gtc<br>Gln Leu Thr Gln Gln Phe Arg Val Arg Glu Met Ser Leu Ser Gly Val<br>775                       780                     785                790 | 2588 |
| gtt atc ggc tcc ttg cgc gcc acc gac agg gac ggc ccg ctc tac aac<br>Val Ile Gly Ser Leu Arg Ala Thr Asp Arg Asp Gly Pro Leu Tyr Asn | 2636 |

-continued

|  |  |
|---|---|
| 795 800 805<br>caa gtg cgc tac acc atc caa cca gta gac ggg act cca gcg gat cta<br>Gln Val Arg Tyr Thr Ile Gln Pro Val Asp Gly Thr Pro Ala Asp Leu<br>            810                     815                  820 | 2684 |
| gtt gca att gac ttc agg act ggc cag atg acg gtt cag aag aac caa<br>Val Ala Ile Asp Phe Arg Thr Gly Gln Met Thr Val Gln Lys Asn Gln<br>        825                        830                     835 | 2732 |
| gct ata gac gca gac gtg cca cca aga ttt aac ttg tac tac acc gtc<br>Ala Ile Asp Ala Asp Val Pro Pro Arg Phe Asn Leu Tyr Tyr Thr Val<br>840                     845                     850 | 2780 |
| aca gcc agc gac aaa tgt tct atg gaa gac cag tcg aac tgt ccg gat<br>Thr Ala Ser Asp Lys Cys Ser Met Glu Asp Gln Ser Asn Cys Pro Asp<br>855                     860                     865                     870 | 2828 |
| gat aaa act tat tgg aat aca act gca aaa ata gcg atc cag gta atc<br>Asp Lys Thr Tyr Trp Asn Thr Thr Ala Lys Ile Ala Ile Gln Val Ile<br>                     875                     880                     885 | 2876 |
| gac aca aac aac aag gtg cct ttc gtg gag ccc gaa aag ttc aaa aat<br>Asp Thr Asn Asn Lys Val Pro Phe Val Glu Pro Glu Lys Phe Lys Asn<br>                       890                     895                     900 | 2924 |
| gaa gtg act atc gtc gag gat cca gtt act ggt gac gtc aca ttc ctg<br>Glu Val Thr Ile Val Glu Asp Pro Val Thr Gly Asp Val Thr Phe Leu<br>                  905                     910                     915 | 2972 |
| acc agt gag agc atc tac gag gac gca gtc agc ggg gac cac gtc ttc<br>Thr Ser Glu Ser Ile Tyr Glu Asp Ala Val Ser Gly Asp His Val Phe<br>920                     925                     930 | 3020 |
| cag ctc ttt gtc ggc gac ttg gat aga gat ctg ccg aat aac aac gtg<br>Gln Leu Phe Val Gly Asp Leu Asp Arg Asp Leu Pro Asn Asn Asn Val<br>935                     940                     945                     950 | 3068 |
| agt tac acg atc aac ttc gga gtg aac cct cgc att cga gac ttc ttc<br>Ser Tyr Thr Ile Asn Phe Gly Val Asn Pro Arg Ile Arg Asp Phe Phe<br>                     955                     960                     965 | 3116 |
| gag gta gac ctt gtg act ggc tgg gtg cgg gtg cac tac ccc ggg ccc<br>Glu Val Asp Leu Val Thr Gly Trp Val Arg Val His Tyr Pro Gly Pro<br>                  970                     975                     980 | 3164 |
| gac aag ctc gac cgg gac ggc gac gag ccc acg cac cgg atc cac ttc<br>Asp Lys Leu Asp Arg Asp Gly Asp Glu Pro Thr His Arg Ile His Phe<br>                  985                     990                     995 | 3212 |
| agc atc ttc gat aac ttc atg agc gaa gga gag ccc aat cgc aac cag<br>Ser Ile Phe Asp Asn Phe Met Ser Glu Gly Glu Pro Asn Arg Asn Gln<br>1000                   1005                  1010 | 3260 |
| atc agc ggg gaa gct ctt ata att tta ctt gat gtg aac gac aac aag<br>Ile Ser Gly Glu Ala Leu Ile Ile Leu Leu Asp Val Asn Asp Asn Lys<br>1015                   1020                  1025                  1030 | 3308 |
| ccc gag ctg cct tca ccg gac agc ttc ccc ccg tgg acc gtc tct gaa<br>Pro Glu Leu Pro Ser Pro Asp Ser Phe Pro Pro Trp Thr Val Ser Glu<br>                  1035                  1040                  1045 | 3356 |
| agt gta gtc gag ggc gtc cgg ata cca cca gaa atc tta gca ccc gac<br>Ser Val Val Glu Gly Val Arg Ile Pro Pro Glu Ile Leu Ala Pro Asp<br>                  1050                  1055                  1060 | 3404 |
| cgg gat gaa cca gga acg gac aac tcc cga gtg gcg tac gac ctc ctg<br>Arg Asp Glu Pro Gly Thr Asp Asn Ser Arg Val Ala Tyr Asp Leu Leu<br>                  1065                  1070                  1075 | 3452 |
| gga gtt acc ccg gag aga gac atc gaa gta ccc cag ctc ttc aaa atc<br>Gly Val Thr Pro Glu Arg Asp Ile Glu Val Pro Gln Leu Phe Lys Ile<br>                  1080                  1085                  1090 | 3500 |
| gag acc ata gag aaa gat ctc gga ata aac cag act ggg ata cta gaa<br>Glu Thr Ile Glu Lys Asp Leu Gly Ile Asn Gln Thr Gly Ile Leu Glu<br>1095                   1100                  1105                  1110 | 3548 |
| act gtc acg cca tta caa ggg tat tgg ggt acc tat gag att cac ata | 3596 |

```
                Thr Val Thr Pro Leu Gln Gly Tyr Trp Gly Thr Tyr Glu Ile His Ile
                                1115                1120                1125 aag gca ttt gat cac gga gac cca cgt caa gag tct gac gag aag tac        3644
Lys Ala Phe Asp His Gly Asp Pro Arg Gln Glu Ser Asp Glu Lys Tyr
        1130                1135                1140 cag tta gtg gtc aga ccc tac aac ttc cac gaa ccc acg ttt gta ttt        3692
Gln Leu Val Val Arg Pro Tyr Asn Phe His Glu Pro Thr Phe Val Phe
        1145                1150                1155 cca tta gat gga tct gcc atc aga cta tcg agg gac cgc gcg atc gtg        3740
Pro Leu Asp Gly Ser Ala Ile Arg Leu Ser Arg Asp Arg Ala Ile Val
        1160                1165                1170 agt ggg gag ctg acg gta gtc ggc gct gcg cag gcg ccg ctt cag cgc        3788
Ser Gly Glu Leu Thr Val Val Gly Ala Ala Gln Ala Pro Leu Gln Arg
1175                1180                1185                1190 atc tct gcc act gat gaa gac ggg ctc cac gct gga acc gtc agt ttc        3836
Ile Ser Ala Thr Asp Glu Asp Gly Leu His Ala Gly Thr Val Ser Phe
            1195                1200                1205 tca gta gtg ggt gat gac gag gcg atg aat tac ttc gac gtg tgg aac        3884
Ser Val Val Gly Asp Asp Glu Ala Met Asn Tyr Phe Asp Val Trp Asn
            1210                1215                1220 gac gga gag aac tct ggc atg ctg gcc ctc aag cag gcc ttg ccg gac        3932
Asp Gly Glu Asn Ser Gly Met Leu Ala Leu Lys Gln Ala Leu Pro Asp
        1225                1230                1235 ggc ttc caa gag ttc aag ctg acg atc cga gca aca gat gcc ggc gac        3980
Gly Phe Gln Glu Phe Lys Leu Thr Ile Arg Ala Thr Asp Ala Gly Asp
        1240                1245                1250 gag ccc ggc ccc aag agc acc gac agc acc gtc aca gtg gtg ttc ata        4028
Glu Pro Gly Pro Lys Ser Thr Asp Ser Thr Val Thr Val Val Phe Ile
1255                1260                1265                1270 cca caa gta gag ccc cag ttc ccc acc aac act caa gaa gtt gct ttt        4076
Pro Gln Val Glu Pro Gln Phe Pro Thr Asn Thr Gln Glu Val Ala Phe
            1275                1280                1285 att gag ttt gaa gca ggc cgg tcg gag cga cac gag ctg acg gcc gcc        4124
Ile Glu Phe Glu Ala Gly Arg Ser Glu Arg His Glu Leu Thr Ala Ala
            1290                1295                1300 gta gac cag aag aac atc ctc tgt gat att gat tgc tac act gtc tac        4172
Val Asp Gln Lys Asn Ile Leu Cys Asp Ile Asp Cys Tyr Thr Val Tyr
        1305                1310                1315 tac acc atc att ggt ggt aac gcg gcg gga cac ttc gca ctg gac ggc        4220
Tyr Thr Ile Ile Gly Gly Asn Ala Ala Gly His Phe Ala Leu Asp Gly
        1320                1325                1330 aac gtg ctg tac ctg gtg tcg gag ctg gac cgc gcg cag gcc gag cgg        4268
Asn Val Leu Tyr Leu Val Ser Glu Leu Asp Arg Ala Gln Ala Glu Arg
1335                1340                1345                1350 cac acg ctg cag gtg gcc gcc agc aac gtg ccc ggc gtc acc acc gcc        4316
His Thr Leu Gln Val Ala Ala Ser Asn Val Pro Gly Val Thr Thr Ala
            1355                1360                1365 gcg ccc gcc tcc aca ctc acc gtc atc gtc act gtc cgg gaa gcg aat        4364
Ala Pro Ala Ser Thr Leu Thr Val Ile Val Thr Val Arg Glu Ala Asn
        1370                1375                1380 cct cgg ccg cac ttc gag aga aac ctg tat acc acc gga atg tcc gcc        4412
Pro Arg Pro His Phe Glu Arg Asn Leu Tyr Thr Thr Gly Met Ser Ala
        1385                1390                1395 aca gac aca gac agc gag aga cct ctc ctc aca gta tcg gcg aca cac        4460
Thr Asp Thr Asp Ser Glu Arg Pro Leu Leu Thr Val Ser Ala Thr His
        1400                1405                1410 tcg gaa ggc cta cct atc acg tac gcg ata gac cag gac tcc atg gta        4508
Ser Glu Gly Leu Pro Ile Thr Tyr Ala Ile Asp Gln Asp Ser Met Val
1415                1420                1425                1430
```

```
                                                    -continued ctg gac cca acg ctg gaa cag gtc cgg gaa agt gcc ttc tcg atg aac      4556
Leu Asp Pro Thr Leu Glu Gln Val Arg Glu Ser Ala Phe Ser Met Asn
            1435                1440                1445 cct gag acc gga gag ttg atg agg atg atc cag ccc aat gcc aat atg      4604
Pro Glu Thr Gly Glu Leu Met Arg Met Ile Gln Pro Asn Ala Asn Met
        1450                1455                1460 cat ggc atg ttc gag ttt gat atc ctg gct act gat aca gct gga gcg      4652
His Gly Met Phe Glu Phe Asp Ile Leu Ala Thr Asp Thr Ala Gly Ala
    1465                1470                1475 acg ggc cag tct cac gtg aag gtg tac ctg att tca tcc cgc aac aga      4700
Thr Gly Gln Ser His Val Lys Val Tyr Leu Ile Ser Ser Arg Asn Arg
1480                1485                1490 gtc tac ttc acc ttc tac aac tca cag gag tcg gtc cag gaa cat agg      4748
Val Tyr Phe Thr Phe Tyr Asn Ser Gln Glu Ser Val Gln Glu His Arg
1495                1500                1505                1510 acc ttt ata gcc cag aca ttc acc cgt gta tac agt atg acg tgc aac      4796
Thr Phe Ile Ala Gln Thr Phe Thr Arg Val Tyr Ser Met Thr Cys Asn
            1515                1520                1525 atc gag gac atc gtg ccc gcc acc gac tcc aac ggc caa tat ctg act      4844
Ile Glu Asp Ile Val Pro Ala Thr Asp Ser Asn Gly Gln Tyr Leu Thr
        1530                1535                1540 acc gaa act cat gtc acg gcg cat ttc ata cgt gac gac ttg cct gta      4892
Thr Glu Thr His Val Thr Ala His Phe Ile Arg Asp Asp Leu Pro Val
    1545                1550                1555 gac gct gat gat gtc cag gaa tta atc gag gac acg gag ttg ttt cgc      4940
Asp Ala Asp Asp Val Gln Glu Leu Ile Glu Asp Thr Glu Leu Phe Arg
1560                1565                1570 gaa ctc aga aca act atg ctt ggt ctg ggc ctg caa ctc acg aac gtg      4988
Glu Leu Arg Thr Thr Met Leu Gly Leu Gly Leu Gln Leu Thr Asn Val
1575                1580                1585                1590 cag tcg gga ctg ccg ccg tcg gtg gcc ggc gaa gac cag atg ctg gcc      5036
Gln Ser Gly Leu Pro Pro Ser Val Ala Gly Glu Asp Gln Met Leu Ala
            1595                1600                1605 gtg tac ata ctg gcc gga ctg gct ggc gtg ctg gcc ctg ctg tgc atc      5084
Val Tyr Ile Leu Ala Gly Leu Ala Gly Val Leu Ala Leu Leu Cys Ile
        1610                1615                1620 gtg ctg ctc atc act ttc atc atc agg aac cgc tcg cta aac cga cgc      5132
Val Leu Leu Ile Thr Phe Ile Ile Arg Asn Arg Ser Leu Asn Arg Arg
    1625                1630                1635 att gcc gcg cta tcg gcg aca aag tac aac tcg gtg gac tcg aac ctc      5180
Ile Ala Ala Leu Ser Ala Thr Lys Tyr Asn Ser Val Asp Ser Asn Leu
1640                1645                1650 aac cgc att ggt ctg gcc gca ccc ggc acc aac aaa cac gcc ttc gag      5228
Asn Arg Ile Gly Leu Ala Ala Pro Gly Thr Asn Lys His Ala Phe Glu
1655                1660                1665                1670 ccc aac ccc ata tgg aac gaa act att aaa gca cca gac ttt gac gct      5276
Pro Asn Pro Ile Trp Asn Glu Thr Ile Lys Ala Pro Asp Phe Asp Ala
            1675                1680                1685 att agt gag cag tcc aat gat tcg gat ctg att ggc ata gaa gac ctt      5324
Ile Ser Glu Gln Ser Asn Asp Ser Asp Leu Ile Gly Ile Glu Asp Leu
        1690                1695                1700 cct caa ttc agg aac gac tac ttt ccg cca gaa caa gag att gac atg      5372
Pro Gln Phe Arg Asn Asp Tyr Phe Pro Pro Glu Gln Glu Ile Asp Met
    1705                1710                1715 aat agc aac gat att gga tac cct gaa atg gat gcc cgc aac cca cta      5420
Asn Ser Asn Asp Ile Gly Tyr Pro Glu Met Asp Ala Arg Asn Pro Leu
1720                1725                1730 ccc aac cat gag aac aac ttt ggg tac agc aac gct ccc ttc aat cct      5468
Pro Asn His Glu Asn Asn Phe Gly Tyr Ser Asn Ala Pro Phe Asn Pro
1735                1740                1745                1750
```

```
gat ttc act aat tca cag tca cgg aga taa gaagtaatag cttataaaca    5518
Asp Phe Thr Asn Ser Gln Ser Arg Arg *
                        1755 gtgttctttt tttttaaata aagttaagaa tacacgccac tcctgtaatc ccagaagtta    5578 ggggtatgcc tcattatgcc tctcacattt tgaaacgcat gagtattaaa gttattatat    5638 ttttttttc aacatatcaa taagtacaac acaaatgtaa agatactcgt attattaaat     5698 aagtgaaaat aataattatt gttgaaaaaa aagtattgct tcatttaaaa aaaaaaaaa    5758 aaaaaaa    5765

<210> SEQ ID NO 2
<211> LENGTH: 1759
<212> TYPE: PRT
<213> ORGANISM: Agrotis ipsilon

<400> SEQUENCE: 2

Met Gly Val Asp Val Arg Ile Leu Thr Ala Ala Leu Val Leu Leu Ala
  1               5                  10                  15

Ala Ser Ser Thr Thr Ser Ala Gln Gly Met Pro Phe Glu Ser Arg Cys
             20                  25                  30

Ala Tyr Met Thr Asp Ile Pro Arg Pro Asp Glu Arg Pro Glu Leu Pro
         35                  40                  45

Pro Ile Ile Tyr Asp Gly Leu Ser Trp Asn Glu Arg Pro Leu Val Pro
     50                  55                  60

Ala Asn Glu Asp Arg Leu Asp Val Cys Met Asp Glu Phe Phe Arg Gly
 65                  70                  75                  80

Met Gln Tyr Ile Phe Met Glu Glu Glu Ile His Gly Asp Val Pro Ile
                 85                  90                  95

Ala Lys Leu Asn Tyr Ile Gly Asp Lys Ile Pro Tyr Val His Ser Thr
            100                 105                 110

Phe Thr Val Gly Ser Phe Arg Leu Leu Gly Pro Glu Ile Arg Lys Ile
        115                 120                 125

Ser Gly Asp Trp His Leu Val Ile Thr Asn Arg Gln Asp Tyr Glu Ala
    130                 135                 140

Gly Thr Trp Phe His Ala Phe Thr Ile Arg Ile Asp Asn Glu Val Asp
145                 150                 155                 160

Ala Glu Val Met Leu Ala Ile Val Asn Ile Asp Asp Asn Asp Pro Leu
                165                 170                 175

Ile Asp Leu Ser Glu Pro Cys Gln Ile Ala Glu Gln Arg Asp Ala Arg
            180                 185                 190

Ser Val Lys Thr Cys Arg Tyr Ile Val His Asp Val Asp Gly Glu Ile
        195                 200                 205

Ser Thr Arg Phe Met Arg Tyr Glu Ile Glu Ser Gly Arg Gly Asp Glu
    210                 215                 220

Glu Val Phe Ser Leu Val Arg Glu Gln Ala Pro Asn Asn Glu Trp Met
225                 230                 235                 240

Trp Cys Tyr Met Val Glu Val Lys Gly Ser Leu Asp Phe Ala Gln
                245                 250                 255

Asn Pro Leu His Ile Phe Arg Ala His Ala Phe Asp Ser Lys Asp Asn
            260                 265                 270

Thr His Ser Val Leu Met Thr Val Glu Val Lys Asn Val Glu Gln Arg
        275                 280                 285

Pro Pro Gln Trp Ile Glu Ile Phe Ala Val Gln Gln Phe Asp Glu Lys
    290                 295                 300
```

-continued

```
Ile Lys Lys Ser Phe Arg Val Arg Ala Ile Asp Ala Asp Thr Gly Ile
305                 310                 315                 320

Asn Lys Thr Ile Ser Tyr Arg Leu Arg Thr Ala Val Gly Glu Glu Asn
                325                 330                 335

Leu Phe Glu Leu Glu Thr Lys Glu Gly Ser Gln Gly Val Trp Leu His
            340                 345                 350

Val Gly Pro Ile Asp Arg Asp Glu Leu Glu Lys Glu Val Phe Leu Leu
        355                 360                 365

Ser Ile Ile Ala Tyr Lys Tyr Gly Asp Asp Gly Thr Leu Tyr Glu Thr
370                 375                 380

Pro Ala Asn Ile Thr Ile Ile Asn Asp Val Asn Asp Gln Leu Pro
385                 390                 395                 400

Ser Pro Leu Lys Glu Gly Gly Val Tyr Thr Ile Asp Ile Met Glu Glu
                405                 410                 415

Thr Pro Met Thr Leu Asn Leu Glu Asn Phe Gly Phe His Asp Arg Asp
            420                 425                 430

Leu Gly Pro Asn Ala Gln Tyr Asn Val Arg Leu Glu Ser Val Tyr Pro
        435                 440                 445

Asp Gly Val His Glu Ala Phe Tyr Ile Ala Pro Glu Arg Gly Tyr Gln
    450                 455                 460

Arg Gln Ser Phe Phe Leu Ser Thr Gln Asn His Met Leu Asp Tyr
465                 470                 475                 480

Asp Asn Glu Thr Val Asp Phe Thr Lys Ile Gln Ile Lys Ala Val Ala
                485                 490                 495

Ile Asp Ser Leu Asn Asn Thr Met Lys Gly Phe Ala Thr Ile Asn Ile
            500                 505                 510

Asn Leu Ile Asn Trp Asn Asp Glu Leu Pro Ile Phe Lys Asn Ser Val
        515                 520                 525

Gln Asn Val Ser Phe Pro Glu Thr Val Ala Ala Gly Phe His Val Ala
    530                 535                 540

Thr Ile Lys Ala Glu Asp Arg Asp Val Gly Asp Arg Val Glu His Ser
545                 550                 555                 560

Leu Met Gly Asn Ala Val Asp Phe Leu Thr Ile Asp Lys Tyr Ser Gly
                565                 570                 575

Glu Ile Phe Val Ala Val Asn Asn Ser Phe Asn Tyr His Arg Gln Asn
            580                 585                 590

Glu Leu Phe Ile Gln Ile Arg Ala Asp Asp Thr Leu Gly Glu Gly Pro
        595                 600                 605

Tyr His Thr Thr Thr Ser Gln Leu Val Ile Tyr Leu Glu Asp Val Asn
    610                 615                 620

Asn Thr Pro Pro Val Leu Arg Leu Pro Arg Arg Gly Pro His Val Glu
625                 630                 635                 640

Glu Asn Val Pro His Gly His Pro Ile Thr Asn Asp Asp Gly Ile Gln
                645                 650                 655

Leu Ile Ala Ser Asp Pro Asp Thr Thr Ala Glu Leu Trp Phe Glu Ile
            660                 665                 670

Asp Trp Glu Glu Ser Tyr Ala Thr Lys Gln Gly Asn Glu Thr Leu Lys
        675                 680                 685

Asp Glu Tyr Arg Asn Cys Ile Glu Ile Leu Thr Arg Tyr Gln Asp Glu
    690                 695                 700

Asn Arg Lys Gly Glu Ala Tyr Gly Val Leu Glu Val Arg Gln Ile Arg
705                 710                 715                 720
```

-continued

Asp Asp Pro Val Val Thr Ile Asp Tyr Glu Glu Phe Glu Val Leu Tyr
                725                 730                 735

Leu Val Val Arg Val Arg Asp Arg Asn Thr Thr Leu Gly Asp Asp Tyr
                740                 745                 750

Asp Glu Gly Thr Leu Thr Ile Thr Ile Ile Asp Met Asn Asp Asn Trp
                755                 760                 765

Pro Thr Trp Glu Glu Gly Gln Leu Thr Gln Gln Phe Arg Val Arg Glu
770                 775                 780

Met Ser Leu Ser Gly Val Val Ile Gly Ser Leu Arg Ala Thr Asp Arg
785                 790                 795                 800

Asp Gly Pro Leu Tyr Asn Gln Val Arg Tyr Thr Ile Gln Pro Val Asp
                805                 810                 815

Gly Thr Pro Ala Asp Leu Val Ala Ile Asp Phe Arg Thr Gly Gln Met
                820                 825                 830

Thr Val Gln Lys Asn Gln Ala Ile Asp Ala Asp Val Pro Pro Arg Phe
                835                 840                 845

Asn Leu Tyr Tyr Thr Val Thr Ala Ser Asp Lys Cys Ser Met Glu Asp
        850                 855                 860

Gln Ser Asn Cys Pro Asp Asp Lys Thr Tyr Trp Asn Thr Thr Ala Lys
865                 870                 875                 880

Ile Ala Ile Gln Val Ile Asp Thr Asn Asn Lys Val Pro Phe Val Glu
                885                 890                 895

Pro Glu Lys Phe Lys Asn Glu Val Thr Ile Val Glu Asp Pro Val Thr
                900                 905                 910

Gly Asp Val Thr Phe Leu Thr Ser Glu Ser Ile Tyr Glu Asp Ala Val
                915                 920                 925

Ser Gly Asp His Val Phe Gln Leu Phe Val Gly Asp Leu Asp Arg Asp
        930                 935                 940

Leu Pro Asn Asn Asn Val Ser Tyr Thr Ile Asn Phe Gly Val Asn Pro
945                 950                 955                 960

Arg Ile Arg Asp Phe Phe Glu Val Asp Leu Val Thr Gly Trp Val Arg
                965                 970                 975

Val His Tyr Pro Gly Pro Asp Lys Leu Asp Arg Asp Gly Asp Glu Pro
                980                 985                 990

Thr His Arg Ile His Phe Ser Ile Phe Asp Asn Phe Met Ser Glu Gly
        995                 1000                1005

Glu Pro Asn Arg Asn Gln Ile Ser Gly Glu Ala Leu Ile Ile Leu Leu
        1010                1015                1020

Asp Val Asn Asp Asn Lys Pro Glu Leu Pro Ser Pro Asp Ser Phe Pro
1025                1030                1035                1040

Pro Trp Thr Val Ser Glu Ser Val Glu Gly Val Arg Ile Pro Pro
                1045                1050                1055

Glu Ile Leu Ala Pro Asp Arg Asp Glu Pro Gly Thr Asp Asn Ser Arg
        1060                1065                1070

Val Ala Tyr Asp Leu Leu Gly Val Thr Pro Glu Arg Asp Ile Glu Val
        1075                1080                1085

Pro Gln Leu Phe Lys Ile Glu Thr Ile Glu Lys Asp Leu Gly Ile Asn
        1090                1095                1100

Gln Thr Gly Ile Leu Glu Thr Val Thr Pro Leu Gln Gly Tyr Trp Gly
1105                1110                1115                1120

Thr Tyr Glu Ile His Ile Lys Ala Phe Asp His Gly Asp Pro Arg Gln
                1125                1130                1135

Glu Ser Asp Glu Lys Tyr Gln Leu Val Val Arg Pro Tyr Asn Phe His

-continued

|   | 1140 |   |   |   | 1145 |   |   |   | 1150 |   |   |
|---|---|---|---|---|---|---|---|---|---|---|---|

Glu Pro Thr Phe Val Phe Pro Leu Asp Gly Ser Ala Ile Arg Leu Ser
       1155             1160             1165

Arg Asp Arg Ala Ile Val Ser Gly Glu Leu Thr Val Gly Ala Ala
1170             1175             1180

Gln Ala Pro Leu Gln Arg Ile Ser Ala Thr Asp Glu Asp Gly Leu His
1185             1190             1195             1200

Ala Gly Thr Val Ser Phe Ser Val Val Gly Asp Glu Ala Met Asn
             1205             1210             1215

Tyr Phe Asp Val Trp Asn Asp Gly Glu Asn Ser Gly Met Leu Ala Leu
       1220             1225             1230

Lys Gln Ala Leu Pro Asp Gly Phe Gln Glu Phe Lys Leu Thr Ile Arg
       1235             1240             1245

Ala Thr Asp Ala Gly Asp Glu Pro Gly Pro Lys Ser Thr Asp Ser Thr
       1250             1255             1260

Val Thr Val Val Phe Ile Pro Gln Val Glu Pro Gln Phe Pro Thr Asn
1265             1270             1275             1280

Thr Gln Glu Val Ala Phe Ile Glu Phe Glu Ala Gly Arg Ser Glu Arg
             1285             1290             1295

His Glu Leu Thr Ala Ala Val Asp Gln Lys Asn Ile Leu Cys Asp Ile
             1300             1305             1310

Asp Cys Tyr Thr Val Tyr Tyr Thr Ile Ile Gly Gly Asn Ala Ala Gly
             1315             1320             1325

His Phe Ala Leu Asp Gly Asn Val Leu Tyr Leu Val Ser Glu Leu Asp
       1330             1335             1340

Arg Ala Gln Ala Glu Arg His Thr Leu Gln Val Ala Ala Ser Asn Val
1345             1350             1355             1360

Pro Gly Val Thr Thr Ala Ala Pro Ala Ser Thr Leu Thr Val Ile Val
             1365             1370             1375

Thr Val Arg Glu Ala Asn Pro Arg Pro His Phe Glu Arg Asn Leu Tyr
             1380             1385             1390

Thr Thr Gly Met Ser Ala Thr Asp Thr Asp Ser Glu Arg Pro Leu Leu
       1395             1400             1405

Thr Val Ser Ala Thr His Ser Glu Gly Leu Pro Ile Thr Tyr Ala Ile
1410             1415             1420

Asp Gln Asp Ser Met Val Leu Asp Pro Thr Leu Glu Gln Val Arg Glu
1425             1430             1435             1440

Ser Ala Phe Ser Met Asn Pro Asp Thr Gly Glu Leu Met Arg Met Ile
             1445             1450             1455

Gln Pro Asn Ala Asn Met His Gly Met Phe Glu Phe Asp Ile Leu Ala
             1460             1465             1470

Thr Asp Thr Ala Gly Ala Thr Gly Gln Ser His Val Lys Val Tyr Leu
       1475             1480             1485

Ile Ser Ser Arg Asn Arg Val Tyr Phe Thr Phe Tyr Asn Ser Gln Glu
       1490             1495             1500

Ser Val Gln Glu His Arg Thr Phe Ile Ala Gln Thr Phe Thr Arg Val
1505             1510             1515             1520

Tyr Ser Met Thr Cys Asn Ile Glu Asp Ile Val Pro Ala Thr Asp Ser
             1525             1530             1535

Asn Gly Gln Tyr Leu Thr Thr Glu Thr His Val Thr Ala His Phe Ile
       1540             1545             1550

Arg Asp Asp Leu Pro Val Asp Ala Asp Val Gln Glu Leu Ile Glu
1555             1560             1565

-continued

```
Asp Thr Glu Leu Phe Arg Glu Leu Arg Thr Thr Met Leu Gly Leu Gly
    1570                1575                1580

Leu Gln Leu Thr Asn Val Gln Ser Gly Leu Pro Pro Ser Val Ala Gly
1585                1590                1595                1600

Glu Asp Gln Met Leu Ala Val Tyr Ile Leu Ala Gly Leu Ala Gly Val
                1605                1610                1615

Leu Ala Leu Leu Cys Ile Val Leu Leu Ile Thr Phe Ile Ile Arg Asn
            1620                1625                1630

Arg Ser Leu Asn Arg Arg Ile Ala Ala Leu Ser Ala Thr Lys Tyr Asn
        1635                1640                1645

Ser Val Asp Ser Asn Leu Asn Arg Ile Gly Leu Ala Ala Pro Gly Thr
    1650                1655                1660

Asn Lys His Ala Phe Glu Pro Asn Pro Ile Trp Asn Glu Thr Ile Lys
1665                1670                1675                1680

Ala Pro Asp Phe Asp Ala Ile Ser Glu Gln Ser Asn Asp Ser Asp Leu
                1685                1690                1695

Ile Gly Ile Glu Asp Leu Pro Gln Phe Arg Asn Asp Tyr Phe Pro Pro
            1700                1705                1710

Glu Gln Glu Ile Asp Met Asn Ser Asn Asp Ile Gly Tyr Pro Glu Met
        1715                1720                1725

Asp Ala Arg Asn Pro Leu Pro Asn His Glu Asn Asn Phe Gly Tyr Ser
    1730                1735                1740

Asn Ala Pro Phe Asn Pro Asp Phe Thr Asn Ser Gln Ser Arg Arg
1745                1750                1755

<210> SEQ ID NO 3
<211> LENGTH: 24
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 3, 12
<223> OTHER INFORMATION: n = A,T,C or G
<220> FEATURE:
<221> NAME/KEY: misc_feature
<222> LOCATION: 6
<223> OTHER INFORMATION: h = A, C, or T
<220> FEATURE:
<221> NAME/KEY: misc_feature
<222> LOCATION: 9, 15
<223> OTHER INFORMATION: y = T or C

<400> SEQUENCE: 3
gcnathgayg gngayacggg aatc                                          24

<210> SEQ ID NO 4
<211> LENGTH: 21
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 3
<223> OTHER INFORMATION: n = A,T,C or G
<220> FEATURE:
<221> NAME/KEY: misc_feature
<222> LOCATION: 6
<223> OTHER INFORMATION: y = T or C
<220> FEATURE:
<221> NAME/KEY: misc_feature
<222> LOCATION: 9, 12, 18
```

-continued

<223> OTHER INFORMATION: r = G or A

<400> SEQUENCE: 4
ggnagytcrt crttccartt g                         21

<210> SEQ ID NO 5
<211> LENGTH: 21
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 10, 16
<223> OTHER INFORMATION: n = A,T,C or G
<220> FEATURE:
<221> NAME/KEY: misc_feature
<222> LOCATION: 7
<223> OTHER INFORMATION: r = G or A
<220> FEATURE:
<221> NAME/KEY: misc_feature
<222> LOCATION: 8
<223> OTHER INFORMATION: k = G or T
<220> FEATURE:
<221> NAME/KEY: misc_feature
<222> LOCATION: 13
<223> OTHER INFORMATION: s = G or C
<220> FEATURE:
<221> NAME/KEY: misc_feature
<222> LOCATION: 14
<223> OTHER INFORMATION: w = A or T

<400> SEQUENCE: 5
gaagccrkcn ccswcngtct c                         21

<210> SEQ ID NO 6
<211> LENGTH: 1734
<212> TYPE: PRT
<213> ORGANISM: Spodoptera frugiperda

<400> SEQUENCE: 6

Met Ala Val Asp Val Arg Ile Leu Thr Ala Thr Leu Leu Val Leu Thr
 1               5                  10                  15

Thr Ala Thr Ala Gln Arg Asp Arg Cys Gly Tyr Met Val Glu Ile Pro
            20                  25                  30

Arg Pro Asp Arg Pro Asp Phe Pro Pro Gln Asn Phe Asp Gly Leu Thr
        35                  40                  45

Trp Ala Gln Gln Pro Leu Leu Pro Ala Glu Asp Arg Glu Glu Val Cys
    50                  55                  60

Leu Asn Asp Tyr Glu Pro Asp Pro Trp Ser Asn His Gly Asp Gln
65                  70                  75                  80

Arg Ile Tyr Met Glu Glu Ile Glu Gly Pro Val Val Ile Ala Lys
                85                  90                  95

Ile Asn Tyr Gln Gly Asn Thr Pro Pro Gln Ile Arg Leu Pro Phe Arg
            100                 105                 110

Val Gly Ala Ala His Met Leu Gly Ala Glu Ile Arg Glu Tyr Pro Asp
        115                 120                 125

Ala Thr Gly Asp Trp Tyr Leu Val Ile Thr Gln Arg Gln Asp Tyr Glu
    130                 135                 140

Thr Pro Asp Met Gln Arg Tyr Thr Phe Asp Val Ser Val Glu Gly Gln
145                 150                 155                 160

Ser Leu Val Val Thr Val Arg Leu Asp Ile Val Asn Ile Asp Asp Asn
                165                 170                 175

-continued

```
Ala Pro Ile Ile Glu Met Leu Glu Pro Cys Asn Leu Pro Glu Leu Val
            180                 185                 190

Glu Pro His Val Thr Glu Cys Lys Tyr Ile Val Ser Asp Ala Asp Gly
        195                 200                 205

Leu Ile Ser Thr Ser Val Met Ser Tyr His Ile Asp Ser Glu Arg Gly
        210                 215                 220

Asp Glu Lys Val Phe Glu Leu Ile Arg Lys Asp Tyr Pro Gly Asp Trp
225                 230                 235                 240

Thr Lys Val Tyr Met Val Leu Glu Leu Lys Lys Ser Leu Asp Tyr Glu
                245                 250                 255

Glu Asn Pro Leu His Ile Phe Arg Val Thr Ala Ser Asp Ser Leu Pro
            260                 265                 270

Asn Asn Arg Thr Val Val Met Met Val Glu Val Glu Asn Val Glu His
        275                 280                 285

Arg Asn Pro Arg Trp Met Glu Ile Phe Ala Val Gln Gln Phe Asp Glu
        290                 295                 300

Lys Gln Ala Lys Ser Phe Thr Val Arg Ala Ile Asp Gly Asp Thr Gly
305                 310                 315                 320

Ile Asn Lys Pro Ile Phe Tyr Arg Ile Glu Thr Glu Asp Glu Asp Lys
                325                 330                 335

Glu Phe Phe Ser Ile Glu Asn Ile Gly Glu Gly Arg Asp Gly Ala Arg
            340                 345                 350

Phe His Val Ala Pro Ile Asp Arg Asp Tyr Leu Lys Arg Asp Met Phe
        355                 360                 365

His Ile Arg Ile Ile Ala Tyr Lys Gln Gly Asp Asn Asp Lys Glu Gly
        370                 375                 380

Glu Ser Ser Phe Glu Thr Ser Ala Asn Val Thr Ile Ile Ile Asn Asp
385                 390                 395                 400

Ile Asn Asp Gln Arg Pro Glu Pro Phe His Lys Glu Tyr Thr Ile Ser
                405                 410                 415

Ile Met Glu Glu Thr Ala Met Thr Leu Asp Leu Gln Glu Phe Gly Phe
            420                 425                 430

His Asp Arg Asp Ile Gly Pro His Ala Gln Tyr Asp Val His Leu Glu
        435                 440                 445

Ser Ile Gln Pro Glu Gly Ala His Thr Ala Phe Tyr Ile Ala Pro Glu
        450                 455                 460

Glu Gly Tyr Gln Ala Gln Ser Phe Thr Ile Gly Thr Arg Ile His Asn
465                 470                 475                 480

Met Leu Asp Tyr Glu Asp Asp Tyr Arg Pro Gly Ile Lys Leu Lys
                485                 490                 495

Ala Val Ala Ile Asp Arg His Asp Asn Asn His Ile Gly Glu Ala Ile
            500                 505                 510

Ile Asn Ile Asn Leu Ile Asn Trp Asn Asp Glu Leu Pro Ile Phe Asp
            515                 520                 525

Glu Asp Ala Tyr Asn Val Thr Phe Glu Glu Thr Val Gly Asp Gly Phe
        530                 535                 540

His Ile Gly Lys Tyr Arg Ala Lys Asp Arg Asp Ile Gly Asp Ile Val
545                 550                 555                 560

Glu His Ser Ile Leu Gly Asn Ala Ala Asn Phe Leu Arg Ile Asp Ile
                565                 570                 575

Asp Thr Gly Asp Val Tyr Val Ser Arg Asp Asp Tyr Phe Asp Tyr Gln
            580                 585                 590

Arg Gln Asn Glu Ile Ile Val Gln Ile Leu Ala Val Asp Thr Leu Gly
```

```
                    595                 600                 605
Leu Pro Gln Asn Arg Ala Thr Thr Gln Leu Thr Ile Phe Leu Glu Asp
    610                 615                 620
Ile Asn Thr Pro Pro Ile Leu Arg Leu Pro Arg Ser Ser Pro Ser
625                 630                 635                 640
Val Glu Glu Asn Val Glu Val Gly His Pro Ile Thr Glu Gly Leu Thr
                645                 650                 655
Ala Thr Asp Pro Asp Thr Thr Ala Asp Leu His Phe Glu Ile Asp Trp
                660                 665                 670
Asp Asn Ser Tyr Ala Thr Lys Gln Gly Thr Asn Gly Pro Asn Thr Ala
                675                 680                 685
Asp Tyr His Gly Cys Val Glu Ile Leu Thr Val Tyr Pro Asp Pro Asp
            690                 695                 700
Asn His Gly Arg Ala Glu Gly His Leu Val Ala Arg Glu Val Ser Asp
705                 710                 715                 720
Gly Val Thr Ile Asp Tyr Glu Lys Phe Glu Val Leu Tyr Leu Val Val
                    725                 730                 735
Arg Val Ile Asp Arg Asn Thr Val Ile Gly Pro Asp Tyr Asp Glu Ala
                740                 745                 750
Met Leu Thr Val Thr Ile Ile Asp Met Asn Asp Asn Trp Pro Ile Trp
                755                 760                 765
Ala Asp Asn Thr Leu Gln Gln Thr Leu Arg Val Arg Glu Met Ala Asp
770                 775                 780
Glu Gly Val Ile Val Gly Thr Leu Leu Ala Thr Asp Leu Asp Gly Pro
785                 790                 795                 800
Leu Tyr Asn Arg Val Arg Tyr Thr Met Val Pro Ile Lys Asp Thr Pro
                805                 810                 815
Asp Asp Leu Ile Ala Ile Asn Tyr Val Thr Gly Gln Leu Thr Val Asn
                820                 825                 830
Lys Gly Gln Ala Ile Asp Ala Asp Pro Pro Arg Phe Tyr Leu Tyr
            835                 840                 845
Tyr Lys Val Thr Ala Ser Asp Lys Cys Ser Leu Asp Glu Phe Phe Pro
850                 855                 860
Val Cys Pro Pro Asp Pro Thr Tyr Trp Asn Thr Glu Gly Glu Ile Ala
865                 870                 875                 880
Ile Ala Ile Thr Asp Thr Asn Asn Lys Ile Pro Arg Ala Glu Thr Asp
                885                 890                 895
Met Phe Pro Ser Glu Lys Arg Ile Tyr Glu Asn Thr Pro Asn Gly Thr
                900                 905                 910
Lys Ile Thr Thr Ile Ile Ala Ser Asp Gln Asp Arg Asp Arg Pro Asn
            915                 920                 925
Asn Ala Leu Thr Tyr Arg Ile Asn Tyr Ala Phe Asn His Arg Leu Glu
            930                 935                 940
Asn Phe Phe Ala Val Asp Pro Asp Thr Gly Glu Leu Phe Val His Phe
945                 950                 955                 960
Thr Thr Ser Glu Val Leu Asp Arg Asp Gly Glu Pro Glu His Arg
                965                 970                 975
Ile Ile Phe Thr Ile Val Asp Asn Leu Glu Gly Ala Gly Asp Gly Asn
                980                 985                 990
Gln Asn Thr Ile Ser Thr Glu Val Arg Val Ile Leu Leu Asp Ile Asn
            995                 1000                1005
Asp Asn Lys Pro Glu Leu Pro Ile Pro Asp Gly Glu Phe Trp Thr Val
            1010                1015                1020
```

```
Ser Glu Gly Glu Val Glu Gly Lys Arg Ile Pro Pro Glu Ile His Ala
1025                1030                1035                1040

His Asp Arg Asp Glu Pro Phe Asn Asp Asn Ser Arg Val Gly Tyr Glu
                1045                1050                1055

Ile Arg Ser Ile Lys Leu Ile Asn Arg Asp Ile Glu Leu Pro Gln Asp
                1060                1065                1070

Pro Phe Lys Ile Ile Thr Ile Asp Asp Leu Asp Thr Trp Lys Phe Val
                1075                1080                1085

Gly Glu Leu Glu Thr Thr Met Asp Leu Arg Gly Tyr Trp Gly Thr Tyr
                1090                1095                1100

Asp Val Glu Ile Arg Ala Phe Asp His Gly Phe Pro Met Leu Asp Ser
1105                1110                1115                1120

Phe Glu Thr Tyr Gln Leu Thr Val Arg Pro Tyr Asn Phe His Ser Pro
                1125                1130                1135

Val Phe Val Phe Pro Thr Pro Gly Ser Thr Ile Arg Leu Ser Arg Glu
                1140                1145                1150

Arg Ala Ile Val Asn Gly Met Leu Ala Leu Ala Asn Ile Ala Ser Gly
                1155                1160                1165

Glu Phe Leu Asp Arg Leu Ser Ala Thr Asp Glu Asp Gly Leu His Ala
    1170                1175                1180

Gly Arg Val Thr Phe Ser Ile Ala Gly Asn Asp Glu Ala Ala Glu Tyr
1185                1190                1195                1200

Phe Asn Val Leu Asn Asp Gly Asp Asn Ser Ala Met Leu Thr Leu Lys
                1205                1210                1215

Gln Ala Leu Pro Ala Gly Val Gln Gln Phe Glu Leu Val Ile Arg Ala
                1220                1225                1230

Thr Asp Gly Gly Thr Glu Pro Gly Pro Arg Ser Thr Asp Cys Ser Val
                1235                1240                1245

Thr Val Val Phe Val Met Thr Gln Gly Asp Pro Val Phe Asp Asp Asn
1250                1255                1260

Ala Ala Ser Val Arg Phe Val Glu Lys Glu Ala Gly Met Ser Glu Lys
1265                1270                1275                1280

Phe Gln Leu Pro Gln Ala Asp Asp Pro Lys Asn Tyr Arg Cys Met Asp
                1285                1290                1295

Asp Cys His Thr Ile Tyr Tyr Ser Ile Val Asp Gly Asn Asp Gly Asp
                1300                1305                1310

His Phe Ala Val Glu Pro Glu Thr Asn Val Ile Tyr Leu Leu Lys Pro
                1315                1320                1325

Leu Asp Arg Ser Gln Gln Glu Gln Tyr Arg Val Val Ala Ala Ser
    1330                1335                1340

Asn Thr Pro Gly Gly Thr Ser Thr Leu Ser Ser Ser Leu Leu Thr Val
1345                1350                1355                1360

Thr Ile Gly Val Arg Glu Ala Asn Pro Arg Pro Ile Phe Glu Ser Glu
                1365                1370                1375

Phe Tyr Thr Ala Gly Val Leu His Thr Asp Ser Ile His Lys Glu Leu
                1380                1385                1390

Val Tyr Leu Ala Ala Lys His Ser Glu Gly Leu Pro Ile Val Tyr Ser
    1395                1400                1405

Ile Asp Gln Glu Thr Met Lys Ile Asp Glu Ser Leu Gln Thr Val Val
    1410                1415                1420

Glu Asp Ala Phe Asp Ile Asn Ser Ala Thr Gly Val Ile Ser Leu Asn
1425                1430                1435                1440
```

Phe Gln Pro Thr Ser Val Met His Gly Ser Phe Asp Phe Glu Val Val
                1445                1450                1455

Ala Ser Asp Thr Arg Gly Ala Ser Asp Arg Ala Lys Val Ser Ile Tyr
            1460                1465                1470

Met Ile Ser Thr Arg Val Arg Val Ala Phe Leu Phe Tyr Asn Thr Glu
        1475                1480                1485

Ala Glu Val Asn Glu Arg Arg Asn Phe Ile Ala Gln Thr Phe Ala Asn
    1490                1495                1500

Ala Phe Gly Met Thr Cys Asn Ile Asp Ser Val Leu Pro Ala Thr Asp
1505                1510                1515                1520

Ala Asn Gly Val Ile Arg Glu Gly Tyr Thr Glu Leu Gln Ala His Phe
                1525                1530                1535

Ile Arg Asp Asp Gln Pro Val Pro Ala Asp Tyr Ile Glu Gly Leu Phe
            1540                1545                1550

Thr Glu Leu Asn Thr Leu Arg Asp Ile Arg Glu Val Leu Ser Thr Gln
        1555                1560                1565

Gln Leu Thr Leu Leu Asp Phe Ala Ala Gly Gly Ser Ala Val Leu Pro
    1570                1575                1580

Gly Gly Glu Tyr Ala Leu Ala Val Tyr Ile Leu Ala Gly Ile Ala Ala
1585                1590                1595                1600

Leu Leu Ala Val Ile Cys Leu Ala Leu Leu Ile Ala Phe Phe Ile Arg
                1605                1610                1615

Asn Arg Thr Leu Asn Arg Arg Ile Glu Ala Leu Thr Ile Lys Asp Val
            1620                1625                1630

Pro Thr Asp Ile Glu Pro Asn His Ala Ser Val Ala Val Leu Asn Ile
        1635                1640                1645

Asn Lys His Thr Glu Pro Gly Ser Asn Pro Phe Tyr Asn Pro Asp Val
    1650                1655                1660

Lys Thr Pro Asn Phe Asp Thr Ile Ser Glu Val Ser Asp Asp Leu Leu
1665                1670                1675                1680

Asp Val Glu Asp Leu Glu Gln Phe Gly Lys Asp Tyr Phe Pro Pro Glu
                1685                1690                1695

Asn Glu Ile Glu Ser Leu Asn Phe Ala Arg Asn Pro Ile Ala Thr His
            1700                1705                1710

Gly Asn Asn Phe Gly Val Asn Ser Ser Pro Ser Asn Pro Glu Phe Ser
        1715                1720                1725

Asn Ser Gln Phe Arg Ser
    1730

<210> SEQ ID NO 7
<211> LENGTH: 1730
<212> TYPE: PRT
<213> ORGANISM: Helicoverpa zea

<400> SEQUENCE: 7

Met Ala Val Asp Val Arg Ile Leu Thr Ala Ala Val Phe Ile Ile Ala
1               5                   10                  15

Ala His Leu Thr Phe Ala Gln Asp Cys Ser Tyr Met Val Ala Ile Pro
            20                  25                  30

Arg Pro Glu Arg Pro Asp Phe Pro Ser Leu Asn Phe Asp Gly Ile Pro
        35                  40                  45

Trp Ser Arg Tyr Pro Leu Ile Pro Val Glu Gly Arg Glu Asp Val Cys
    50                  55                  60

Met Asn Glu Phe Gln Pro Asp Ala Leu Asn Pro Val Thr Val Ile Phe
65                  70                  75                  80

-continued

```
Met Glu Glu Ile Glu Gly Asp Val Ala Ile Ala Arg Leu Asn Tyr
                85                  90                  95

Arg Gly Thr Asn Thr Pro Thr Ile Val Ser Pro Phe Ser Phe Gly Thr
            100                 105                 110

Phe Asn Met Leu Gly Pro Val Ile Arg Arg Ile Pro Glu Asn Gly Gly
        115                 120                 125

Asp Trp His Leu Val Ile Thr Gln Arg Gln Asp Tyr Glu Thr Pro Gly
    130                 135                 140

Met Gln Gln Tyr Ile Phe Asp Val Arg Val Asp Asp Glu Pro Leu Val
145                 150                 155                 160

Ala Thr Val Met Leu Leu Ile Val Asn Ile Asp Asp Asn Asp Pro Ile
                165                 170                 175

Ile Gln Met Phe Glu Pro Cys Asp Ile Pro Glu Arg Gly Glu Thr Gly
                180                 185                 190

Ile Thr Ser Cys Lys Tyr Thr Val Ser Asp Ala Asp Gly Glu Ile Ser
            195                 200                 205

Thr Arg Phe Met Arg Phe Glu Ile Ser Ser Asp Arg Asp Asp Asp Glu
    210                 215                 220

Tyr Phe Glu Leu Val Arg Glu Asn Ile Gln Gly Gln Trp Met Tyr Val
225                 230                 235                 240

His Met Arg Val His Val Lys Lys Pro Leu Asp Tyr Glu Glu Asn Pro
                245                 250                 255

Leu His Leu Phe Arg Val Thr Ala Tyr Asp Ser Leu Pro Asn Thr His
                260                 265                 270

Thr Val Thr Met Met Val Gln Val Glu Asn Val Glu Asn Arg Pro Pro
            275                 280                 285

Arg Trp Met Glu Ile Phe Ala Val Gln Gln Phe Asp Glu Lys Thr Glu
    290                 295                 300

Gln Ser Phe Arg Val Arg Ala Ile Asp Gly Asp Thr Gly Ile Asp Lys
305                 310                 315                 320

Pro Ile Phe Tyr Arg Ile Glu Thr Glu Lys Gly Glu Glu Asp Leu Phe
                325                 330                 335

Ser Ile Gln Thr Ile Glu Gly Gly Arg Glu Gly Ala Trp Phe Asn Val
            340                 345                 350

Ala Pro Ile Asp Arg Asp Thr Leu Glu Lys Glu Val Phe His Val Ser
        355                 360                 365

Ile Ile Ala Tyr Lys Tyr Gly Asp Asn Asp Val Glu Gly Ser Ser Ser
    370                 375                 380

Phe Gln Ser Lys Thr Asp Val Val Ile Ile Val Asn Asp Val Asn Asp
385                 390                 395                 400

Gln Ala Pro Leu Pro Phe Arg Glu Glu Tyr Ser Ile Glu Ile Met Glu
                405                 410                 415

Glu Thr Ala Met Thr Leu Asn Leu Glu Asp Phe Gly Phe His Asp Arg
            420                 425                 430

Asp Leu Gly Pro His Ala Gln Tyr Thr Val His Leu Glu Ser Ile His
        435                 440                 445

Pro Pro Arg Ala His Glu Ala Phe Tyr Ile Ala Pro Glu Val Gly Tyr
    450                 455                 460

Gln Arg Gln Ser Phe Ile Met Gly Thr Gln Asn His His Met Leu Asp
465                 470                 475                 480

Phe Glu Val Pro Glu Phe Gln Asn Ile Gln Leu Arg Ala Val Ala Ile
                485                 490                 495
```

-continued

```
Asp Met Asp Asp Pro Lys Trp Val Gly Ile Ala Ile Ile Asn Ile Lys
            500                 505                 510
Leu Ile Asn Trp Asn Asp Glu Leu Pro Met Phe Glu Ser Asp Val Gln
        515                 520                 525
Thr Val Ser Phe Asp Glu Thr Glu Gly Ala Gly Phe Tyr Val Ala Thr
    530                 535                 540
Val Val Ala Lys Asp Arg Asp Val Gly Asp Lys Val Glu His Ser Leu
545                 550                 555                 560
Met Gly Asn Ala Val Ser Tyr Leu Arg Ile Asp Lys Glu Thr Gly Glu
            565                 570                 575
Ile Phe Val Thr Glu Asn Glu Ala Phe Asn Tyr His Arg Gln Asn Glu
        580                 585                 590
Leu Phe Val Gln Ile Pro Ala Asp Asp Thr Leu Gly Glu Pro Tyr Asn
    595                 600                 605
Thr Asn Thr Thr Gln Leu Val Ile Lys Leu Arg Asp Ile Asn Asn Thr
610                 615                 620
Pro Pro Thr Leu Arg Leu Pro Arg Ala Thr Pro Ser Val Glu Glu Asn
625                 630                 635                 640
Val Pro Asp Gly Phe Val Ile Pro Thr Gln Leu His Ala Thr Asp Pro
            645                 650                 655
Asp Thr Thr Ala Glu Leu Arg Phe Glu Ile Asp Trp Gln Asn Ser Tyr
        660                 665                 670
Ala Thr Lys Gln Gly Arg Asn Thr Asp Ser Lys Glu Tyr Ile Gly Cys
    675                 680                 685
Ile Glu Ile Glu Thr Ile Tyr Pro Asn Ile Asn Gln Arg Gly Asn Ala
690                 695                 700
Ile Gly Arg Val Val Arg Glu Ile Arg Asp Gly Val Thr Ile Asp
705                 710                 715                 720
Tyr Glu Met Phe Glu Val Leu Tyr Leu Thr Val Ile Val Arg Asp Leu
            725                 730                 735
Asn Thr Val Ile Gly Glu Asp His Asp Ile Ser Thr Phe Thr Ile Thr
        740                 745                 750
Ile Ile Asp Met Asn Asp Asn Pro Pro Leu Trp Val Glu Gly Thr Leu
    755                 760                 765
Thr Gln Glu Phe Arg Val Arg Glu Val Ala Ala Ser Gly Val Val Ile
770                 775                 780
Gly Ser Val Leu Ala Thr Asp Ile Asp Gly Pro Leu Tyr Asn Gln Val
785                 790                 795                 800
Arg Tyr Thr Ile Thr Pro Arg Leu Asp Thr Pro Glu Asp Leu Val Asp
            805                 810                 815
Ile Asp Phe Asn Thr Gly Gln Ile Ser Val Lys Leu His Gln Ala Ile
        820                 825                 830
Asp Ala Asp Glu Pro Pro Arg Gln Asn Leu Tyr Tyr Thr Val Ile Ala
    835                 840                 845
Ser Asp Lys Cys Asp Leu Leu Thr Val Thr Glu Cys Pro Pro Asp Pro
850                 855                 860
Thr Tyr Phe Glu Thr Pro Gly Glu Ile Thr His Ile Thr Asp Thr
865                 870                 875                 880
Asn Asn Lys Val Pro Gln Val Glu Asp Lys Phe Glu Ala Thr Val
            885                 890                 895
Tyr Ile Tyr Glu Gly Ala Asp Asp Gly Gln His Val Gln Ile Tyr
        900                 905                 910
Ala Ser Asp Leu Asp Arg Asp Glu Ile Tyr His Lys Val Ser Tyr Gln
```

-continued

```
            915                 920                 925
Ile Asn Tyr Ala Ile Asn Ser Arg Leu Arg Asp Phe Phe Glu Met Asp
930                 935                 940

Leu Glu Ser Gly Leu Val Tyr Val Asn Asn Thr Ala Gly Leu Leu
945                 950                 955                 960

Asp Arg Asp Gly Asp Glu Pro Thr His Arg Ile Phe Phe Asn Val Ile
                965                 970                 975

Asp Asn Phe Tyr Gly Glu Gly Asp Gly Asn Arg Asn Gln Asn Glu Thr
                980                 985                 990

Gln Val Leu Val Val Leu Leu Asp Ile Asn Asp Asn Tyr Pro Glu Leu
                995                 1000                1005

Pro Glu Thr Ile Pro Trp Ala Ile Ser Glu Ser Leu Glu Leu Gly Glu
            1010                1015                1020

Arg Val Gln Pro Glu Ile Phe Ala Arg Asp Arg Asp Glu Pro Gly Thr
1025                1030                1035                1040

Asp Asn Ser Arg Val Ala Tyr Ala Ile Thr Gly Leu Ala Ser Thr Asp
                1045                1050                1055

Arg Asp Ile Gln Val Pro Asn Leu Phe Asn Met Ile Thr Ile Glu Arg
                1060                1065                1070

Asp Arg Gly Ile Asp Gln Thr Gly Ile Leu Glu Ala Ala Met Asp Leu
                1075                1080                1085

Arg Gly Tyr Trp Gly Thr Tyr Gln Ile Asp Ile Gln Ala Tyr Asp His
                1090                1095                1100

Gly Ile Pro Gln Arg Ile Ser Asn Gln Lys Tyr Pro Leu Val Ile Arg
1105                1110                1115                1120

Pro Tyr Asn Phe His Asp Pro Val Phe Val Phe Pro Gln Pro Gly Ser
                1125                1130                1135

Thr Ile Arg Leu Ala Lys Glu Arg Ala Val Val Asn Gly Ile Leu Ala
                1140                1145                1150

Thr Val Asp Gly Glu Phe Leu Asp Arg Ile Val Ala Thr Asp Glu Asp
                1155                1160                1165

Gly Leu Glu Ala Gly Leu Val Thr Phe Ser Ile Ala Gly Asp Asp Glu
        1170                1175                1180

Asp Ala Gln Phe Phe Asp Val Leu Asn Asp Gly Val Asn Ser Gly Ala
1185                1190                1195                1200

Leu Thr Leu Thr Arg Leu Phe Pro Glu Glu Phe Arg Glu Phe Gln Val
                1205                1210                1215

Thr Ile Arg Ala Thr Asp Gly Gly Thr Glu Pro Gly Pro Arg Ser Thr
                1220                1225                1230

Asp Cys Leu Val Thr Val Val Phe Val Pro Thr Gln Gly Glu Pro Val
                1235                1240                1245

Phe Glu Asp Arg Thr Tyr Thr Val Ala Phe Val Glu Lys Asp Glu Gly
                1250                1255                1260

Met Leu Glu Glu Ala Glu Leu Pro Arg Ala Ser Asp Pro Arg Asn Ile
1265                1270                1275                1280

Met Cys Glu Asp Asp Cys His Asp Thr Tyr Tyr Ser Ile Val Gly Gly
                1285                1290                1295

Asn Ser Gly Glu His Phe Thr Val Asp Pro Arg Thr Asn Val Leu Ser
                1300                1305                1310

Leu Val Lys Pro Leu Asp Arg Ser Glu Gln Glu Thr His Thr Leu Ile
            1315                1320                1325

Ile Gly Ala Ser Asp Thr Pro Asn Pro Ala Ala Val Leu Gln Ala Ser
        1330                1335                1340
```

```
Thr Leu Thr Val Thr Val Asn Val Arg Glu Ala Asn Pro Arg Pro Val
1345                1350                1355                1360

Phe Gln Arg Ala Leu Tyr Thr Ala Gly Ile Ser Ala Gly Asp Phe Ile
            1365                1370                1375

Glu Arg Asn Leu Leu Thr Leu Val Ala Thr His Ser Glu Asp Leu Pro
        1380                1385                1390

Ile Thr Tyr Thr Leu Ile Gln Glu Ser Met Glu Ala Asp Pro Thr Leu
            1395                1400                1405

Glu Ala Val Gln Glu Ser Ala Phe Ile Leu Asn Pro Glu Thr Gly Val
        1410                1415                1420

Leu Ser Leu Asn Phe Gln Pro Thr Ala Ser Met His Gly Met Phe Glu
1425                1430                1435                1440

Phe Glu Val Lys Ala Thr Asp Ser Arg Thr Glu Thr Ala Arg Thr Glu
            1445                1450                1455

Val Lys Val Tyr Leu Ile Ser Asp Arg Asn Arg Val Phe Phe Thr Phe
            1460                1465                1470

Asn Asn Pro Leu Pro Glu Val Thr Pro Gln Glu Asp Phe Ile Ala Glu
        1475                1480                1485

Thr Phe Thr Ala Phe Phe Gly Met Thr Cys Asn Ile Asp Gln Ser Trp
    1490                1495                1500

Trp Ala Ser Asp Pro Val Thr Gly Ala Thr Lys Asp Gln Thr Glu
1505                1510                1515                1520

Val Arg Ala His Phe Ile Arg Asp Asp Leu Pro Val Pro Ala Glu Glu
            1525                1530                1535

Ile Glu Gln Leu Arg Gly Asn Pro Thr Leu Val Asn Ser Ile Gln Arg
        1540                1545                1550

Ala Leu Glu Glu Gln Asn Leu Gln Leu Ala Asp Leu Phe Thr Gly Glu
    1555                1560                1565

Thr Pro Ile Leu Gly Gly Asp Ala Gln Ala Arg Ala Leu Tyr Ala Leu
    1570                1575                1580

Ala Ala Val Ala Ala Ala Leu Ala Leu Ile Val Val Val Leu Leu Ile
1585                1590                1595                1600

Val Phe Phe Val Arg Thr Arg Thr Leu Asn Arg Arg Leu Gln Ala Leu
            1605                1610                1615

Ser Met Thr Lys Tyr Ser Ser Gln Asp Ser Gly Leu Asn Arg Val Gly
            1620                1625                1630

Leu Ala Ala Pro Gly Thr Asn Lys His Ala Val Glu Gly Ser Asn Pro
        1635                1640                1645

Ile Trp Asn Glu Thr Leu Lys Ala Pro Asp Phe Asp Ala Leu Ser Glu
    1650                1655                1660

Gln Ser Tyr Asp Ser Asp Leu Ile Gly Ile Glu Asp Leu Pro Gln Phe
1665                1670                1675                1680

Arg Asn Asp Tyr Phe Pro Pro Glu Glu Gly Ser Ser Met Arg Gly Val
            1685                1690                1695

Val Asn Glu His Val Pro Glu Ser Ile Ala Asn His Asn Asn Asn Phe
        1700                1705                1710

Gly Phe Asn Ser Thr Pro Phe Ser Pro Glu Phe Ala Asn Thr Gln Phe
    1715                1720                1725

Arg Arg
    1730

<210> SEQ ID NO 8
<211> LENGTH: 1717
```

<212> TYPE: PRT
<213> ORGANISM: Ostrinia nubilalis

<400> SEQUENCE: 8

```
Met Gly Val Glu Arg Phe Phe Pro Ala Val Leu Leu Val Ser Leu Ala
 1               5                  10                  15

Ser Ala Ala Leu Ala Asn Gln Arg Cys Ser Tyr Ile Ile Ala Ile Pro
            20                  25                  30

Arg Pro Glu Thr Pro Glu Leu Pro Pro Ile Asp Tyr Glu Gly Lys Ser
        35                  40                  45

Trp Ser Glu Gln Pro Leu Ile Pro Gly Pro Thr Arg Glu Glu Val Cys
    50                  55                  60

Met Glu Asn Phe Leu Pro Asp Gln Met Ile Gln Val Ile Tyr Met Glu
65                  70                  75                  80

Glu Glu Ile Glu Gly Asp Val Ile Ile Ala Lys Leu Asn Tyr Gln Gly
                85                  90                  95

Ser Asn Thr Pro Val Leu Ser Ile Met Ser Gly Gln Pro Arg Ala Gln
            100                 105                 110

Leu Gly Pro Glu Phe Arg Gln Asn Glu Ala Asp Gly Gln Trp Ser Leu
        115                 120                 125

Val Ile Thr Gln Arg Gln Asp Tyr Glu Thr Ala Thr Met Gln Ser Tyr
    130                 135                 140

Val Phe Ser Ile Gln Val Glu Gly Glu Ser Gln Ala Val Leu Val Ala
145                 150                 155                 160

Leu Glu Ile Val Asn Ile Asp Asp Asn Pro Pro Ile Leu Gln Val Val
                165                 170                 175

Ser Ala Cys Val Ile Pro Glu His Gly Glu Ala Arg Leu Thr Asp Cys
            180                 185                 190

Val Tyr Gln Val Ser Asp Arg Asp Gly Glu Ile Ser Thr Arg Phe Met
        195                 200                 205

Thr Phe Arg Val Asp Ser Ser Arg Ala Ala Asp Glu Ser Ile Phe Tyr
    210                 215                 220

Met Val Gly Glu Tyr Asp Pro Ser Asp Trp Phe Asn Met Lys Met Thr
225                 230                 235                 240

Val Gly Ile Asn Ser Pro Leu Asn Phe Glu Thr Thr Gln Leu His Ile
                245                 250                 255

Phe Ser Val Thr Ala Ser Asp Ser Leu Pro Asn Asn His Thr Val Thr
            260                 265                 270

Met Met Val Gln Val Glu Asn Val Glu Ser Arg Pro Pro Arg Trp Val
        275                 280                 285

Glu Ile Phe Ser Val Gln Gln Phe Asp Glu Lys Thr Asn Gln Ser Phe
    290                 295                 300

Ser Leu Arg Ala Ile Asp Gly Asp Thr Gly Ile Asn Arg Ala Ile Asn
305                 310                 315                 320

Tyr Thr Leu Ile Arg Asp Asp Ala Asp Asp Phe Phe Ser Leu Glu Val
                325                 330                 335

Ile Glu Asp Gly Ala Ile Leu His Val Thr Glu Ile Asp Arg Asp Lys
            340                 345                 350

Leu Glu Arg Glu Leu Phe Asn Leu Thr Ile Val Ala Tyr Lys Ser Thr
        355                 360                 365

Asp Ala Ser Phe Ala Thr Glu Ala His Ile Phe Ile Ile Val Asn Asp
    370                 375                 380

Val Asn Asp Gln Arg Pro Glu Pro Leu His Lys Glu Tyr Ser Ile Asp
385                 390                 395                 400
```

-continued

```
Ile Met Glu Glu Thr Pro Met Thr Leu Asn Phe Asn Glu Phe Gly
            405                 410                 415

Phe His Asp Arg Asp Leu Gly Glu Asn Ala Gln Tyr Thr Val Glu Leu
            420                 425                 430

Glu Asp Val Phe Pro Pro Gly Ala Ala Ser Ala Phe Tyr Ile Ala Pro
            435                 440                 445

Gly Ser Gly Tyr Gln Arg Gln Thr Phe Ile Met Gly Thr Ile Asn His
    450                 455                 460

Thr Met Leu Asp Tyr Glu Asp Val Ile Phe Gln Asn Ile Ile Lys
465                 470                 475                 480

Val Lys Ala Val Asp Met Asn Asn Ala Ser His Val Gly Glu Ala Leu
            485                 490                 495

Val Tyr Val Asn Leu Ile Asn Trp Asn Asp Leu Pro Ile Phe Glu
    500                 505                 510

Glu Ser Ser Tyr Ser Ala Ser Phe Lys Glu Thr Val Gly Ala Gly Phe
    515                 520                 525

Pro Val Ala Thr Val Leu Ala Leu Asp Arg Asp Ile Asp Asp Val Val
    530                 535                 540

Val His Ser Leu Met Gly Asn Ala Val Asp Tyr Leu Phe Ile Asp Glu
545                 550                 555                 560

Ser Thr Gly Glu Ile Phe Val Ser Met Asp Asp Ala Phe Asp Tyr His
                565                 570                 575

Arg Gln Asn Thr Leu Phe Val Gln Val Arg Ala Asp Asp Thr Leu Gly
            580                 585                 590

Asp Gly Pro His Asn Thr Val Thr Thr Gln Leu Val Ile Glu Leu Glu
            595                 600                 605

Asp Val Asn Asn Thr Pro Pro Thr Leu Arg Leu Pro Arg Ser Thr Pro
            610                 615                 620

Ser Val Glu Glu Asn Val Pro Glu Gly Tyr Glu Ile Ser Arg Glu Ile
625                 630                 635                 640

Thr Ala Thr Asp Pro Asp Thr Ser Ala Tyr Leu Trp Phe Glu Ile Asp
                645                 650                 655

Trp Asp Ser Thr Trp Ala Thr Lys Gln Gly Arg Glu Thr Asn Pro Thr
            660                 665                 670

Glu Tyr Val Gly Cys Ile Val Ile Glu Thr Ile Tyr Pro Thr Glu Gly
            675                 680                 685

Asn Arg Gly Ser Ala Ile Gly Arg Leu Val Val Gln Glu Ile Arg Asp
    690                 695                 700

Asn Val Thr Ile Asp Phe Glu Glu Phe Glu Met Leu Tyr Leu Thr Val
705                 710                 715                 720

Arg Val Arg Asp Leu Asn Thr Val Ile Gly Asp Tyr Asp Glu Ala
                725                 730                 735

Thr Phe Thr Ile Thr Ile Asp Met Asn Asp Asn Ala Pro Ile Phe
                740                 745                 750

Ala Asn Gly Thr Leu Thr Gln Thr Met Arg Val Arg Glu Leu Ala Ala
    755                 760                 765

Ser Gly Thr Leu Ile Gly Ser Val Leu Ala Thr Asp Ile Asp Gly Pro
    770                 775                 780

Leu Tyr Asn Gln Val Arg Tyr Thr Ile Gln Pro Arg Asn Asn Thr Pro
785                 790                 795                 800

Glu Gly Leu Val Lys Ile Asp Phe Thr Thr Gly Gln Ile Glu Val Asp
            805                 810                 815
```

-continued

Ala Asn Glu Ala Ile Asp Ala Asp Glu Pro Trp Arg Phe Tyr Leu Tyr
        820              825              830

Tyr Thr Val Ile Ala Ser Asp Glu Cys Ser Leu Glu Asn Arg Thr Glu
        835              840              845

Cys Pro Pro Asp Ser Asn Tyr Phe Glu Val Pro Gly Asp Ile Glu Ile
        850              855              860

Glu Ile Ile Asp Thr Asn Asn Lys Val Pro Glu Pro Leu Thr Glu Lys
865              870              875              880

Phe Asn Thr Thr Val Tyr Val Trp Glu Asn Ala Thr Ser Gly Asp Glu
            885              890              895

Val Val Gln Leu Tyr Ser His Asp Arg Asp Arg Asp Glu Leu Tyr His
        900              905              910

Thr Val Arg Tyr Thr Met Asn Phe Ala Val Asn Pro Arg Leu Arg Asp
        915              920              925

Phe Phe Glu Val Asp Leu Asp Thr Gly Arg Leu Glu Val His Tyr Pro
    930              935              940

Gly Asp Glu Lys Leu Asp Arg Asp Gly Asp Glu Pro Thr His Thr Ile
945              950              955              960

Phe Val Asn Phe Ile Asp Asn Phe Phe Ser Asp Gly Asp Gly Arg Arg
            965              970              975

Asn Gln Asp Glu Val Glu Ile Phe Val Val Leu Leu Asp Val Asn Asp
        980              985              990

Asn Ala Pro Glu Met Pro Leu Pro Asp Glu Leu Arg Phe Asp Val Ser
        995              1000             1005

Glu Gly Ala Val Ala Gly Val Arg Val Leu Pro Glu Ile Tyr Ala Pro
    1010             1015             1020

Asp Arg Asp Glu Pro Asp Thr Asp Asn Ser Arg Val Gly Tyr Gly Ile
1025             1030             1035             1040

Leu Asp Leu Thr Ile Thr Asp Arg Asp Ile Glu Val Pro Asp Leu Phe
            1045             1050             1055

Thr Met Ile Ser Ile Glu Asn Lys Thr Gly Glu Leu Glu Thr Ala Met
        1060             1065             1070

Asp Leu Arg Gly Tyr Trp Gly Thr Tyr Glu Ile Phe Ile Glu Ala Phe
        1075             1080             1085

Asp His Gly Tyr Pro Gln Gln Arg Ser Asn Glu Thr Tyr Thr Leu Val
        1090             1095             1100

Ile Arg Pro Tyr Asn Phe His His Pro Val Phe Val Phe Pro Gln Pro
1105             1110             1115             1120

Asp Ser Val Ile Arg Leu Ser Arg Glu Arg Ala Thr Glu Gly Gly Val
            1125             1130             1135

Leu Ala Thr Ala Ala Asn Glu Phe Leu Glu Pro Ile Tyr Ala Thr Asp
            1140             1145             1150

Glu Asp Gly Leu His Ala Gly Ser Val Thr Phe His Val Gln Gly Asn
        1155             1160             1165

Glu Glu Ala Val Gln Tyr Phe Asp Ile Thr Glu Val Gly Ala Gly Glu
        1170             1175             1180

Asn Ser Gly Gln Leu Ile Leu Arg Gln Leu Phe Pro Glu Gln Ile Arg
1185             1190             1195             1200

Gln Phe Arg Ile Thr Ile Arg Ala Thr Asp Gly Gly Thr Glu Pro Gly
            1205             1210             1215

Pro Leu Trp Thr Asp Val Thr Phe Ser Val Val Phe Val Pro Thr Gln
        1220             1225             1230

Gly Asp Pro Val Phe Ser Glu Asn Ala Ala Thr Val Ala Phe Phe Glu

-continued

```
            1235                1240                1245
Gly Glu Glu Gly Leu Arg Glu Ser Phe Glu Leu Pro Gln Ala Glu Asp
    1250                1255                1260
Leu Lys Asn His Leu Cys Glu Asp Cys Gln Asp Ile Tyr Tyr Arg
1265                1270                1275                1280
Phe Ile Asp Gly Asn Asn Glu Gly Leu Phe Val Leu Asp Gln Ser Ser
                1285                1290                1295
Asn Val Ile Ser Leu Ala Gln Glu Leu Asp Arg Glu Val Ala Thr Ser
            1300                1305                1310
Tyr Thr Leu His Ile Ala Ala Ser Asn Ser Pro Asp Ala Thr Gly Ile
        1315                1320                1325
Pro Leu Gln Thr Ser Ile Leu Val Val Thr Val Asn Val Arg Glu Ala
    1330                1335                1340
Asn Pro Arg Pro Ile Phe Glu Gln Asp Leu Tyr Thr Ala Gly Ile Ser
1345                1350                1355                1360
Thr Leu Asp Ser Ile Gly Arg Glu Leu Leu Thr Val Arg Ala Ser His
                1365                1370                1375
Thr Glu Asp Asp Thr Ile Thr Tyr Thr Ile Asp Arg Ala Ser Met Gln
            1380                1385                1390
Leu Asp Ser Ser Leu Glu Ala Val Arg Asp Ser Ala Phe Ala Leu His
        1395                1400                1405
Ala Thr Thr Gly Val Leu Ser Leu Asn Met Gln Pro Thr Ala Ser Met
    1410                1415                1420
His Gly Met Phe Glu Phe Asp Val Ile Ala Thr Asp Thr Ala Ser Ala
1425                1430                1435                1440
Ile Asp Thr Ala Arg Val Lys Val Tyr Leu Ile Ser Ser Gln Asn Arg
                1445                1450                1455
Val Thr Phe Ile Phe Asp Asn Gln Leu Glu Thr Val Glu Gln Asn Arg
            1460                1465                1470
Asn Phe Ile Ala Ala Thr Phe Ser Thr Gly Phe Asn Met Thr Cys Asn
        1475                1480                1485
Ile Asp Gln Val Val Pro Phe Ser Asp Ser Ser Gly Val Ala Gln Asp
    1490                1495                1500
Asp Thr Thr Glu Val Arg Ala His Phe Ile Arg Asp Asn Val Pro Val
1505                1510                1515                1520
Gln Ala Gln Glu Val Glu Ala Val Arg Ser Asp Thr Val Leu Leu Arg
                1525                1530                1535
Thr Ile Gln Leu Met Leu Ser Thr Asn Ser Leu Val Leu Gln Asp Leu
            1540                1545                1550
Val Thr Gly Asp Thr Pro Thr Leu Gly Glu Glu Ser Met Gln Ile Ala
        1555                1560                1565
Val Tyr Ala Leu Ala Ala Leu Ser Ala Val Leu Gly Phe Leu Cys Leu
    1570                1575                1580
Val Leu Leu Leu Ala Leu Phe Cys Arg Thr Arg Ala Leu Asn Arg Gln
1585                1590                1595                1600
Leu Gln Ala Leu Ser Met Thr Lys Tyr Gly Ser Val Asp Ser Gly Leu
                1605                1610                1615
Asn Arg Ala Gly Leu Ala Pro Gly Thr Asn Lys His Ala Val Glu Gly
            1620                1625                1630
Ser Asn Pro Met Trp Asn Glu Ala Ile Arg Ala Pro Asp Phe Asp Ala
        1635                1640                1645
Ile Ser Asp Ala Ser Gly Asp Ser Asp Leu Ile Gly Ile Glu Asp Met
    1650                1655                1660
```

-continued

```
Pro Gln Phe Arg Asp Asp Tyr Phe Pro Pro Gly Asp Thr Asp Ser Ser
1665                1670                1675                1680

Ser Gly Ile Val Leu His Met Gly Glu Ala Thr Asp Asn Lys Pro Val
            1685                1690                1695

Thr Thr His Gly Asn Asn Phe Gly Phe Lys Ser Thr Pro Tyr Leu Pro
                1700                1705                1710

Gln Pro His Pro Lys
        1715

<210> SEQ ID NO 9
<211> LENGTH: 1715
<212> TYPE: PRT
<213> ORGANISM: Bombyx mori

<400> SEQUENCE: 9

Met Gly Val Asp Val Arg Ile Leu Ala Thr Leu Leu Ile Tyr Ala
 1               5                  10                  15

Glu Thr Val Leu Ala Gln Glu Arg Cys Gly Phe Met Val Ala Ile Pro
             20                  25                  30

Arg Pro Arg Pro Asp Leu Pro Glu Leu Asp Phe Glu Gly Gln Thr
         35                  40                  45

Trp Ser Gln Arg Pro Leu Ile Pro Ala Ala Asp Arg Glu Asp Val Cys
 50                  55                  60

Met Asp Gly Tyr His Ala Met Thr Pro Thr Tyr Gly Thr Gln Ile Ile
 65                  70                  75                  80

Tyr Met Glu Glu Ile Glu Gly Val Pro Ile Ala Lys Leu Asn
             85                  90                  95

Tyr Arg Gly Pro Asn Val Pro Tyr Ile Glu Pro Ala Phe Leu Ser Gly
            100                 105                 110

Ser Phe Asn Leu Leu Val Pro Val Ile Arg Arg Ile Pro Asp Ser Asn
            115                 120                 125

Gly Glu Trp His Leu Ile Ile Thr Gln Arg Gln Asp Tyr Glu Thr Pro
130                 135                 140

Gly Met Gln Gln Tyr Val Phe Asn Ile Arg Ile Asp Gly Glu Thr Leu
145                 150                 155                 160

Val Ala Gly Val Ser Leu Leu Ile Val Asn Ile Asp Asp Asn Ala Pro
                165                 170                 175

Ile Ile Gln Ala Leu Glu Pro Cys Gln Val Asp Glu Leu Gly Glu Ala
            180                 185                 190

Arg Leu Thr Glu Cys Val Tyr Val Val Thr Asp Ala Asp Gly Arg Ile
        195                 200                 205

Ser Thr Gln Phe Met Gln Phe Arg Ile Asp Ser Asp Arg Gly Asp Asp
    210                 215                 220

Lys Ile Phe Tyr Ile Gln Gly Ala Asn Ile Pro Gly Glu Trp Ile Arg
225                 230                 235                 240

Met Thr Met Thr Val Gly Ile Asn Glu Pro Leu Asn Phe Glu Thr Asn
                245                 250                 255

Pro Leu His Ile Phe Ser Val Thr Ala Leu Asp Ser Leu Pro Asn Thr
            260                 265                 270

His Thr Val Thr Leu Met Val Gln Val Glu Asn Val Glu His Arg Pro
        275                 280                 285

Pro Arg Trp Val Glu Ile Phe Ala Val Gln Gln Phe Asp Glu Lys Thr
    290                 295                 300

Ala Gln Ser Phe Pro Val Arg Ala Ile Asp Gly Asp Thr Gly Ile Asn
```

-continued

```
            305                 310                 315                 320
Lys Pro Ile His Tyr Arg Leu Glu Thr Ala Glu Glu Asp Thr Phe Phe
                    325                 330                 335
His Ile Arg Thr Ile Glu Gly Gly Arg Ser Gly Ala Ile Leu Tyr Val
                    340                 345                 350
Asp Pro Ile Asp Arg Asp Thr Leu Gln Arg Glu Val Phe Gln Leu Ser
                    355                 360                 365
Ile Ile Ala Tyr Lys Tyr Asp Asn Glu Ser Ser Ala Thr Ala Ala Asn
                    370                 375                 380
Val Val Ile Ile Val Asn Asp Ile Asn Asp Gln Arg Pro Glu Pro Leu
385                 390                 395                 400
Phe Lys Glu Tyr Arg Leu Asn Ile Met Glu Glu Thr Ala Leu Thr Leu
                    405                 410                 415
Asn Phe Asp Gln Glu Phe Gly Phe His Asp Arg Asp Leu Gly Gln Asn
                    420                 425                 430
Ala Gln Tyr Thr Val Arg Leu Glu Ser Asp Tyr Pro Ala Asp Ala Ala
                    435                 440                 445
Lys Ala Phe Tyr Ile Ala Pro Glu Val Gly Tyr Gln Arg Gln Thr Phe
                    450                 455                 460
Ile Met Gly Thr Ala Asn His Lys Met Leu Asp Tyr Glu Val Pro Glu
465                 470                 475                 480
Phe Gln Arg Ile Arg Leu Arg Val Ile Ala Thr Asp Met Asp Asn Glu
                    485                 490                 495
Glu His Val Gly Val Ala Tyr Val Tyr Ile Asn Leu Ile Asn Trp Asn
                    500                 505                 510
Asp Glu Glu Pro Ile Phe Glu His Ser Val Gln Asn Val Ser Phe Lys
                    515                 520                 525
Glu Thr Glu Gly Lys Gly Phe Phe Val Ala Asn Val Arg Ala His Asp
                    530                 535                 540
Arg Asp Ile Asp Asp Arg Val Glu His Thr Leu Met Gly Asn Ala Asn
545                 550                 555                 560
Asn Tyr Leu Ser Ile Asp Lys Asp Thr Gly Asp Ile His Val Thr Gln
                    565                 570                 575
Asp Asp Phe Phe Asp Tyr His Arg Gln Ser Glu Leu Phe Val Gln Val
                    580                 585                 590
Arg Ala Asp Asp Thr Leu Gly Glu Pro Phe His Thr Ala Thr Ser Gln
                    595                 600                 605
Leu Leu Ile His Leu Glu Asp Ile Asn Asn Thr Pro Pro Thr Leu Arg
                    610                 615                 620
Leu Pro Arg Gly Ser Pro Asn Val Glu Glu Asn Val Pro Glu Gly Tyr
625                 630                 635                 640
Ile Ile Thr Ser Glu Ile Arg Ala Thr Asp Pro Asp Thr Thr Ala Glu
                    645                 650                 655
Leu Arg Phe Glu Ile Asp Trp Thr Thr Ser Tyr Ala Thr Lys Gln Gly
                    660                 665                 670
Arg Glu Ala Asn Pro Ile Glu Phe His Asn Cys Val Glu Ile Glu Thr
                    675                 680                 685
Ile Tyr Pro Ala Ile Asn Asn Arg Gly Ser Ala Ile Gly Arg Leu Val
                    690                 695                 700
Val Lys Lys Ile Arg Glu Asn Val Thr Ile Asp Tyr Glu Glu Phe Glu
705                 710                 715                 720
Met Leu Tyr Leu Thr Val Arg Val Arg Asp Leu Asn Thr Val Ile Gly
                    725                 730                 735
```

-continued

```
Asp Asp Tyr Asp Glu Ser Thr Phe Thr Ile Thr Ile Ile Asp Met Asn
            740                 745                 750

Asp Asn Pro Pro Ile Trp Val Pro Gly Thr Leu Glu Gln Ser Leu Arg
            755                 760                 765

Val Arg Glu Met Ser Asp Ala Gly Val Val Ile Gly Thr Leu Thr Ala
            770                 775                 780

Thr Asp Ile Asp Gly Pro Leu Tyr Asn Gln Val Arg Tyr Thr Met Lys
785                 790                 795                 800

Ala Asn Glu Gly Thr Pro Glu Asn Leu Leu Met Ile Asp Phe Tyr Thr
            805                 810                 815

Gly Gln Ile Thr Val Lys Thr Ser Gly Ala Ile Asp Ala Asp Val Pro
            820                 825                 830

Arg Arg Tyr Asn Leu Tyr Tyr Thr Val Ala Thr Asp Arg Cys Tyr
            835                 840                 845

Ala Glu Asp Pro Asp Asp Cys Pro Asp Asp Pro Thr Tyr Trp Glu Thr
            850                 855                 860

Pro Gly Gln Val Val Ile Gln Ile Ile Asp Thr Asn Asn Lys Ile Pro
865                 870                 875                 880

Gln Pro Glu Thr Asp Gln Phe Lys Ala Val Val Tyr Ile Tyr Glu Asp
            885                 890                 895

Ala Val Ser Gly Asp Glu Val Val Lys Val Ile Gly Ser Asp Leu Asp
            900                 905                 910

Arg Asp Asp Ile Tyr His Thr Ile Arg Tyr Gln Ile Asn Tyr Ala Val
            915                 920                 925

Asn Pro Arg Leu Arg Asp Phe Phe Ala Val Asp Pro Asp Thr Gly Arg
            930                 935                 940

Val Tyr Val Tyr Tyr Thr Thr Asp Glu Val Leu Asp Arg Asp Gly Asp
945                 950                 955                 960

Glu Pro Gln His Arg Ile Phe Phe Asn Leu Ile Asp Asn Phe Phe Gln
            965                 970                 975

Gln Gly Asp Gly Asn Arg Asn Gln Asn Asp Ala Glu Val Leu Val Val
            980                 985                 990

Leu Leu Asp Val Asn Asp Asn Ala Pro Glu Leu Pro Glu Pro Asp Glu
            995                 1000                1005

Leu Ser Trp Ser Val Ser Glu Ser Leu Thr Lys Gly Thr Arg Leu Gln
            1010                1015                1020

Pro His Ile Tyr Ala Pro Asp Arg Asp Glu Pro Asp Thr Asp Asn Ser
1025                1030                1035                1040

Arg Val Gly Tyr Ala Ile Ile Ser Leu Thr Ile Ala Asn Arg Glu Ile
            1045                1050                1055

Glu Val Pro Glu Leu Phe Thr Met Ile Gln Ile Gln Asn Val Thr Gly
            1060                1065                1070

Glu Leu Glu Thr Ala Met Asp Leu Arg Gly Tyr Trp Gly Thr Tyr Ala
            1075                1080                1085

Ile His Ile Lys Ala Tyr Asp His Gly Ile Pro Gln Gln Met Ser Asn
            1090                1095                1100

Glu Thr Tyr Glu Leu Val Ile Arg Pro Tyr Asn Phe His Ala Pro Val
1105                1110                1115                1120

Phe Val Phe Pro Lys His Gly Ala Thr Leu Arg Leu Ala Arg Glu Arg
            1125                1130                1135

Ala Val Val Asn Gly Leu Leu Ala Thr Val Asp Gly Glu Phe Leu Asn
            1140                1145                1150
```

-continued

Arg Ile Val Ala Thr Asp Glu Asp Gly Leu His Ala Gly Gln Val Ala
    1155                1160                1165

Phe Glu Val Val Gly Asp Thr Glu Ala Val Asp Tyr Phe His Ile Val
1170                1175                1180

Asn Asp Gly Glu Asn Ser Gly Thr Leu Met Leu Lys Gln Leu Phe Pro
1185                1190                1195                1200

Glu Asp Ile Arg Glu Phe Glu Val Thr Ile Arg Ala Thr Asp Gly Gly
            1205                1210                1215

Thr Glu Pro Arg Pro Leu Ser Thr Asp Cys Thr Phe Ser Val Val Phe
                1220                1225                1230

Val Pro Ile Gln Gly Glu Pro Ile Phe Pro Thr Ser Thr His Thr Val
        1235                1240                1245

Ala Phe Ile Glu Lys Glu Ala Gly Leu Leu Glu Arg His Glu Leu Pro
    1250                1255                1260

Arg Ala Glu Asp Arg Lys Asn His Leu Cys Ser Asp Cys His Asn
1265                1270                1275                1280

Ile Tyr Tyr Arg Ile Ile Asp Gly Asn Asn Asp Gly His Phe Gly Leu
            1285                1290                1295

Asp Glu Thr Thr Asn Val Leu Phe Leu Val Lys Glu Leu Asp Arg Ser
                1300                1305                1310

Val Ser Glu Thr Tyr Thr Leu Thr Ile Ala Ala Ser Asn Ser Pro Thr
        1315                1320                1325

Gly Gly Ile Ala Leu Thr Ser Thr Ile Thr Ile Thr Val Asn Val Arg
    1330                1335                1340

Glu Ala Asp Pro Gln Pro Tyr Phe Val Arg Asp Leu Tyr Thr Ala Gly
1345                1350                1355                1360

Ile Ser Thr Ser Asp Ser Ile Asn Arg Glu Leu Leu Ile Leu Gln Ala
            1365                1370                1375

Thr His Ser Glu Asn Ala Pro Ile Ile Tyr Thr Ile Asp Trp Ser Thr
                1380                1385                1390

Met Val Thr Asp Pro Thr Leu Ala Ser Val Arg Glu Thr Ala Phe Ile
        1395                1400                1405

Leu Asn Pro His Thr Gly Val Leu Thr Leu Asn Ile Gln Pro Thr Ala
    1410                1415                1420

Ser Met His Gly Met Phe Glu Phe Gln Val Val Ala Thr Asp Pro Ala
1425                1430                1435                1440

Gly Tyr Ser Asp Arg Ala Asn Val Lys Ile Tyr Leu Ile Ser Thr Arg
            1445                1450                1455

Asn Arg Val Phe Phe Leu Phe Val Asn Thr Leu Glu Gln Val Glu Gln
                1460                1465                1470

Asn Thr Asp Phe Ile Ala Gln Thr Phe Ser Ala Gly Phe Glu Met Thr
        1475                1480                1485

Cys Asn Ile Asp Gln Val Val Pro Ala Thr Asp Ala Ser Gly Val Ile
    1490                1495                1500

Met Asn Gly Ile Thr Glu Val Arg Gly His Phe Ile Arg Asp Asn Val
1505                1510                1515                1520

Pro Val Pro Ala Asp Glu Ile Glu Thr Leu Arg Gly Asp Met Val Leu
            1525                1530                1535

Leu Thr Ala Ile Gln Ser Thr Leu Ala Thr Arg Leu Leu Val Leu Arg
                1540                1545                1550

Asp Leu Phe Thr Asp Thr Ser Pro Ala Pro Asp Ala Gly Ser Ala Ala
        1555                1560                1565

Val Leu Tyr Ala Leu Ala Val Leu Ser Ala Leu Leu Ala Ala Leu Cys

```
                        1570              1575             1580
Leu Leu Leu Leu Val Ile Phe Ile Ile Arg Thr Lys Lys Leu Asn Arg
1585                1590                1595                1600

Arg Leu Glu Ala Leu Thr Val Lys Lys Tyr Gly Ser Val Asp Ser Gly
                1605                1610                1615

Leu Asn Arg Val Gly Ile Ala Ala Pro Gly Thr Asn Lys His Ala Val
                1620                1625                1630

Glu Gly Ser Asn Pro Ile Trp Asn Glu Thr Ile Lys Ala Pro Asp Phe
                1635                1640                1645

Asp Ser Met Ser Asp Ala Ser Asn Asp Ser Asp Leu Ile Gly Ile Glu
1650                1655                1660

Asp Leu Pro His Phe Gly Glu Asn Asn Tyr Phe Pro Arg Asp Val Asp
1665                1670                1675                1680

Glu Phe Lys Thr Asp Lys Pro Glu Asp Ile Val Ala Thr His Asn Asn
                1685                1690                1695

Asn Phe Gly Phe Lys Ser Thr Pro Phe Ser Pro Glu Phe Ala Asn Gln
                1700                1705                1710

Phe Gln Lys
        1715

<210> SEQ ID NO 10
<211> LENGTH: 1717
<212> TYPE: PRT
<213> ORGANISM: Manduca sexta

<400> SEQUENCE: 10

Met Ala Val Asp Val Arg Ile Ala Ala Phe Leu Leu Val Phe Ile Ala
1               5                   10                  15

Pro Ala Val Leu Ala Gln Glu Arg Cys Gly Tyr Met Thr Ala Ile Pro
                20                  25                  30

Arg Leu Pro Arg Pro Asp Asn Leu Pro Val Leu Asn Phe Glu Gly Gln
            35                  40                  45

Thr Trp Ser Gln Arg Pro Leu Leu Pro Ala Pro Glu Arg Asp Asp Leu
    50                  55                  60

Cys Met Asp Ala Tyr His Val Ile Thr Ala Asn Leu Gly Thr Gln Val
65                  70                  75                  80

Ile Tyr Met Asp Glu Glu Ile Glu Asp Glu Ile Thr Ile Ala Ile Leu
                85                  90                  95

Asn Tyr Asn Gly Pro Ser Thr Pro Phe Ile Glu Leu Pro Phe Leu Ser
            100                 105                 110

Gly Ser Tyr Asn Leu Leu Met Pro Val Ile Arg Arg Val Asp Asn Gly
        115                 120                 125

Glu Trp His Leu Ile Ile Thr Gln Arg Gln His Tyr Glu Leu Pro Gly
    130                 135                 140

Met Gln Gln Tyr Met Phe Asn Val Arg Val Asp Gly Gln Ser Leu Val
145                 150                 155                 160

Ala Gly Val Ser Leu Ala Ile Val Asn Ile Asp Asp Asn Ala Pro Ile
                165                 170                 175

Ile Gln Asn Phe Glu Pro Cys Arg Val Pro Glu Leu Gly Glu Pro Gly
            180                 185                 190

Leu Thr Glu Cys Thr Tyr Gln Val Ser Asp Ala Asp Gly Arg Ile Ser
        195                 200                 205

Thr Glu Phe Met Thr Phe Arg Ile Asp Ser Val Arg Gly Asp Glu Glu
    210                 215                 220
```

```
Thr Phe Tyr Ile Glu Arg Thr Asn Ile Pro Asn Gln Trp Met Trp Leu
225                 230                 235                 240

Asn Met Thr Ile Gly Val Asn Thr Ser Leu Asn Phe Val Thr Ser Pro
            245                 250                 255

Leu His Ile Phe Ser Val Thr Ala Leu Asp Ser Leu Pro Asn Thr His
            260                 265                 270

Thr Val Thr Met Met Val Gln Val Ala Asn Val Asn Ser Arg Pro Pro
        275                 280                 285

Arg Trp Leu Glu Ile Phe Ala Val Gln Gln Phe Glu Glu Lys Ser Tyr
290                 295                 300

Gln Asn Phe Thr Val Arg Ala Ile Asp Gly Asp Thr Glu Ile Asn Met
305                 310                 315                 320

Pro Ile Asn Tyr Arg Leu Ile Thr Asn Glu Glu Asp Thr Phe Phe Ser
                325                 330                 335

Ile Glu Ala Leu Pro Gly Gly Lys Ser Gly Ala Val Phe Leu Val Ser
            340                 345                 350

Pro Ile Asp Arg Asp Thr Leu Gln Arg Glu Val Phe Pro Leu Thr Ile
            355                 360                 365

Val Ala Tyr Lys Tyr Asp Glu Glu Ala Phe Ser Thr Ser Thr Asn Val
370                 375                 380

Val Ile Ile Val Thr Asp Ile Asn Asp Gln Arg Pro Glu Pro Ile His
385                 390                 395                 400

Lys Glu Tyr Arg Leu Ala Ile Met Glu Glu Thr Pro Leu Thr Leu Asn
                405                 410                 415

Phe Asp Lys Glu Phe Gly Phe His Asp Lys Asp Leu Gly Gln Asn Ala
            420                 425                 430

Gln Tyr Thr Val Arg Leu Glu Ser Val Asp Pro Pro Gly Ala Ala Glu
            435                 440                 445

Ala Phe Tyr Ile Ala Pro Glu Val Gly Tyr Gln Arg Gln Thr Phe Ile
450                 455                 460

Met Gly Thr Leu Asn His Ser Met Leu Asp Tyr Glu Val Pro Glu Phe
465                 470                 475                 480

Gln Ser Ile Thr Ile Arg Val Val Ala Thr Asp Asn Asn Asp Thr Arg
                485                 490                 495

His Val Gly Val Ala Leu Val His Ile Asp Leu Ile Asn Trp Asn Asp
            500                 505                 510

Glu Gln Pro Ile Phe Glu His Ala Val Gln Thr Val Thr Phe Asp Glu
            515                 520                 525

Thr Glu Gly Glu Gly Phe Phe Val Ala Lys Ala Val Ala His Asp Arg
530                 535                 540

Asp Ile Gly Asp Val Val Glu His Thr Leu Leu Gly Asn Ala Val Asn
545                 550                 555                 560

Phe Leu Thr Ile Asp Lys Leu Thr Gly Asp Ile Arg Val Ser Ala Asn
                565                 570                 575

Asp Ser Phe Asn Tyr His Arg Glu Ser Glu Leu Phe Val Gln Val Arg
            580                 585                 590

Ala Thr Asp Thr Leu Gly Glu Pro Phe His Thr Ala Thr Ser Gln Leu
            595                 600                 605

Val Ile Arg Leu Asn Asp Ile Asn Asn Thr Pro Pro Thr Leu Arg Leu
610                 615                 620

Pro Arg Gly Ser Pro Gln Val Glu Glu Asn Val Pro Asp Gly His Val
625                 630                 635                 640

Ile Thr Gln Glu Leu Arg Ala Thr Asp Pro Asp Thr Thr Ala Asp Leu
```

-continued

```
                645                 650                 655
Arg Phe Glu Ile Asn Trp Asp Thr Ser Phe Ala Thr Lys Gln Gly Arg
            660                 665                 670
Gln Ala Asn Pro Asp Glu Phe Arg Asn Cys Val Glu Ile Glu Thr Ile
            675                 680                 685
Phe Pro Glu Ile Asn Asn Arg Gly Leu Ala Ile Gly Arg Val Val Ala
            690                 695                 700
Arg Glu Ile Arg His Asn Val Thr Ile Asp Tyr Glu Glu Phe Glu Val
705                 710                 715                 720
Leu Ser Leu Thr Val Arg Val Arg Asp Leu Asn Thr Val Tyr Gly Asp
                725                 730                 735
Asp Tyr Asp Glu Ser Met Leu Thr Ile Thr Ile Ile Asp Met Asn Asp
            740                 745                 750
Asn Ala Pro Val Trp Val Glu Gly Thr Leu Glu Gln Asn Phe Arg Val
            755                 760                 765
Arg Glu Met Ser Ala Gly Gly Leu Val Val Gly Ser Val Arg Ala Asp
            770                 775                 780
Asp Ile Asp Gly Pro Leu Tyr Asn Gln Val Arg Tyr Thr Ile Phe Pro
785                 790                 795                 800
Arg Glu Asp Thr Asp Lys Asp Leu Ile Met Ile Asp Phe Leu Thr Gly
                805                 810                 815
Gln Ile Ser Val Asn Thr Ser Gly Ala Ile Asp Ala Asp Thr Pro Pro
            820                 825                 830
Arg Phe His Leu Tyr Tyr Thr Val Val Ala Ser Asp Arg Cys Ser Thr
            835                 840                 845
Glu Asp Pro Ala Asp Cys Pro Pro Asp Pro Thr Tyr Trp Glu Thr Glu
            850                 855                 860
Gly Asn Ile Thr Ile His Ile Thr Asp Thr Asn Asn Lys Val Pro Gln
865                 870                 875                 880
Ala Glu Thr Thr Lys Phe Asp Thr Val Val Tyr Ile Tyr Glu Asn Ala
                885                 890                 895
Thr His Leu Asp Glu Val Val Thr Leu Ile Ala Ser Asp Leu Asp Arg
            900                 905                 910
Asp Glu Ile Tyr His Thr Val Ser Tyr Val Ile Asn Tyr Ala Val Asn
            915                 920                 925
Pro Arg Leu Met Asn Phe Phe Ser Val Asn Arg Glu Thr Gly Leu Val
            930                 935                 940
Tyr Val Asp Tyr Glu Thr Gln Gly Ser Gly Glu Val Leu Asp Arg Asp
945                 950                 955                 960
Gly Asp Glu Pro Thr His Arg Ile Phe Phe Asn Leu Ile Asp Asn Phe
                965                 970                 975
Met Gly Glu Gly Glu Gly Asn Arg Asn Gln Asn Asp Thr Glu Val Leu
            980                 985                 990
Val Ile Leu Leu Asp Val Asn Asp Asn Ala Pro Glu Leu Pro Pro Pro
            995                1000                1005
Ser Glu Leu Ser Trp Thr Ile Ser Glu Asn Leu Lys Gln Gly Val Arg
            1010                1015                1020
Leu Glu Pro His Ile Phe Ala Pro Asp Arg Asp Glu Pro Asp Thr Asp
1025                1030                1035                1040
Asn Ser Arg Val Gly Tyr Glu Ile Leu Asn Leu Ser Thr Glu Arg Asp
                1045                1050                1055
Ile Glu Val Pro Glu Leu Phe Val Met Ile Gln Ile Ala Asn Val Thr
            1060                1065                1070
```

```
Gly Glu Leu Glu Thr Ala Met Asp Leu Lys Gly Tyr Trp Gly Thr Tyr
        1075                1080                1085
Ala Ile His Ile Arg Ala Phe Asp His Gly Ile Pro Gln Met Ser Met
        1090                1095                1100
Asn Glu Thr Tyr Glu Leu Ile Ile His Pro Phe Asn Tyr Tyr Ala Pro
1105                1110                1115                1120
Glu Phe Val Phe Pro Thr Asn Asp Ala Val Ile Arg Leu Ala Arg Glu
                1125                1130                1135
Arg Ala Val Ile Asn Gly Val Leu Ala Thr Val Asn Gly Glu Phe Leu
            1140                1145                1150
Glu Arg Ile Ser Ala Thr Asp Pro Asp Gly Leu His Ala Gly Val Val
            1155                1160                1165
Thr Phe Gln Val Val Gly Asp Glu Glu Ser Gln Arg Tyr Phe Gln Val
        1170                1175                1180
Val Asn Asp Gly Glu Asn Leu Gly Ser Leu Arg Leu Leu Gln Ala Val
1185                1190                1195                1200
Pro Glu Glu Ile Arg Glu Phe Arg Ile Thr Ile Arg Ala Thr Asp Gln
                1205                1210                1215
Gly Thr Asp Pro Gly Pro Leu Ser Thr Asp Met Thr Phe Arg Val Val
            1220                1225                1230
Phe Val Pro Thr Gln Gly Glu Pro Arg Phe Ala Ser Ser Glu His Ala
            1235                1240                1245
Val Ala Phe Ile Glu Lys Ser Ala Gly Met Glu Glu Ser His Gln Leu
        1250                1255                1260
Pro Leu Ala Gln Asp Ile Lys Asn His Leu Cys Glu Asp Cys His
1265                1270                1275                1280
Ser Ile Tyr Tyr Arg Ile Ile Asp Gly Asn Ser Glu Gly His Phe Gly
                1285                1290                1295
Leu Asp Pro Val Arg Asn Arg Leu Phe Leu Lys Lys Glu Leu Ile Arg
            1300                1305                1310
Glu Gln Ser Ala Ser His Thr Leu Gln Val Ala Ala Ser Asn Ser Pro
        1315                1320                1325
Asp Gly Gly Ile Pro Leu Pro Ala Ser Ile Leu Thr Val Thr Val Thr
        1330                1335                1340
Val Arg Glu Ala Asp Pro Arg Pro Val Phe Val Arg Glu Leu Tyr Thr
1345                1350                1355                1360
Ala Gly Ile Ser Thr Ala Asp Ser Ile Gly Arg Glu Leu Leu Arg Leu
            1365                1370                1375
His Ala Thr Gln Ser Glu Gly Ser Ala Ile Thr Tyr Ala Ile Asp Tyr
        1380                1385                1390
Asp Thr Met Val Val Asp Pro Ser Leu Glu Ala Val Arg Gln Ser Ala
        1395                1400                1405
Phe Val Leu Asn Ala Gln Thr Gly Val Leu Thr Leu Asn Ile Gln Pro
        1410                1415                1420
Thr Ala Thr Met His Gly Leu Phe Lys Phe Glu Val Thr Ala Thr Asp
1425                1430                1435                1440
Thr Ala Gly Ala Gln Asp Arg Thr Asp Val Thr Val Tyr Val Val Ser
            1445                1450                1455
Ser Gln Asn Arg Val Tyr Phe Val Phe Val Asn Thr Leu Gln Gln Val
        1460                1465                1470
Glu Asp Asn Arg Asp Phe Ile Ala Asp Thr Phe Ser Ala Gly Phe Asn
        1475                1480                1485
```

-continued

```
Met Thr Cys Asn Ile Asp Gln Val Val Pro Ala Asn Asp Pro Val Thr
    1490            1495                1500
Gly Val Ala Leu Glu His Ser Thr Gln Met Arg Gly His Phe Ile Arg
1505            1510                1515                1520
Asp Asn Val Pro Val Leu Ala Asp Glu Ile Glu Gln Ile Arg Ser Asp
                1525                1530                1535
Leu Val Leu Leu Ser Ser Ile Gln Thr Thr Leu Ala Ala Arg Ser Leu
            1540                1545                1550
Val Leu Gln Asp Leu Leu Thr Asn Ser Ser Pro Asp Ser Ala Pro Asp
        1555                1560                1565
Ser Ser Leu Thr Val Tyr Val Leu Ala Ser Leu Ser Ala Val Leu Gly
    1570                1575                1580
Phe Met Cys Leu Val Leu Leu Leu Thr Phe Ile Ile Arg Thr Arg Ala
1585            1590                1595                1600
Leu Asn Arg Arg Leu Glu Ala Leu Ser Met Thr Lys Tyr Gly Ser Leu
                1605                1610                1615
Asp Ser Gly Leu Asn Arg Ala Gly Ile Ala Ala Pro Gly Thr Asn Lys
            1620                1625                1630
His Thr Val Glu Gly Ser Asn Pro Ile Phe Asn Glu Ala Ile Lys Thr
        1635                1640                1645
Pro Asp Leu Asp Ala Ile Ser Glu Gly Ser Asn Asp Ser Asp Leu Ile
    1650                1655                1660
Gly Ile Glu Asp Leu Pro His Phe Gly Asn Val Phe Met Asp Pro Glu
1665            1670                1675                1680
Val Asn Glu Lys Ala Asn Gly Tyr Pro Glu Val Ala Asn His Asn Asn
                1685                1690                1695
Asn Phe Ala Phe Asn Pro Thr Pro Phe Ser Pro Glu Phe Val Asn Gly
            1700                1705                1710
Gln Phe Arg Lys Ile
        1715
```

BT TOXIN RECEPTORS AND METHODS OF USE

CROSS-REFERENCE TO RELATED APPLICATIONS

This application is a divisional application of U.S. Utility application Ser. No. 10/798,058, filed Mar. 11, 2004, which claims the benefit of U.S. Provisional Application Ser. No. 60/455,085, filed Mar. 14, 2003, the contents of which are herein incorporated by reference in their entirety.

FIELD OF THE INVENTION

The present invention is directed to the manipulation of Bt toxin susceptibility in plant pests. The present invention relates to the isolation and characterization of nucleic acid and polypeptides for a novel Bt toxin receptor. The nucleic acid and polypeptides are useful in developing new insecticides.

BACKGROUND OF THE INVENTION

Traditionally, growers have used chemical pesticides as a means to control agronomically important pests. The introduction of transgenic plants carrying the delta-endotoxin from *Bacillus thuringiensis* (Bt) afforded a non-chemical method of control. Bt toxins have traditionally been categorized by their specific toxicity towards specific insect categories. For example, the Cry1 group of toxins are toxic to *Lepidoptera* The Cry1 group includes, but is not limited to, Cry1A(a), Cry1A(b) and Cry1A(c). See Hofte et al (1989) *Microbiol Rev* 53: 242–255.

Lepidopteran insects cause considerable damage to maize crops throughout North America and the world. One of the leading pests is *Ostrinia nubilalis*, commonly called the European corn borer (ECB). Genes encoding the crystal proteins Cry1A(b) and Cry1A(c) from Bt have been introduced into maize as a means of ECB control. These transgenic maize hybrids have been effective in control of ECB. However, developed resistance to Bt toxins presents a challenge in pest control. See McGaughey et al. (1998) *Nature Biotechnology* 16: 144–146; Estruch et al. (1997) *Nature Biotechnology* 15:137–141; Roush et al. (1997) *Nature Biotechnology* 15 816–817; and Hofte et al. (1989) *Microbiol. Rev.* 53: 242–255.

The primary site of action of Cry1 toxins is in the brush border membranes of the midgut epithelia of susceptible insect larvae such as lepidopteran insects. Cry1A toxin binding polypeptides have been characterized from a variety of *Lepidopteran* species. A Cry1A(c) binding polypeptide with homology to an aminopeptidase N has been reported from *Manduca sexta, Lymantria dispar, Helicoverpa zea* and *Heliothis virescens*. See Knight et al (1994) *Mol Micro* 11: 429–436; Lee et al. (1996) *Appl Environ Micro* 63: 2845–2849; Gill et al. (1995) *J Biol. Chem* 270: 27277–27282; and Garczynski et al. (1991) *Appl Environ Microbiol* 10: 2816–2820.

Another Bt toxin binding polypeptide (BTR1) cloned from *M. sexta* has homology to the cadherin polypeptide superfamily and binds Cry1A(a), Cry1A(b) and Cry1A(c). See Vadlamudi et al. (1995) *J Biol Chem* 270(10):5490–4, Keeton et al. (1998) *Appl Environ Microbiol* 64(6):2158–2165; Keeton et al. (1997) *Appl Environ Microbiol* 63(9):3419–3425 and U.S. Pat. No. 5,693,491.

A homologue of BTR1 that demonstrates binding to Cry1A(a) was isolated from *Bombyx mori* as described in Ihara et al. (1998) *Comparative Biochemistry and Physiology, Part B* 120:197–204 and Nagamatsu et al. (1998) *Biosci. Biotechnol. Biochem.* 62(4):727–734. In addition, a Bt-binding protein that is also a member of the cadherin superfamily was isolated from *Heliothis virescens*, the tobacco budworm (see Gahan et al. (2001) *Science* 293: 857–860 and GenBank accession number AF367362).

Identification of the plant pest binding polypeptides for Bt toxins are useful for investigating Bt toxin-Bt toxin receptor interactions, selecting and designing improved toxins, developing novel insecticides, and new Bt toxin resistance management strategies.

SUMMARY OF THE INVENTION

Compositions and methods for modulating susceptibility of a cell to Bt toxins are provided. The compositions include Bt toxin receptor polypeptides and fragments and variants thereof, from the lepidopteran insect black cutworm moth (BCW, *Agrotis ipsilon*). Nucleic acids encoding the polypeptides, antibodies specific to the polypeptides, and nucleic acid constructs for expressing the polypeptides in cells of interest are also provided.

The methods are useful for investigating the structure-function relationships of Bt toxin receptors; investigating the toxin-receptor interactions; elucidating the mode of action of Bt toxins; screening and identifying novel Bt toxin receptor ligands including novel insecticidal toxins; and designing and developing novel Bt toxin receptor ligands.

The methods are useful for managing Bt toxin resistance in plant pests, and for protecting plants against damage by plant pests.

BRIEF DESCRIPTION OF THE DRAWINGS

FIGS. 2A–F shows the alignment of the *Agrotis ipsilon* Bt toxin receptor sequence (SEQ ID NO:2) with homologous Bt receptor sequences from *Spodoptera frugiperda* (SEQ ID NO:6), *Helicoverpa zea* (SEQ ID NO:7), *Ostrinia nubilalis* (SEQ ID NO:8), *Bombyx mori* (SEQ ID NO:9), and *Manduca Sexta* (SEQ ID NO:10). The putative signal peptide region, Cry1A binding domain, transmembrane region, and cadherin motifs are identified.

DETAILED DESCRIPTION OF THE INVENTION

Figure 1:
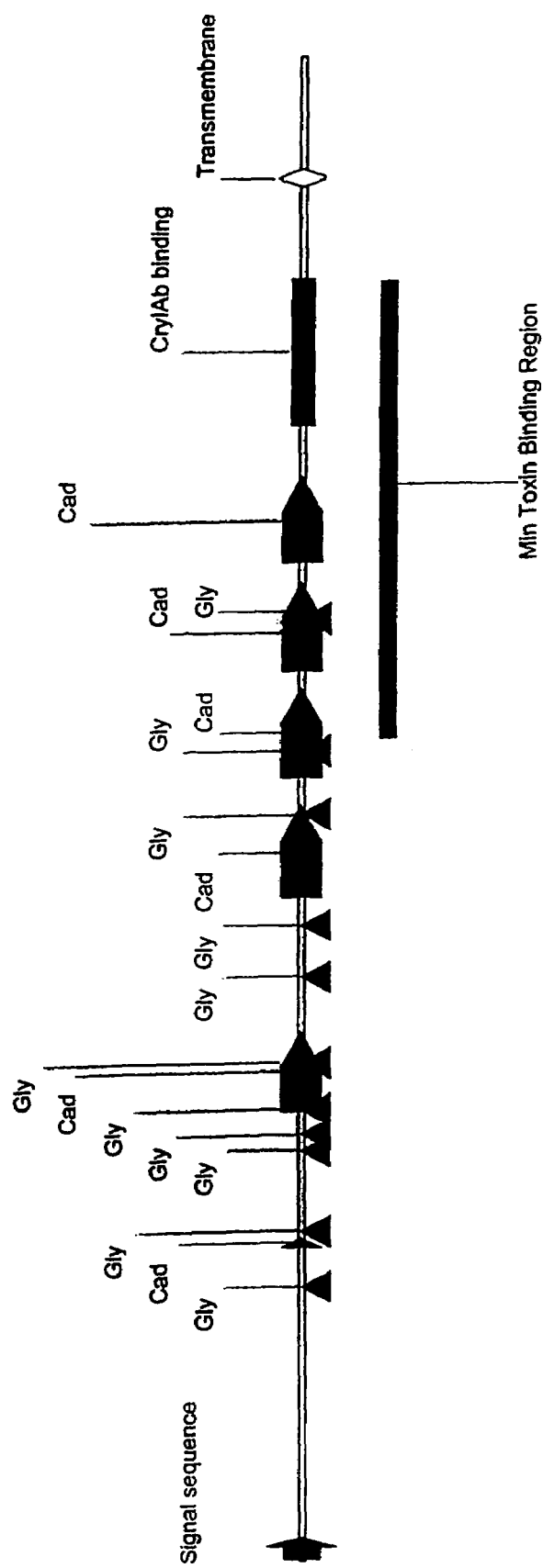
FIG. 1 schematically depicts the location of the signal sequence, putative glycosilation sites, cadherin-like domains, transmembrane segment, Cry1A binding region and toxin binding region of the Bt toxin receptor from *Agrotis ipsilon*; the nucleotide sequence of the receptor set forth in SEQ ID NO:1 and the corresponding deduced amino acid sequence in SEQ ID NO:2.

The invention is directed to novel receptor polypeptides that bind Bt toxin, the receptor being derived from the order *lepidoptera*. The receptors of the invention include those receptor polypeptides that bind Bt toxin and are derived from the lepidopteran superfamily Noctuoidea and particularly from the species *Agrotis*, specifically *Agrotis ipsilon*. The polypeptides have homology to members of the cadherin superfamily of proteins.

Accordingly, compositions of the invention include isolated polypeptides that are involved in Bt toxin binding. In particular, the present invention provides for isolated nucleic acid molecules comprising nucleotide sequences encoding the amino acid sequence shown in SEQ ID NO: 2; or the nucleotide sequence having the cDNA insert of the a plasmid deposited in a bacterial host as Patent Deposit No. PTA-4935. Further provided are polypeptides having an amino acid sequence encoded by a nucleic acid molecule described herein, for example the nucleotide sequence set forth in SEQ ID NO:1, the nucleotide sequence deposited in a plasmid in a bacterial host as Patent Deposit No. PTA-4935, and fragments and variants thereof.

A plasmid containing the nucleotide sequence of the invention was deposited with the Patent Depository of the American Type Culture Collection (ATCC), Manassas, Va. on Jan. 15, 2003 and assigned Patent Deposit No. PTA-4935. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The term "nucleic acid" refers to all forms of DNA such as cDNA or genomic DNA and RNA such as mRNA, as well as analogs of the DNA or RNA generated using nucleotide analogs. The nucleic acid molecules can be single stranded or double stranded. Strands can include the coding or non-coding strand.

The invention encompasses isolated or substantially purified nucleic acid or polypeptide compositions. An "isolated" or "purified" nucleic acid molecule or polypeptide, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably polypeptide encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A polypeptide that is substantially free of cellular material includes preparations of polypeptide having less than about 30%, 20%, 10%, 5%, (by dry weight) of contaminating polypeptide. When the polypeptide of the invention or biologically active portion thereof is recombinantly produced, the culture medium may represent less than about 30%, 20%, 10%, or 5% (by dry weight) of chemical precursors or non-polypeptide-of-interest chemicals.

It is understood, however, that there are embodiments in which preparations that do not contain the substantially pure polypeptide may also be useful. Thus, less pure preparations can be useful where the contaminating material does not interfere with the specific desired use of the peptide. The compositions of the invention also encompass fragments and variants of the disclosed nucleotide sequences and the polypeptides encoded thereby.

The compositions of the invention are useful for, among other uses, expressing the receptor polypeptides in cells of interest to produce cellular or isolated preparations of the polpeptides for investigating the structure-function relationships of Bt toxin receptors, investigating the toxin-receptor interactions, elucidating the mode of action of Bt toxins, screening test compounds to identify novel Bt toxin receptor ligands including novel insecticidal toxins, and designing and developing novel Bt toxin receptor ligands including novel insecticidal toxins.

The isolated nucleotide sequences encoding the receptor polypeptides of the invention are expressed in a cell of interest; and the Bt toxin receptor polypeptides produced by the expression is utilized in intact cell or in-vitro receptor binding assays, and/or intact cell toxicity assays. Methods and conditions for Bt toxin binding and toxicity assays are known in the art and include but are not limited to those described in U.S. Pat. No. 5,693,491; T. P. Keeton et al. (1998) *Appl. Environ. Microbiol.* 64(6):2158–2165; B. R. Francis et al. (1997) *Insect Biochem. Mol. Biol.* 27(6): 541–550; T. P. Keeton et al: (1997) *Appl. Environ. Microbiol.* 63(9):3419–3425; R. K. Vadlamudi et al. (1995) *J. Biol. Chem.* 270(10):5490–5494; Ihara et al. (1998) *Comparative Biochem. Physiol. B* 120:197–204; and Nagamatsu et al. (1998) *Biosci. Biotechnol. Biochem.* 62(4):727–734, herein incorporated by reference. Such methods could be modified by one of ordinary skill in the art to develop assays utilizing the polypeptides of the invention.

By "cell of interest" is intended any cell in which expression of the polypeptides of the invention is desired. Cells of interest include, but are not limited to mammalian, avian, insect, plant, bacteria, fungi and yeast cells. Cells of interest include but are not limited to cultured cell lines, primary cell cultures, cells in vivo, and cells of transgenic organisms.

The methods of the invention encompass using the polypeptides encoded by the nucleotide sequences of the invention in receptor binding and/or toxicity assays to screen test compounds to identify novel Bt toxin receptor ligands, including receptor agonists and antagonists. Test compounds include molecules available from diverse libraries of small molecules created by combinatorial synthetic methods. Test compounds also include, but are not limited to antibodies, peptides, and other small molecules designed or deduced to interact with the receptor polypeptides of the invention. Test compounds include but are not limited to peptide fragments of the receptor, anti-receptor antibodies, antiidiotypic antibodies mimicking one or more receptor binding domains of a toxin, fusion proteins produced by combining two or more toxins or fragments thereof, and the like. Ligands identified by the screening methods of the invention include potential novel insecticidal toxins, the insecticidal activity of which can be determined by known methods; for example, as described in U.S. Pat. Nos. 5,407,454, 5,986,177, and 6,232,439; each of which is herein incorporated by reference in its entirety.

The invention provides methods for screening for ligands that bind to the polypeptides described herein. Both the polypeptides and relevant fragments thereof (for example, the toxin binding domain) can be used to screen by assay for compounds that bind to the receptor and exhibit desired binding characteristics. Desired binding characteristics include, but are not limited to binding affinity, binding site specificity, association and dissociation rates, and the like. The screening assays can be conducted in intact cells or in in vitro assays which include exposing a ligand binding domain to a sample ligand and detecting the formation of a ligand-binding polypeptide complex. The assays could be direct ligand-receptor binding assays or ligand competition assays.

In one embodiment, the methods comprise providing at least one Bt toxin receptor polypeptide of the invention, contacting the polypeptide with a sample and a control ligand under conditions promoting binding; and determining binding characteristics of sample ligands, relative to control ligands. The methods encompass any method known to the skilled artisan that can be used to provide the polypeptides of the invention in a binding assay. For in vitro binding assays, the polypeptide may be provided as isolated, lysed, or homogenized cellular preparations. Isolated polypeptides may be provided in solution, or immobilized to a matrix. Methods for immobilizing polypeptides are well known in the art, and include but are not limited to construction and use of fusion polypeptides with commercially available high affinity ligands. For example, GST fusion proteins can be adsorbed onto glutathione sepharose beads (Sigma Chemical, St. Louis, Mo.) or glutathione derivatized microtitre plates. The polypeptides can also be immobilized utilizing well techniques in the art utilizing conjugation of biotin and streptavidin. The polypeptides can also be immobilized utilizing well known techniques in the art utilizing chemical conjugation (linking) of polypeptides to a matrix. Alternatively, the polypeptides may be provided in intact cell binding assays in which the polypeptides are generally expressed as cell surface Bt toxin receptors.

The invention provides methods utilizing intact cell toxicity assays to screen for ligands that bind to the receptor polypeptides described herein and confer toxicity upon a cell of interest expressing the polypeptide. A ligand selected by this screening is a potential insecticidal toxin to insects expressing the receptor polypeptides, particularly enterally. This deduction is premised on theories that the insect specificity of a particular Bt toxin is determined by the presence of the receptor in specific insect species, or that binding of the toxins is specific for the receptor of some insect species and is bind is insignificant or nonspecific for other variant receptors. See, for example Hofte et al. (1989) *Microbiol Rev* 53: 242–255. The toxicity assays include exposing, in intact cells expressing a polypeptide of the invention, the toxin binding domain of the polypeptide to a sample ligand and detecting the toxicity effected in the cell expressing the polypeptide. By "toxicity" is intended the decreased viability of a cell. By "viability" is intended the ability of a cell to proliferate and/or differentiate and/or maintain its biological characteristics in a manner characteristic of that cell in the absence of a particular cytotoxic agent.

In one embodiment, the methods of the present invention comprise providing at least one cell surface Bt toxin receptor polypeptide of the invention comprising an extracellular toxin binding domain, contacting the polypeptide with a sample and a control ligand under conditions promoting binding, and determining the viability of the cell expressing the cell surface Bt toxin receptor polypeptide, relative to the control ligand.

By "contacting" is intended that the sample and control agents are presented to the intended ligand binding site of the polypeptides of the invention.

By "conditions promoting binding" is intended any combination of physical and biochemical conditions that enables a ligand of the polypeptides of the invention to determinably bind the intended polypeptide over background levels. Examples of such conditions for binding of Cry1 toxins to Bt toxin receptors, as well as methods for assessing the binding, are known in the art and include but are not limited to those described in Keeton et al. (1998) *Appl Environ Microbiol* 64(6): 2158–2165; Francis et al. (1997) *Insect Biochem Mol Biol* 27(6):541–550; Keeton et al. (1997) *Appl Environ Microbiol* 63(9):3419–3425; Vadlamudi et al. (1995) *J Biol Chem* 270(10):5490–5494; Ihara et al. (1998) *Comparative Biochemistry and Physiology, Part B* 120: 197–204; and Nagamatsu et al. (1998) *Biosci. Biotechnol. Biochem.* 62(4):727–734; the contents of which are herein incorporated by reference. In this aspect of the present invention, known and commercially available methods for studying protein—protein interactions, such as yeast and/or bacterial two-hybrid systems could also be used. Two-hybrid systems are available from, for example, Clontech (Palo Alto, Calif.) or Display Systems Biotech Inc. (Vista, Calif.).

The compositions and screening methods of the invention are useful for designing and developing novel Bt toxin receptor ligands including novel insecticidal toxins. Various candidate ligands; ligands screened and characterized for binding, toxicity, and species specificity; and/or ligands having known characteristics and specificities, could be linked or modified to produce novel ligands having particularly desired characteristics and specificities. The methods described herein for assessing binding, toxicity and insecticidal activity could be used to screen and characterize the novel ligands.

In one embodiment of the present invention, the sequences encoding the receptors of the invention, and variants and fragments thereof, are used with yeast and bacterial two-hybrid systems to screen for Bt toxins of interest (for example, more specific and/or more potent toxins), or for insect molecules that bind the receptor and can be used in developing novel insecticides.

By "linked" is intended that a covalent bond is produced between two or more molecules. Known methods that can be used for modification and/or linking of polypeptide ligands such as toxins, include but are not limited to mutagenic and recombinogenic approaches including but not limited to site-directed mutagenesis, chimeric polypeptide construction and DNA shuffling. Such methods are described in further detail below. Known polypeptide modification methods also include methods for covalent modification of polypeptides. "Operably linked" means that the linked molecules carry out the function intended by the linkage.

The compositions and screening methods of the present invention are useful for targeting ligands to cells expressing the receptor polypeptides of the invention. For targeting, secondary polypeptides, and/or small molecules which do not bind the receptor polypeptides of the invention are linked with one or more primary ligands which bind the receptor polypeptides; including but not limited to Cry1A toxin; more particularly Cry1 A(b) toxin or a fragment thereof. By this linkage, any polypeptide and/or small molecule linked to a primary ligand could be targeted to the receptor polypeptide, and thereby to a cell expressing the receptor polypeptide; wherein the ligand binding site is available at the extracellular surface of the cell.

In one embodiment of the invention, at least one secondary polypeptide toxin is linked with a primary Cry1 A toxin capable of binding the receptor polypeptides of the invention to produce a combination toxin that is targeted and toxic to insects expressing the receptor for the primary toxin. Such insects include those of the order *Lepidoptera*, superfamily Noctuoidea and particularly from the species *Agrotis*, for example *Agrotis ipsilon*. Such a combination toxin is particularly useful for eradicating or reducing crop damage by insects that have developed resistance to the primary toxin.

For expression of the Bt toxin receptor polypeptides of the invention in a cell of interest, the Bt toxin receptor sequences are provided in expression cassettes. The cassette will include 5' and 3' regulatory sequences operably linked to a Bt toxin receptor sequence of the invention. In this aspect of the present invention, by "operably linked" is intended a functional linkage between a promoter and a second sequence, wherein the promoter sequence initiates and mediates transcription of the DNA sequence corresponding to the second sequence. In reference to nucleic acids, generally, operably linked means that the nucleic acid sequences being linked are contiguous and, where necessary to join two polypeptide coding regions, contiguous and in the same reading frame. The cassette may additionally contain at least one additional gene to be cotransformed into the organism. Alternatively, the additional gene(s) can be provided on multiple expression cassettes.

Such an expression cassette may be provided with a plurality of restriction sites for insertion of the Bt toxin receptor sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), a Bt toxin receptor nucleotide sequence of the invention, and a transcriptional and translational termination region (i.e., termination region) functional in host cells. The transcriptional initiation region, the promoter, may be native or analogous, or foreign or heterologous to the plant host and/or to the Bt toxin receptor sequence of the invention. Additionally, the promoter may be the natural sequence or alternatively a synthetic sequence. Where the promoter is "foreign" or "heterologous" to the plant host, it intended that the promoter is not found in the native host cells into which the promoter is introduced. Where the promoter is "foreign" or "heterologous" to the Bt toxin receptor sequence of the invention, it is intended that the promoter is not the native or naturally occurring promoter for the operably linked Bt toxin receptor sequence of the invention.

Either heterologous promoters, the native promoter sequences may be used. Such constructs would change expression levels of Bt toxin receptor in the cell of interest. Thus, the phenotype of the cell is altered.

The termination region may be native with the transcriptional initiation region, may be native with the operably linked DNA sequence of interest, may be native with the plant host, or may be derived from another source (i.e., foreign or heterologous to the promoter, the Bt toxin receptor sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acids Res.* 15:9627–9639.

Where appropriate, the gene may be optimized for increased expression in a particular transformed cell of interest. That is, the genes can be synthesized using host cell-preferred codons for improved expression. See, for example, Campbell and Gowri (1990) *Plant Physiol.* 92: 1–11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (encephalomyocarditis 5' noncoding region; Elroy-Stein et al. (1989) *PNAS USA* 86:6126–6130); potyvirus leaders, for example, TEV leader (tobacco etch virus; Allison et al. (1986); MDMV leader (maize dwarf mosaic virus), and human immunoglobulin heavy-chain binding polypeptide (BiP), (Macejak et al. (1991) *Nature* 353:90–94); untranslated leader from the coat polypeptide mRNA of alfalfa mosaic virus (AMV RNA 4); Jobling et al. (1987) *Nature* 325:622–625); tobacco mosaic virus leader (TMV; Gallie et al. (1989) in *Molecular Biology of RNA*, ed. Cech (Liss, New York), pp. 237–256); and maize chlorotic mottle virus leader (MCMV; Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Using the nucleic acids of the present invention, the polypeptides of the invention could be expressed in any cell of interest, the particular choice of the cell depending on factors such as the level of expression and/or receptor activity desired. Cells of interest include, but are not limited to conveniently available mammalian, plant, insect, bacteria, and yeast host cells. The choice of promoter, terminator, and other expression vector components will also depend on the cell chosen. The cells produce the protein in a non-natural condition (e.g., in quantity, composition, location, and/or time), because they have been genetically altered through human intervention to do so.

Those of skill in the art are knowledgeable in the numerous expression systems available for expression of a nucleic acid encoding a protein of the present invention. In brief summary, the expression of isolated nucleic acids encoding a protein of the present invention will typically be achieved by operably linking, for example, the DNA or cDNA to a promoter, followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription or translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al. (1977) *Nature* 198: 1056), the tryptophan (trp) promoter system (Goeddel et al. (1980) *Nucleic Acids Res.* 8:4057) and the lambda-derived P L promoter and N-gene ribosome binding site (Shimatake et al. (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella*. See, Palva et al. (1983) *Gene* 22:229–235 and Mosbach et al. (1983) *Nature* 302:543–545.

A variety of eukaryotic expression systems such as yeast, insect cell lines, plant and mammalian cells, are known to those of skill in the art. The sequences of the present invention can be expressed in these eukaryotic systems. In some embodiments, transformed/transfected plant cells are employed as expression systems for production of the proteins of the instant invention.

Synthesis of heterologous proteins in yeast is well known. See, for example, Sherman, F. et al. (1982) *Methods in Yeast Genetics*, Cold Spring Harbor Laboratory, which describes the various methods available to produce the protein in yeast. Two widely utilized yeast for production of eukaryotic proteins are *Saccharomyces cerevisia* and *Pichia pastoris*. Vectors, strains, and protocols for expression in *Saccharomyces* and *Pichia* are known in the art and available from commercial suppliers (e.g., Invitrogen Life Technologies, Carlsbad, Calif.). Suitable vectors usually have expression control sequences, such as promoters, for example 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay or other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the COS, HEK293, BHK21, and CHO cell lines. Expression vectors for these cells can include expression control sequences, such as an origin of replication, a promoter (e.g., the CMV promoter, the HSV tk promoter or pgk (phosphoglycerate kinase promoter)), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992). One example of mammalian cells for expression of a Bt toxin receptor and assessing Bt toxin cytotoxicity mediated by the receptor, is embryonic 293 cells. See U.S. Pat. No. 5,693,491, herein incorporated by reference.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See Schneider et al. (1987) *J. Embryol. Exp. Morphol.* 27: 353–365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. (1983) *J. Virol.* 45:773–781). Additionally, gene sequences to control replication in the host cell may be incorporated into the vector such as those found in bovine papilloma virus-type vectors. Saveria-Campo, M., Bovine Papilloma Virus DNA a Eukaryotic Cloning Vector in *DNA Cloning Vol. II a Practical Approach*, D. M. Glover, ed., IRL Pres, Arlington, Va. pp. 213–238 (1985).

In a particular embodiment of the invention, it may be desirable to negatively control receptor binding; particularly, when toxicity to a cell is no longer desired or if it is desired to reduce toxicity to a lower level. In this case, ligand-receptor polypeptide binding assays can be used to screen for compounds that bind to the receptor but do not confer toxicity to a cell expressing the receptor. The examples of a molecule that can be used to block ligand binding include an antibody that specifically recognizes the ligand binding domain of the receptor such that ligand binding is decreased or prevented as desired.

In another embodiment, receptor polypeptide expression could be blocked by the use of antisense molecules directed against receptor RNA or ribozymes specifically targeted to this receptor RNA. It is recognized that with the provided nucleotide sequences, antisense constructions, complementary to at least a portion of the messenger RNA (mRNA) for the Bt toxin receptor sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

Fragments and variants of the disclosed nucleotide sequences and polypeptides encoded thereby are encompassed by the present invention. By "fragment" is intended a portion of the nucleotide sequence, or a portion of the amino acid sequence, and hence a portion of the polypeptide encoded thereby. Fragments of a nucleotide sequence may encode polypeptide fragments that retain the biological activity of the native polypeptide and, for example, bind Bt toxins. Alternatively, fragments of a nucleotide sequence that are useful as hybridization probes generally do not encode fragment polypeptides retaining biological activity. Thus, fragments of a nucleotide sequence may range from at least about 20 nucleotides, about 50 nucleotides, about 100 nucleotides, and up to the full-length nucleotide sequence encoding the polypeptides of the invention.

A fragment of a Bt toxin receptor nucleotide sequence that encodes a biologically active portion of a Bt toxin receptor polypeptide of the invention will encode at least 15, 25, 30, 50, 100, 150, 200 or 250 contiguous amino acids, or up to the total number of amino acids present in a full-length Bt toxin receptor polypeptide of the invention (for example, 1759 amino acids for SEQ ID NO:2. Fragments of a Bt toxin receptor nucleotide sequence that are useful as hybridization probes for PCR primers generally need not encode a biologically active portion of a Bt toxin receptor polypeptide.

Thus, a fragment of a Bt toxin receptor nucleotide sequence may encode a biologically active portion of a Bt toxin receptor polypeptide, or it may be a fragment that can be used as a hybridization probe or PCR primer using methods disclosed below. A biologically active portion of a Bt toxin receptor polypeptide can be prepared by isolating a portion of one of the Bt toxin receptor nucleotide sequences of the invention, expressing the encoded portion of the Bt toxin receptor polypeptide (e.g., by recombinant expression in vitro), and assessing the activity of the encoded portion of the Bt toxin receptor polypeptide. Nucleic acid molecules that are fragments of a Bt toxin receptor nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400, 1500, 2000, or 2500 nucleotides, or up to the number of nucleotides present in a full-length Bt toxin receptor nucleotide sequence disclosed herein (for example, 5765 nucleotides for SEQ ID NO:1).

By "variants" is intended substantially similar sequences. For nucleotide sequences, conservative variants include those sequences that, because of the degeneracy of the genetic code, encode the amino acid sequence of one of the Bt toxin receptor polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis, but which still encode a Bt toxin receptor protein of the invention. Generally, variants of a particular nucleotide sequence of the invention will have at least about 40%, 50%, 60%, 65%, 70%, generally at least about 75%, 80%, 85%, 86%, 87%, 88, 89%, such as at least about 90%, 91%, 92%, 93%, 94%, 95%, 96%, 97%, for example at least about 98%, 99% or more sequence identity to that particular nucleotide sequence as determined by sequence alignment programs described elsewhere herein using default parameters.

Variants of a particular nucleotide sequence of the invention (i.e., the reference nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptide of SEQ ID NO: 2 are disclosed. Percent sequence identity between any two polypeptides can be calculated using sequence alignment programs described elsewhere herein using default parameters. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, such as at least about 90%, 91%, 92%, 93%, 94%, 95%, 96%, 97%, for example at least about 98%, 99% or more sequence identity.

Variants of a particular nucleotide sequence of the invention (i.e., the reference nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptide of SEQ ID NO: 2 are disclosed. Percent sequence identity between any two polypeptides can be calculated using sequence alignment programs described elsewhere herein using default parameters. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, activity as described herein (for example, Bt toxin binding activity). Such variants may result from, for example, genetic polymorphism or from human manipulation. Biologically active variants of a native Bt toxin receptor protein of the invention will have at least about 40%, 50%, 60%, 65%, 70%, generally at least about 75%, 80%, 85%, 86%, 87%, 88%, 89%, such as at least about 90%, 91%, 92%, 93%, 94%, 95%, 96%, 97%, for example at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The polypeptides of the invention may be altered in various ways including amino acid substitutions, deletions, truncations, and insertions. Methods for such manipulations are generally known in the art. For example, amino acid sequence variants of the Bt toxin receptor polypeptides can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired toxin binding activity. Obviously, the mutations that will be made in the DNA encoding the variant must not place the sequence out of reading frame and in some embodiments, will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. For example, it is recognized that at least about 10, 20, 50, 100, 150, 200, 250, 300, 350, 400, 450, 500, 550, 600, 650, 700, 750, 800, 850, 900, 950, and up to 960 amino acids may be deleted from the N-terminus of a polypeptide that has the amino acid sequence set forth in SEQ ID NO:2, and still retain binding function. It is further recognized that at least about 10, 20, 30, 40, 50, 60, 70, 80, 90, 100, 110, and up to 119 amino acids may be deleted from the C-terminus of a polypeptide that has the amino acid sequence set forth in SEQ ID NO:2, and still retain binding function. Deletion variants of the invention that encompass polypeptides having these deletions. It is recognized that deletion variants of the invention that retain binding function encompass polypeptides having these N-terminal or C-terminal deletions, or having any deletion combination thereof at both the C- and the N-termini.

However, when it is difficult to predict the exact effect of the substitution, deletion, or insertion in advance of doing so, one skilled in the art will appreciate that the effect will be evaluated by routine screening assays. That is, the activity can be evaluated by receptor binding and/or toxicity assays. See, for example, U.S. Pat. No. 5,693,491; Keeton et al. (1998) *Appl. Environ. Microbiol.* 64(6):2158–2165; Francis et al. (1997) *Insect Biochem. Mol. Biol.* 27(6):541–550; Keeton et al. (1997) *Appl. Environ. Microbiol.* 63(9):3419–3425; Vadlamudi et al. (1995) *J. Biol. Chem.* 270(10):5490–5494; Ihara et al. (1998) *Comparative Biochem. Physiol. B* 120:197–204; and Nagamatsu et al. (1998) *Biosci. Biotechnol. Biochem.* 62(4):727–734; each of which is herein incorporated by reference.

Variant nucleotide sequences and polypeptides also encompass sequences and polypeptides derived from a mutagenic and recombinogenic procedure such as DNA shuffling. With such a procedure, one or more different toxin receptor coding sequences can be manipulated to create a new toxin receptor, including but not limited to a new Bt toxin receptor, possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the Bt toxin receptor gene of the invention and other known Bt toxin receptor genes to obtain a new gene coding for a polypeptide with an improved property of interest, such as an increased ligand affinity in the case of a receptor. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,448.

Where the receptor polypeptides of the invention are expressed in a cell and associated with the cell membrane (for example, by a transmembrane segment), in order for the receptor of the invention to bind a desired ligand, for example a Cry1A toxin, the receptor's ligand binding domain must be available to the ligand. In this aspect, it is recognized that the native Bt toxin receptor of the invention is oriented such that the toxin binding site is available extracellularly.

Accordingly, in methods comprising use of intact cells, the invention provides cell surface Bt-toxin receptors. By a "cell surface Bt toxin receptor" is intended a membrane-bound receptor polypeptide comprising at least one extracellular Bt toxin binding site. A cell surface receptor of the invention comprises an appropriate combination of signal sequences and transmembrane segments for guiding and retaining the receptor at the cell membrane such that that toxin binding site is available extracellularly. Where native Bt toxin receptors are used for expression, deduction of the composition and configuration of the signal sequences and transmembrane segments is not necessary to ensure the appropriate topology of the polypeptide for displaying the toxin binding site extracellularly. As an alternative to native signal and transmembrane sequences, heterologous signal and transmembrane sequences could be utilized to produce a cell surface receptor polypeptide of the invention.

It is recognized that it may be of interest to generate Bt toxin receptors that are capable of interacting with the receptor's ligands intracellularly in the cytoplasm, in the nucleus or other organelles, in other subcellular spaces; or in the extracellular space. Accordingly, the invention encompasses variants of the receptors of the invention, wherein one or more of the segments of the receptor polypeptide is modified to target the polypeptide to a desired intra- or extracellular location.

Also encompassed by the invention are receptor fragments and variants that are useful, among other things, as binding antagonists that will compete with a cell surface receptor of the invention. Such a fragment or variant can, for example, bind a toxin but not be able to confer toxicity to a particular cell. In this aspect, the invention provides secreted Bt toxin receptors, i.e. receptors that are not membrane bound. The secreted receptors of the invention can contain a heterologous or homologous signal sequence facilitating their secretion from the cell expressing the receptors; and further comprise a secretion variation in the region corresponding to transmembrane segments. By "secretion variation" is intended that amino acids corresponding to a transmembrane segment of a membrane bound receptor comprise one or more deletions, substitutions, insertions, or any combination thereof; such that the region no longer retains the requisite hydrophobicity to serve as a transmembrane segment. Sequence alterations to create a secretion variation can be tested by confirming secretion of the polypeptide comprising the variation from the cell expressing the polypeptide.

The polypeptides of the invention can be purified from cells that naturally express them, purified from cells that have been altered to express them (e.g., recombinant host cells) or synthesized using polypeptide synthesis techniques that are well known in the art. In one embodiment, the polypeptide is produced by recombinant DNA methods. In such methods a nucleic acid molecule encoding the polypeptide is cloned into an expression vector as described more fully herein and expressed in an appropriate host cell according to known methods in the art. The polypeptide is then isolated from cells using polypeptide purification techniques well known to those of ordinary skill in the art. Alternatively, the polypeptide or fragment can be synthesized using peptide synthesis methods well known to those of ordinary skill in the art.

The invention also encompasses fusion polypeptides in which one or more polypeptides of the invention are fused with at least one polypeptide of interest. In one embodiment, the invention encompasses fusion polypeptides in which a heterologous polypeptide of interest has an amino acid sequence that is not substantially homologous to the polypeptide of the invention. In this embodiment, the polypeptide of the invention and the polypeptide of interest may or may not be operatively linked. An example of operative linkage is fusion in-frame so that a single polypeptide is produced upon translation. Such fusion polypeptides can, for example, facilitate the purification of a recombinant polypeptide.

In another embodiment, the fused polypeptide of interest may contain a heterologous signal sequence at the N-terminus facilitating its secretion from specific host cells. The expression and secretion of the polypeptide can thereby be increased by use of the heterologous signal sequence.

The invention is also directed to polypeptides in which one or more domains in the polypeptide described herein are operatively linked to heterologous domains having homologous functions. Thus, the toxin binding domain can be replaced with a toxin binding domain for other toxins. Thereby, the toxin specificity of the receptor is based on a toxin binding domain other than the domain encoded by Bt toxin receptor but other characteristics of the polypeptide, for example, membrane localization and topology is based on Bt toxin receptor.

Alternatively, the native Bt toxin binding domain may be retained while additional heterologous ligand binding domains, including but not limited to heterologous toxin binding domains are comprised by the receptor. Thus, the invention also encompasses fusion polypeptides in which a polypeptide of interest is a heterologous polypeptide comprising a heterologous toxin binding domains. Examples of heterologous polypeptides comprising Cry1 toxin binding domains include, but are not limited to Knight et al (1994) *Mol. Micro.* 11: 429–436; Lee et al. (1996) *Appl. Environ. Micro.* 63: 2845–2849; Gill et al. (1995) *J. Biol. Chem.* 270: 27277–27282; Garczynski et al. (1991) *Appl. Environ. Microbiol.* 10: 2816–2820; Vadlamudi et al. (1995) *J. Biol. Chem.* 270(10):5490–4, and U.S. Pat. No. 5,693,491.

The Bt toxin receptor peptide of the invention may also be fused with other members of the cadherin superfamily. Such fusion polypeptides could provide an important reflection of the binding properties of the members of the superfamily. Such combinations could be further used to extend the range of applicability of these molecules in a wide range of systems or species that might not otherwise be amenable to native or relatively homologous polypeptides. The fusion constructs could be substituted into systems in which a native construct would not be functional because of species specific constraints. Hybrid constructs may further exhibit desirable or unusual characteristics otherwise unavailable with the combinations of native polypeptides.

Polypeptide variants encompassed by the present invention include those that contain mutations that either enhance or decrease one or more domain functions. For example, in the toxin binding domain, a mutation may be introduced that increases or decreases the sensitivity of the domain to a specific toxin.

As an alternative to the introduction of mutations, an increase in activity may be achieved by increasing the copy number of ligand binding domains. Thus, the invention also encompasses receptor polypeptides in which the toxin binding domain is provided in more than one copy.

The invention further encompasses cells containing receptor expression vectors comprising the Bt toxin receptor sequences, and fragments and variants thereof. The expression vector can contain one or more expression cassettes used to transform a cell of interest. Transcription of these genes can be placed under the control of a constitutive or inducible promoter (for example, tissue- or cell cycle-preferred).

Where more than one expression cassette utilized, the cassette that is additional to the cassette comprising at least one receptor sequence of the invention, can comprise either a receptor sequence of the invention or any other desired sequences.

The nucleotide sequences of the invention can be used to isolate homologous sequences in insect species other than *Agrotis*, particularly other lepidopteran species, more particularly other *Noctuoidea* species.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11–17; the local alignment of Smith et al. (1981) *Adv. Appl. Math.* 2:482; the global alignment algorithm of Needleman and Wunsch (1970) *J. Mol. Biol.* 48:443–453; the search-for-local alignment method of Pearson and Lipman (1988) *Proc. Natl. Acad. Sci. USA* 85:2444–2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990), supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.hlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, at least 80%, at least 90%, or at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, at least 70%, at least 80%, at least 90%, such as at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid sequence is immunologically cross reactive with the polypeptide encoded by the second nucleic acid sequence.

(e)(ii) The term "substantial identity" in the context of a peptide indicates that a peptide comprises a sequence with at least 70% sequence identity to a reference sequence, at least 80%, at least 85%, such as at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleotide sequences of the invention can be used to isolate corresponding sequences from other organisms, particularly other insects, more particularly other lepidopteran species. In this manner, methods such as PCR, hybridization, and the like can be used to identify such sequences based on their sequence homology to the sequences set forth herein. Sequences isolated based on their sequence identity to the entire Bt toxin receptor sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

Thus, isolated sequences which encode polypeptides having Bt toxin receptor activity and which hybridize under stringent conditions to the BCW Bt toxin receptor sequences disclosed herein, or to fragments thereof, are encompassed by the present invention.

In a PCR-based approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See, also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

Degenerate bases, otherwise known as wobbles, are equimolar mixtures of two or more different bases at a given position within a sequence. Since the genetic code is degenerate (e.g., histidine could be encoded by CAC or CAT), an oligo probe may be prepared with wobbles at the degenerate sites (e.g., for histidine CAY is used where Y=C+T). There are eleven standard wobbles mixtures. The standard code letters for specifying a wobble are as follows: R=A+G; Y=C+T; M=A+C; K=G+T; S=C+G; W=A+T; B=C+G+T; D=A+G+T; H=A+C+T; V=A+C+G; and N=A+C+G+T.

Degenerate bases are used to produce degenerate probes and primers. Degenerate bases are often incorporated into oligonucleotide probes or primers designed to hybridize to an unknown gene that encodes a known amino acid sequence. They may also be used in probes or primers that are designed based upon regions of homology between similar genes in order to identify a previously unknown ortholog. Oligonucleotides with wobbles are also useful in random mutagenesis and combinatorial chemistry.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the Bt toxin receptor sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire Bt toxin receptor sequence disclosed herein, or one or more portions thereof, may be used as a probe capable of specifically hybridizing to corresponding Bt toxin receptor sequences and messenger RNAs. To achieve specific hybridization under a variety of conditions, such probes include sequences that are unique among Bt toxin receptor sequences and are at least about 10 nucleotides in length, or at least about 20 nucleotides in length.

Such probes may be used to amplify corresponding Bt toxin receptor sequences from a chosen plant organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y. ).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, such as less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267–284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for a Bt toxin receptor protein and which hybridize under stringent conditions to the Bt toxin receptor sequences disclosed herein, or to fragments thereof, are encompassed by the present invention.

The compositions and screening methods of the invention are useful for identifying cells expressing the Bt toxin receptors of the invention, and variants and homologues thereof. Such identification could utilize detection methods at the protein level, such as ligand-receptor binding; or at the nucleotide level. Detection of the polypeptide could be in situ by means of in situ hybridization of tissue sections but may also be analyzed by bulk polypeptide purification and subsequent analysis by Western blot or immunological assay of a bulk preparation. Alternatively, receptor gene expression can be detected at the nucleic acid level by techniques well known to those of ordinary skill in any art using complimentary polynucleotides to assess the levels of genomic DNA, mRNA, and the like. As an example, PCR primers complimentary to the nucleic acid of interest can be used to identify the level of expression. Tissues and cells identified as expressing the receptor sequences of the invention are determined to be susceptible to toxins that bind the receptor polypeptides.

Where the source of the cells identified to express the receptor polypeptides of the invention is an organism, for example an insect plant pest, the organism is determined to be susceptible to toxins capable of binding the polypeptides. In a particular embodiment, identification is in a lepidopteran plant pesr expressing the Bt toxin receptor of the invention.

The invention encompasses antibody preparations with specificity against the polypeptides of the invention. In further embodiments of the invention, the antibodies are used to detect receptor expression in a cell.

In one aspect, the invention is drawn to compositions and methods for modulating susceptibility of plant pests to Bt toxins. However, it is recognized that the methods and compositions could be used for modulating susceptibility of any cell or organism to the toxins. By "modulating" is intended that the susceptibility of a cell or organism to the cytotoxic effects of the toxin is increased or decreased. By "suceptibility" is intended that the viability of a cell contacted with the toxin is decreased. Thus the invention encompasses expressing the cell surface receptor polypeptides of the invention to increase susceptibility of a target cell or organ to Bt toxins. Such increases in toxin susceptibility are useful for medical and veterinary purposes in which eradication or reduction of viability of a group of cells is desired. Such increases in susceptibility are also useful for agricultural applications in which eradication or reduction of population of particular plant pests is desired.

Plant pests of interest include, but are not limited to insects, nematodes, and the like. Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The following examples are offered by way of illustration and not by way of limitation.

EXPERIMENTAL

Example 1

Isolation of EC Bt Toxin Receptor

Standard recombinant methods well known to those of ordinary skill in the art were carried out. The Align X program (a component of Vector NTI® Suite software available from Informax, Inc., Bethesda, Md.) was used to identify regions of homology between the protein sequences for the Bt receptors from corn pests including fall armyworm (*Spodoptera frugiperda*), corn earworm (*Helicoverpa zea*), and European corn borer (*Ostriania nubilalis*). The nucleotide sequences encoding the identified regions of homology were then compared and evaluated to identify sequences having a low level of fold degeneracy. Fold degeneracy represents the total number of oligonucleotide sequences required to represent all the possible ways to code for a given sequence of amino acids (see Sambrook et al. (1989) Molecular Cloning, a Laboratory Manual $2^{nd}$ Ed.). PCR primers were then designed based on regions of the aligned sequences that could be used to generate oligonucleotide primers having a fold degeneracy of 1024 or less. The sequence of three of these primers is shown below.

47310 (Sense): 5' GCNATHGAYGGNGAYACGG-GAATC 3' (SEQ ID NO:3)

47313 (Antisense): 5' GGNAGYTCRTCRTTCCARTTG 3' (SEQ ID NO:4)

47315 (Antisense): 5' GAAGCCRKCNCCSWC-NGTCTC 3' (SEQ ID NO:5)

Primer pairs 47310/47313 and 47310/47315 were used to produce two overlapping PCR products with a high level of sequence identity to known Bt toxin receptor sequences. The PCR product generated using the 47310/47315 primer pair encompassed the PCR product generated using the 47310/47313 primer pair and therefore the product generated using the 47310/47315 primer pair was used to used to produce a hybridization probe to screen a BCW midgut cDNA library to identify a Bt toxin receptor clone.

The hybridization probe was produced by random priming a 461 bp ApoI fragment of the PCR product generated using the 47310/47315 primer pair. The primary screen of the library yielded 15 positive plaques. The secondary screen of the primary positives yielded 13 positive plaques. A PCR screen of the secondary positives revealed 2 clones with inserts larger than 3 kilobases in length. An analysis of the insert sequences revealed one insert with a strong sequence homology to known Bt receptors. This insert sequence is represented in SEQ ID NO: 1.

Several positive clones contained cDNA inserts having a high level of sequence similarity with known Bt receptors were isolated from the BCW midgut cDNA library in this manner. The nucleotide sequence corresponding to the longest of theses BCW Bt toxin receptor clones is set forth in SEQ ID NO: 1. The total length of the clone is 5765 base pairs. The coding sequence extends from nucleotides 219–5495. The Cry1A binding site is encoded by nucleotides 4206–4719. The predicted transmembrane domain is encoded by nucleotides 5043–5100. The corresponding deduced amino acid sequence for this BCW Bt toxin receptor clone is set forth in SEQ ID NO: 2. The Cry1a binding site is found at residues 1324–1500 and a transmembrane domain is predicted at residues 1608–1627.

The Align Plus program (available from Scientific and Educational Software, Durham, N.C.) with default parameters was used to compare the nucleotide and amino acid sequences of the BCW Bt toxin receptor with Bt toxin receptors isolated from other Lepidopteran insects. The results of this analysis are shown in Table 1.

TABLE 1

| | Sequence Similarity to BCW Bt toxin receptor | |
|---|---|---|
| Bt Receptor | DNA | Protein |
| *Spodoptera frugiperda*[a] | 60% | 54% |
| *Helicoverpa zea*[a] | 68% | 58% |
| *Ostrinia nubilalis*[a] | 59% | 55% |
| *Bombyx mori*[b] | 59% | 54% |
| *Manduca sexta*[c] | 58% | 57% |

[a]See, PCT Publication WO0136639
[b]See, Ihara et al. (1998) Comparative Biochemistry and Physiology, Part B 120:197–204 and Nagamatsu et al. (1998) Biosci. Biotechnol. Biochem. 62(4):727–734.
[c]See, Vadlamudi et al. (1995) J. Biol. Chem. 270(10):5490-4, Keeton et al. (1998) Appl. Environ. Microbiol. 64(6):2158–2165; Keeton et al. (1997) Appl. Environ. Microbiol. 63(9):3419–3425 and U.S. Pat. No. 5,693,491.

All vectors are constructed using standard molecular biology techniques as described for example in Sambrook et al., (1989) *Molecular Cloning: A Laboratory Manual* ($2^{nd}$ ed., Cold Spring Harbor Laboratory: Cold Spring Harbor, N.Y.).

Expression is tested by ligand blotting and testing for Bt toxin binding. Ligand blotting, binding, and toxicity are tested by known methods; for example, as described in Martinez-Ramirez (1994) *Biochem. Biophys. Res. Comm.* 201: 782–787; Vadlamudi et al. (1995) *J. Biol. Chem.* 270:5490–4; Keeton et al. (1998) *Appl. Environ. Microbiol.* 64:2158–2165; Keeton et al. (1997) *Appl. Environ. Microbiol.* 63:3419–3425; Ihara et al. (1998) *Comparative Biochemistry and Physiology, Part B* 120:197–204; Nagamatsu et al. (1998) *Biosci. Biotechnol. Biochem.* 62:718–726; and Nagamatsu et al. (1998) *Biosci. Biotechnol. Biochem.* 62:727–734.

Example 2

Binding and Cell Death in *Lepidopteran* Insect Cells Expressing the Bt Toxin Receptors of the Invention An in vitro system is developed to demonstrate the functionality of a Bt toxin receptor of the invention. Well known molecular biological methods are used in cloning and expressing the BCW Bt toxin receptor in Sf9 cells. A baculovirus expression system GIBCO™ Invitrogen Corporation, Carlsbad, Calif.) is used according to the manufacturer's provided protocols and as described below. *S. frugiperda* (Sf9) cells obtained from ATCC (ATCC-CRL 1711) are grown at 27° C. in Sf-900 II serum free medium (Gibco™ Invitrogen Corporation, Carlsbad, Calif.). These cells, which are not susceptible to Cry1Ab toxin, are transfected with an expression construct (pFastBac1 bacmid, Gibco™ Invitrogen Corporation, Carlsbad, Calif.) comprising an operably linked Bt toxin receptor of the invention (SEQ ID NO:1) downstream of a polyhedrin promoter. Transfected Sf9 cells express the BCW Bt toxin receptor and are lysed in the presence of Cry1Ab toxin. Toxin specificities, binding parameters, such as $K_d$ values, and half maximal doses for cellular death and/or toxicity are also determined.

For generating expression constructs, the BCW Bt toxin receptor cDNA (SEQ ID NO:1) is subjected to appropriate restriction digestion or PCR amplification, and the resulting cDNA comprising the full-length coding sequence is ligated into the donor plasmid pFastBac1 multiple cloning site. Following transformation and subsequent transposition, recombinant bacmid DNA comprising the BCW Bt toxin receptor (RBBCW1) is isolated. As a control, recombinant bacmid DNA comprising the reporter gene β-glucuronidase (RBGUS) is similarly constructed and isolated.

For transfection, 2 μg each RBBCW1 or RBGUS DNA is mixed with 6 μl of CellFectin (GIBCO™ Invitrogen Corporation, Carlsbad, Calif.) in 100 μl of Sf900 medium, and incubated at room temperature for 30 minutes. The mixture is then diluted with 0.8 ml Sf-900 medium. Sf9 cells ($10^6$/ml per 35 mm well) are washed once with Sf-900 medium, mixed with the DNA/CellFectin mixture, added to the well, and incubated at room temperature for 5 hours. The medium is removed and 2 ml of Sf-900 medium containing penicillin and streptomycin is added to the well. 3–5 days after transfection, Western blotting is used to examine protein expression.

For Western blotting, 100 μl of cell lysis buffer (50 mM Tris, pH7.8, 150 mM NaCl, 1% Nonidet P-40) is added to the well. The cells are scraped and subjected to 16,000×g centrifugation. Pellet and supernatant are separated and subjected to Western blotting. An antibody preparation against BCW Bt toxin receptor is used as first antibody. Alkaline phosphatase-labeled anti-rabbit IgG is used as secondary antibody. Western blot results indicate that the full length BCW Bt toxin receptor of the invention (SEQ ID NO:2) is expressed in the cell membrane of these cells.

For determining GUS activity, the medium of the cells transfected with RBGUS is removed. The cells and the medium are separately mixed with GUS substrate and assayed for the well known enzymatic activity. GUS activity assays indicate that this reporter gene is actively expressed in the transfected cells.

For determining toxin susceptibility, Cry toxins including but not limited to Cry1A, Cry1B, Cry1C, Cry1D, Cry1E, Cry1F, Cry1I, Cry2, Cry3, and Cry9 toxins (Schnepf E. et al. (1998) Microbiology and *Molecular Biology Reviews* 62(3): 775–806) are prepared by methods known in the art. Crystals are dissolved in pH 10.0, 50 mM carbonate buffer and treated with trypsin. Active fragments of Cry proteins are purified by chromatography. Three to five days after transfection, cells are washed with phosphate buffered saline (PBS). Different concentrations of active fragments of Cry toxins are applied to the cells. At different time intervals, the cells are examined under the microscope to readily determine susceptibility to the toxins. Alternatively, cell death, viability and/or toxicity is quantified by methods well known in the art. See, for example, In Situ Cell Death Detection Kits available from Roche Biochemicals (Catalogue Nos. 2 156 792, 1 684 809, and 1 684 817), and LIVE/DEAD® Viability/Cytotoxicity Kit available from Molecular Probes (catalogue No. L-3224).

A dose-dependent response of RBBCW1-transfected cells to Cry1Ab is readily observed, with determined Kd values well within the range for many receptors. Control cells, e.g. those transfected with pFastBac1 bacmid without an insert or those transfected with RBGus are not significantly affected by Cry1Ab. Interaction with other Cry toxins are similarly characterized.

This in vitro system is not only used to verify the functionality of putative Bt-toxin receptors, but also used as a tool to determine the active site(s) and other functional domains of the toxin and the receptor. Furthermore, the system is used as a cell-based high throughput screen. For example, methods for distinguishing live versus dead cells by differential dyes are known in the art. This allows for aliquots of transfected cells to be treated with various toxin samples and to serve as a means for screening the toxin samples for desired specificity or binding characteristics. Since the system is used to identify the specificity of Cry protein receptors, it is a useful tool in insect resistance management.

Example 3

Tissue and Subcellular Expression of the BCW Bt Toxin Receptor

Fifth instar BCW are dissected to isolate the following tissues: fat body (FB), malpighian tubules (MT), hind gut (HG), anterior midgut (AM) and posterior midgut (PM). Midguts from fifth instar larvae are also isolated for brush border membrane vesicle (BBMV) preparation using the well known protocol by Wolfersberger et al. (1987) *Comp. Biochem. Physiol.* 86A:301–308. Tissues are homogenized in Tris buffered saline, 0.1% tween-20, centrifuged to pellet insoluble material, and transferred to a fresh tube. 50 μg of protein from each preparation is added to SDS sample buffer and B-mercaptoethanol, heated to 100° C. for 10 minutes and loaded onto a 4–12% Bis-Tris gel (Novex). After electrophoresis, the proteins are transferred to a nitrocellulose membrane using a semi-dry apparatus. The membrane is blocked in 5% nonfat dry milk buffer for 1 hour at room temperature with gentle agitation. The primary antibody is added to a final dilution of 1:5000 and allowed to hybridize for 1 hour. The blot is then washed three times for 20 minutes each in nonfat milk buffer. The blot is then hybridized with the secondary antibody (goat anti-rabbit with alkaline phosphatase conjugate) at a dilution of 1:10000 for 1 hour at room temperature. Washes are performed as before. The bands are visualized by a standard chemiluminescent protocol (WESTERN-LIGHT™ Immunodetection System, Applied Biosystems, Foster City, Calif.).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. An isolated polypeptide having the amino acid sequence selected from the group consisting of:
   a) the amino acid sequence set forth in SEQ ID NO:2;
   b) the amino acid sequence of a sequence variant of the amino acid sequence set forth in SEQ ID NO:2, wherein said sequence variant has *Bacillus thuringiensis* (Bt) Cry 1A toxin binding activity and shares at least 90% sequence identity with the amino acid sequence set forth in SEQ ID NO:2;
   c) the amino acid sequence of a sequence variant of the amino acid sequence set forth in SEQ ID NO:2, wherein said sequence variant has *Bacillus thuringiensis* (Bt) Cry 1A toxin binding activity and shares at least 95% sequence identity with the amino acid sequence set forth in SEQ ID NO:2;
   d) an amino acid sequence encoded by the nucleotide sequence set forth in SEQ ID NO: 1;
   e) an amino acid sequence encoded by a nucleotide sequence having at least 90% sequence identity across the full length of the nucleotide sequence set forth in SEQ ID NO: 1, wherein said nucleotide sequence having at least 90% sequence identity to the nucleotide sequence set forth in SEQ ID NO:1 encodes a polypeptide having *Bacillus thuringiensis* (Bt) Cry 1A toxin binding activity; and
   f) an amino acid sequence encoded by a nucleotide sequence having at least 95% sequence identity across the full length of the nucleotide sequence set forth in SEQ ID NO: 1, wherein said nucleotide sequence having at least 95% sequence identity to the nucleotide sequence set forth in SEQ ID NO:1 encodes a polypeptide having *Bacillus thuringiensis* (Bt) Cry 1A toxin binding activity.

2. A fusion polypeptide comprising the polypeptide of claim 1 and at least one polypeptide of interest.

3. The fusion polypeptide of claim 2, wherein said polypeptide of interest is a toxin receptor.

* * * * *